US007964569B2

(12) United States Patent
Ernst et al.

(10) Patent No.: US 7,964,569 B2
(45) Date of Patent: Jun. 21, 2011

(54) GLYCOMIMETIC REPLACEMENTS FOR HEXOSES AND N-ACETYL HEXOSAMINES

(75) Inventors: Beat Ernst, Magden (CH); Daniel Schwizer, Basel (CH); Arun K Sarkar, North Potomac, MD (US); John L Magnani, Gaithersburg, MD (US)

(73) Assignee: GlycoMimetics, Inc., Gaithersburg, MD (US)

( * ) Notice: Subject to any disclaimer, the term of this patent is extended or adjusted under 35 U.S.C. 154(b) by 740 days.

(21) Appl. No.: 11/973,891

(22) Filed: Oct. 9, 2007

(65) Prior Publication Data

US 2008/0161546 A1  Jul. 3, 2008

Related U.S. Application Data

(60) Provisional application No. 60/851,467, filed on Oct. 12, 2006.

(51) Int. Cl.
*A61K 31/7034* (2006.01)
(52) U.S. Cl. ............... 514/35; 536/4.1; 536/17.9
(58) Field of Classification Search ............ None
See application file for complete search history.

(56) References Cited

U.S. PATENT DOCUMENTS

| | | | |
|---|---|---|---|
| 4,471,057 A | 9/1984 | Koprowski et al. | 436/518 |
| 4,851,511 A | 7/1989 | Hakomori et al. | 530/387 |
| 4,859,769 A | 8/1989 | Karlsson et al. | 536/53 |
| 4,876,199 A | 10/1989 | Hakamori | 530/387 |
| 4,925,796 A | 5/1990 | Bergh et al. | 435/97 |
| 4,946,830 A | 8/1990 | Pulverer et al. | 514/23 |
| 5,143,712 A | 9/1992 | Brandley et al. | 424/1.1 |
| 5,151,360 A | 9/1992 | Handa et al. | 435/240.2 |
| 5,211,937 A | 5/1993 | Brandley et al. | 424/1.1 |
| 5,268,364 A | 12/1993 | Kojima et al. | 514/25 |
| 5,304,640 A | 4/1994 | Lasky et al. | 536/23.5 |
| 5,352,670 A | 10/1994 | Venot et al. | 514/54 |
| 5,369,096 A | 11/1994 | Yamada et al. | 514/61 |
| 5,412,123 A | 5/1995 | Rao et al. | 552/290 |
| 5,444,050 A | 8/1995 | Kogan et al. | 514/25 |
| 5,464,778 A | 11/1995 | Cummings et al. | 436/503 |
| 5,464,815 A | 11/1995 | Chamow et al. | 514/8 |
| 5,470,843 A | 11/1995 | Stahl et al. | 514/61 |
| 5,484,891 A | 1/1996 | Lasky et al. | 530/387.3 |
| 5,486,536 A | 1/1996 | Ward et al. | 514/460 |
| 5,519,008 A | 5/1996 | Rao et al. | 514/26 |
| 5,527,785 A | 6/1996 | Bevilacqua et al. | 514/56 |
| 5,538,724 A | 7/1996 | Butcher et al. | 424/152.1 |
| 5,559,103 A | 9/1996 | Gaeta et al. | 514/54 |
| 5,576,305 A | 11/1996 | Ratcliffe | 514/25 |
| 5,580,858 A | 12/1996 | Ippolito et al. | 514/25 |
| 5,580,862 A | 12/1996 | Rosen et al. | 514/61 |
| 5,589,465 A | 12/1996 | Ishida et al. | 514/25 |
| 5,604,207 A | 2/1997 | DeFrees et al. | 514/25 |
| 5,618,785 A | 4/1997 | Heavner et al. | 514/2 |
| 5,622,937 A | 4/1997 | Kogan et al. | 514/25 |
| 5,639,734 A | 6/1997 | Esko et al. | 514/25 |
| 5,646,123 A | 7/1997 | Ippolito et al. | 514/25 |
| 5,646,248 A | 7/1997 | Sawada et al. | 530/350 |
| 5,648,344 A | 7/1997 | Brandley et al. | 514/61 |
| 5,654,282 A | 8/1997 | Tang et al. | 514/25 |
| 5,654,412 A | 8/1997 | Srivastava et al. | 536/18.5 |
| 5,658,880 A | 8/1997 | Dasgupta et al. | 514/8 |
| 5,663,151 A | 9/1997 | Martel et al. | 514/25 |
| 5,679,321 A | 10/1997 | Dasgupta et al. | 424/9.1 |
| 5,679,644 A | 10/1997 | Rao et al. | 514/26 |
| 5,686,426 A | 11/1997 | Martel et al. | 514/25 |
| 5,693,621 A | 12/1997 | Toepfer et al. | 514/25 |
| 5,695,752 A | 12/1997 | Rosen et al. | 424/94.61 |
| 5,710,023 A | 1/1998 | Collins et al. | 435/69.1 |
| 5,710,123 A | 1/1998 | Heavner et al. | 514/2 |
| 5,723,583 A | 3/1998 | Seed et al. | 530/387.3 |
| 5,728,685 A | 3/1998 | Abbas et al. | 514/53 |
| 5,739,300 A | 4/1998 | Toepfer et al. | 536/4.1 |
| 5,747,463 A | 5/1998 | Marinier et al. | 514/25 |
| 5,750,508 A | 5/1998 | Dasgupta et al. | 514/25 |
| 5,753,617 A | 5/1998 | Heavner et al. | 514/9 |
| 5,753,631 A | 5/1998 | Paulson et al. | 514/25 |
| 5,763,413 A | 6/1998 | Numata et al. | 514/25 |
| 5,763,582 A | 6/1998 | Rao et al. | 536/5 |
| 5,789,385 A | 8/1998 | Anderson et al. | 514/25 |
| 5,789,573 A | 8/1998 | Baker et al. | 536/24.5 |
| 5,795,958 A | 8/1998 | Rao et al. | 530/331 |
| 5,811,404 A | 9/1998 | De Frees et al. | 514/25 |
| 5,811,405 A | 9/1998 | Toepfer et al. | 514/25 |
| 5,817,742 A | 10/1998 | Toepfer et al. | 528/328 |
| 5,827,817 A | 10/1998 | Larsen et al. | 514/2 |
| 5,827,837 A | 10/1998 | Bevilacqua et al. | 514/103 |
| 5,830,871 A | 11/1998 | Wong et al. | 514/23 |
| 5,837,689 A | 11/1998 | Anderson et al. | 514/25 |

(Continued)

FOREIGN PATENT DOCUMENTS

EP  319253 A2  6/1989

(Continued)

OTHER PUBLICATIONS

Ernst, B. et al "Design and synthesis of E-selectin antagonists" Chimie (2001) vol. 55, No. 4, pp. 268-274.*
Ernst, B. et al "Design and Synthesis of E-selectin antagonists" Chimia (2001) vol. 55, No. 4, pp. 268-274.*
Titz, A. et al "Probing the carbohydrate recognition domain of E-selectin . . . " Bioorg. Med. Chem. (2010) vol. 18, pp. 19-27.*
Abraham, W.M. et al., "Selectin Blockade Prevents Antigen-induced Late Bronchial Response and Airway Hyperresponsiveness in Allergic Sheep," *Am J. Respir Crit Care Med.* 159: 1205-1214, 1999.
Acord, J. et al., "A rapid microplate method for quantifying inhibition of bacterial adhesion to eukaryotic cells," *Journal of Microbiological Methods* 60: 55-62, 2005.

(Continued)

*Primary Examiner* — Leigh C Maier
(74) *Attorney, Agent, or Firm* — Seed IP Law Group PLLC

(57) ABSTRACT

Compounds and methods are provided for obtaining oligosaccharide mimics. More specifically, compounds and methods are described wherein oligosaccharide mimics are obtained by incorporating or substituting in a cyclohexane derivative.

13 Claims, 13 Drawing Sheets

U.S. PATENT DOCUMENTS

| | | | |
|---|---|---|---|
| 5,837,690 A | 11/1998 | Rao et al. | 514/26 |
| 5,840,679 A | 11/1998 | Larsen et al. | 514/8 |
| 5,854,218 A | 12/1998 | DeFrees | 514/25 |
| 5,858,983 A | 1/1999 | Seed et al. | 514/23 |
| 5,858,994 A | 1/1999 | Kretzschmar et al. | 514/62 |
| 5,880,091 A | 3/1999 | Cummings et al. | 514/8 |
| 5,916,910 A | 6/1999 | Lai | 514/423 |
| 5,919,768 A | 7/1999 | Kogan et al. | 514/25 |
| 5,919,769 A | 7/1999 | Tsukida et al. | 514/25 |
| 5,962,422 A | 10/1999 | Nagy et al. | 514/25 |
| 5,976,540 A | 11/1999 | Rittershaus et al. | 424/184.1 |
| 5,977,080 A | 11/1999 | Rosen et al. | 514/25 |
| 5,985,852 A | 11/1999 | Nagy et al. | 514/54 |
| 5,994,402 A | 11/1999 | Rotstein et al. | 514/547 |
| 6,001,819 A | 12/1999 | Simon et al. | 514/54 |
| 6,001,988 A | 12/1999 | Parma et al. | 536/24.3 |
| 6,033,665 A | 3/2000 | Yednock et al. | 424/130.1 |
| 6,037,333 A | 3/2000 | Panjwani | 514/62 |
| 6,110,897 A | 8/2000 | Unverzagt et al. | 514/25 |
| 6,111,065 A | 8/2000 | Heavner et al. | 530/300 |
| 6,120,751 A | 9/2000 | Unger | 424/9.51 |
| 6,121,233 A | 9/2000 | Magnani et al. | 514/8 |
| 6,124,267 A | 9/2000 | McEver et al. | 514/25 |
| 6,133,239 A | 10/2000 | Handa et al. | 514/25 |
| 6,133,240 A | 10/2000 | Taylor et al. | 514/25 |
| 6,136,790 A | 10/2000 | Toepfer et al. | 514/25 |
| 6,169,077 B1 | 1/2001 | Oehrlein | 514/25 |
| 6,177,547 B1 | 1/2001 | Cummings et al. | 530/388.22 |
| 6,187,754 B1 | 2/2001 | Oehrlein | 514/25 |
| 6,193,973 B1 | 2/2001 | Tuttle | 424/195.1 |
| 6,193,979 B1 | 2/2001 | Rittershaus et al. | 424/195.11 |
| 6,197,752 B1 | 3/2001 | Schmidt et al. | 514/23 |
| 6,225,071 B1 | 5/2001 | Cummings et al. | 435/7.24 |
| 6,235,309 B1 | 5/2001 | Nagy et al. | 424/450 |
| 6,280,932 B1 | 8/2001 | Parma et al. | 435/6 |
| 6,309,639 B1 | 10/2001 | Cummings et al. | 424/143.1 |
| 6,387,884 B1 | 5/2002 | Magnani et al. | 514/25 |
| 6,391,857 B1 | 5/2002 | Magnani et al. | 514/25 |
| 6,407,135 B1 | 6/2002 | Lai et al. | 514/423 |
| 6,465,434 B1 | 10/2002 | Magnani et al. | 514/23 |
| 6,492,332 B1 | 12/2002 | Demopulos et al. | 514/12 |
| 6,503,885 B1 | 1/2003 | Kiso et al. | 514/25 |
| 6,528,487 B1 | 3/2003 | Heavner et al. | 514/13 |
| 2001/0046970 A1 | 11/2001 | Nagy et al. | 514/53 |
| 2001/0051370 A1 | 12/2001 | Bistrup et al. | 435/193 |
| 2002/0026033 A1 | 2/2002 | Cummings et al. | 530/322 |
| 2002/0028205 A1 | 3/2002 | Holgersson et al. | 424/184.1 |
| 2002/0031508 A1 | 3/2002 | Wagner et al. | 424/94.63 |
| 2002/0040008 A1 | 4/2002 | Wagner et al. | 514/41 |
| 2002/0132220 A1 | 9/2002 | Berens et al. | 435/1.1 |
| 2002/0164336 A1 | 11/2002 | Harrison et al. | 424/146.1 |
| 2002/0164748 A1 | 11/2002 | Bistrup et al. | 435/193 |
| 2002/0168366 A1 | 11/2002 | Stewart et al. | 424/146.1 |
| 2003/0012787 A1 | 1/2003 | Ashkenazi et al. | 424/145.1 |
| 2003/0012790 A1 | 1/2003 | Ashkenazi et al. | 424/178.1 |
| 2003/0018181 A1 | 1/2003 | Larsen et al. | 536/23.4 |
| 2003/0039683 A1 | 2/2003 | Cantrell et al. | 424/450 |
| 2007/0054870 A1* | 3/2007 | Magnani et al. | 514/35 |

FOREIGN PATENT DOCUMENTS

| | | |
|---|---|---|
| EP | 381310 A1 | 8/1990 |
| EP | 408859 B2 | 8/1995 |
| EP | 671407 A2 | 9/1995 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |
| WO | WO 94/29477 | 12/1994 |
| WO | WO 95/03059 | 2/1995 |
| WO | WO 95/29681 | 11/1995 |
| WO | WO 96/20204 | 7/1996 |
| WO | WO 96/25418 | 8/1996 |
| WO | WO 96/26950 | 9/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 99/42130 | 8/1999 |
| WO | WO 99/43353 | 9/1999 |
| WO | WO 99/43356 | 9/1999 |
| WO | WO 02/22820 | 3/2002 |
| WO | WO 02/062810 | 8/2002 |
| WO | WO 03/097658 | 11/2003 |
| WO | WO 2004/004636 | 1/2004 |
| WO | WO 2004/058304 | 7/2004 |
| WO | WO 2005/054264 | 6/2005 |
| WO | WO 2006/127906 | 11/2006 |
| WO | WO 2007/028050 | 3/2007 |

OTHER PUBLICATIONS

Baeckström et al., "Purification and Characterization of a Membrane-bound and a Secreted Mucin-type Glycoprotein Carrying the Carcinoma-associated Sialyl-Le$^a$ Epitope on Distinct Core Proteins," *J. Biol. Chem.* 266(32):21537-21547, 1991.

Bänteli, R. et al., "Potent E-Selectin Antagonists," *Helvetica Chimica Acta* 83(11): 2893-2907, 2000.

Berg et al., "A Carbohydrate Domain Common to Both Sialyl Le$^a$ and Sialyl Le$^x$ Is Recognized by the Endothelial Cell Leukocyte Adhesion Molecule ELAM-1," *J. Biol. Chem.* 266(23):14869-14872, 1991.

Berg et al., "The Cutaneous Lymphocyte Antigen Is a Skin Lymphocyte Homing Receptor for the Vascular Lectin Endothelial Cell-Leukocyte Adhesion Molecule 1," *J. Exp. Med.* 174:1461-1466, 1991.

Bird and Kimber, "Oligosaccharides Containing Fucose Linked α(1-3) and α(1-4) to N-Acetylglucosamine Cause Decompaction of Mouse Morulae," *Devel. Biol.* 104:449-460, 1984.

Bowen et al., "Characterization of a Human Homologue of the Murine Peripheral Lymph Node Homing Receptor," *Journal of Cell Biology* 109:421-427, 1989.

Brandley et al., "Carbohydrate Ligands of LEC Cell Adhesion Molecules," *Cell* 63:861-863, 1990.

Broquet et al., "Effect of Desipramine on a Glycoprotein Sialyltransferase Activity in C6 Cultured Glioma Cells," *J. Neurochem.* 54:388-394, 1990.

Ceder, O. et al., "On the Absolute Configuration of 3-Cyclohexene-l-carboxylic Acid," *Acta Chemica Scandinavica* 24(8):2693-2698, 1970.

Childs et al., "High-molecular-weight glycoproteins are the major carriers of the carbohydrate differentiation antigens I, i and SSEA-1 of mouse teratocarcinoma cells," *Biochem. J.* 215:491-503, 1983.

Corral et al., "Requirements for Sialic Acid on Neutrophils in a GMP-140 (PADGEM) Mediated Adhesive Interaction with Activated Platelets," *Biochem. Biophys. Res. Commun.* 172:1349-1356, 1990.

Datta and Takayama, "Isolation and purification of trehalose 6-mono- and 6,6'-di-corynomycolates from *Cornyebacterium matruchotii*. Structural characterization of $^1$H NMR," *Carbohydrate Research* 245: 151-158, 1993.

Duijvestijn et al., "High Endothelial Differentiation in Human Lymphoid and Inflammatory Tissues Defined by Monoclonal Antibody HECA-452," *Am. J. Path.* 130:147-155, 1988.

Dupré, B. et al., "Glycomimetic Selectin Inhibitors: (α-D-Mannopyranosyloxy)methylbiphenyls," *Bioorganic & Medicinal Chemistry Letters* 6(5): 569-572, 1996.

Edgington, "How Sweet It Is: Selectin-Mediating Drugs," *Biotechnology* 10: 383-389, 1992.

Eggens et al., "A Role of Carbohydrate-Carbohydrate Interaction in the Process of Specific Cell Recognition During Embryogenesis and Organogenesis: A Preliminary Note," *Biochem. Biophys. Res. Commun.* 158(3):913-920, 1989.

Eggens et al., "Specific Interaction between Le$^x$ and Le$^x$ Determinants. A Possible Basis for Cell Recognition in Preimplantation Embryos and in Embryonal Carcinoma Cells," *J. Biol. Chem.* 264(16):9476-9484, 1989.

Ernst and Oehrlein, "Substrate and donor specificity of glycosyl transferases," *Glycoconjugate Journal* 16: 161-170, 1999.

Fenderson et al., "A Multivalent Lacto-*N*-Fucopenataose III-Lysyllysine Conjugate Decompacts Preimplantation Mouse Embryos, While the Free Oligosaccharide is Ineffective," *J. Exp. Med. 160*:1591-1596, 1984.

Fenderson et al., "Coordinate Expression of X and Y Haptens during Murine Embryogenesis," *Devel. Biol. 114*:12-21, 1986.

Fenderson et al., "The blood group I antigen defined by monoclonal antibody C6 is a marker of early mesoderm during murine embryogenesis," *Differentiation 38*:124-133, 1988.

Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," *J. Biol. Chem. 259*(7):4681-4685, 1984.

Fukushi et al., "Novel Fucolipids Accumulating in Human Adenocarcinoma. III. A Hybridoma Antibody (FH6) Defining a Human Cancer-Associated Difucoganglioside ($VI^3NeuAcV^3III^3Fuc_2nLc_6$)," *J. Biol. Chem. 259*(16):10511-10517, 1984.

Gabius et al., "Endogenous Tumor Lectins: Overview and Perspectives," *Anticancer Res. 6*:573-578, 1986.

Gais, H.-J. et al., "Enantioselective and Enantioconvergent Syntheses of Building Blocks for the Total Synthesis of Cyclopentanoid Natural Products," *Angewandte Chemie, Int. Ed. Eng. 23*(2):142-143, 1984.

Gallatin et al., "A cell-surface molecule involved in organ-specific homing of lymphocytes," *Nature 304*:30-34, 1983.

Gooi et al., "Stage-specific embryonic antigen involves α 1 → 3 fucosylated type 2 blood group chains," *Nature 292*:156-158, 1981.

Hakomori et al., "Novel Fucolipids Accumulating in Human Adenocarcinoma. I. Glycolipids With Di- or Trifucosylated Type 2 Chain," *J. Biol. Chem. 259*(7):4672-4680, 1984.

Hakomori et al., "The Hapten Structure of a Developmentally Regulated Glycolipid Antigen (SSEA-1) Isolated From Human Erythrocytes and Adenocarcinoma: A Preliminary Note," *Biochem. Biophys. Res. Comm. 100*(4):1578-1586, 1981.

Hakomori S., "Aberrant Glycosylation in Cancer Cell Membranes as Focused on Glycolipids: Overview and Perspectives," *Cancer Res. 45*:2405-2414, 1985.

Handa et al., "Selectin GMP-140 (CD62; PADGEM) Binds to Sialosyl-Le$^a$ and Sialosyl-Le$^x$, and Sulfated Glycans Modulate this Binding," *Biochemical and Biophysical Research Communication 181*(3):1223-1230, 1991.

Hansson and Zopf, "Biosynthesis of the Cancer-associated Sialyl-Le$^a$ Antigen," *Journal of Biological Chemistry 260*(16):9388-9392, 1985.

Hasegawa et al., "Synthesis of deoxy-L-fucose-containing sialyl Lewis X ganglioside analogues," *Carbohydrate Research 257*: 67-80, 1994.

Hasegawa et al., "Synthesis of sialyl Lewis X ganglioside analogues containing modified L-fucose residues," *Carbohydrate Research 274*: 165-181, 1995.

Holmes et al., "Enzymatic Basis for the Accumulation of Glycolipids with X and Dimeric X Determinants in Human Lung Cancer Cells (NCI-H69)," *J. Biol. Chem. 260*(12):7619-7627, 1985.

Huse et al., "Generation of a Large Combinatorial Library of the Immunoglobulin Repertoire in Phage Lambda," *Science 246*:1275-1281, 1989.

Hynes, R., "Integrins: A Family of Cell Surface Receptors," *Cell 48*:549-554, 1987.

Issekutz, T., "Inhibition of in Vivo Lymphocyte Migration of Inflammation and Homing to Lymphoid Tissues by the TA-2 Monoclonal Antibody. A Likely Role for VLA-4 in Vivo," *Journal of Immunology 147*:4178-4184, 1991.

Itai, S. et al., "Differentiation-dependent Expression of I and Sialyl I Antigens in the Developing Lung of Human Embryos and in Lung Cancers," *Cancer Research 50*: 7603-7611, 1990.

Jeffrey et al., "Affinity Chromatography of Carbohydrate-Specific Immunoglobulins: Coupling of Oligosaccharides to Sepharose ," *Biochem. Biophys. Res. Commun. 62*:608-613, 1975.

Jentsch, K.D. et al., "Inhibition of Human Immunodeficiency Virus Type I Reverse Transcriptase by Suramin-related Compounds," *The Journal of General Virology 68*(8): 2183-2192, 1987.

Kannagi et al., "New Globoseries Glycosphingolipids in Human Teratocarcinoma Reactive with the Monoclonal Antibody Directed to a Developmentally Regulated Antigen, Stage-specific Embryonic Antigen 3," *J. Biol. Chem. 258*(14):8934-8942, 1983.

Kannagi et al., "Stage-specific embryonic antigens (SSEA-3 and -4) are epitopes of a unique globo-series ganglioside isolated from human teratocarcinoma cells," *Embo J. 2*(12):2355-2361, 1983.

Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," *Cancer Biochem. Biophys. 11*:311-315, 1990.

Kitagawa et al., "Characterization of Mucin-Type Oligosaccharides With the Sialyl-Le$^a$ Structure From Human Colorectal Adenocarcinoma Cells," *Biochem. Biophys. Res. Commun. 178*(3):1429-1436, 1991.

Kitagawa et al., "Immunoaffinity Isolation of a Sialyl-Le$^a$ Oligosaccharide from Human Milk," *J. Biochem. 104*:591-594, 1988.

Köhler and Milstein, "Continuous cultures of fused cells secreting antibody of predefined specificity," *Nature 256*:495-497, 1975.

Köhler and Milstein, "Derivation of specific antibody-producing tissue culture and tumor lines by cell fusion," *Eur. J. Immunol. 6*:511-519, 1976.

Kojima and Hakomori, "Specific Interaction between Gangliotriaosylceramide ($G_{g3}$) and Sialosyllactosylceramide ($G_{M3}$) as a Basis for Specific Cellular Recognition between Lymphoma and Melanoma Cells," *J. Biol. Chem. 264*(34):20159-20162, 1989.

Koprowski et al., "Colorectal Carcinoma Antigens Detected by Hybridoma Antibodies," *Somatic Cell Genetics 5*(6):957-972, 1979.

Kogan, T.P. et al., "Novel Synthetic Inhibitors of Selectin-Mediated Cell Adhesion: Synthesis of 1,6-Bis[3-(3-carboxymethylphenyl)-r-(2-α-D-monnopyranosyloxy)phenyl]hexane (TBC1269),"*J. Med. Chem 41*:1099-1111, 1998.

Kogan, T.P. et al., "Rational Design and Synthesis of Oligosaccharide Mimetics: Selectin Antagonists as Cell Adhesion Inhibitors," *Abstracts of Papers, 210$^{th}$ ACS National Meeting*, American Chemical Society, Chicago, IL, Aug. 20-24, 1995, MEDI-18.

Kogan, T.P. et al., "Rational Design and Synthesis of Small Molecule, Non-oligosaccharide Selectin Inhibitors: (α-D-Mannopyranosyloxy)biphenyl-Substituted Corboxylic Acids," *J. Med. Chem. 38*: 4976-4984, Dec. 22, 1995.

Kuzuoka, "Antitumor activity of murine monoclonal antibody NCC-ST-421," *Chem. Ab. 115*:27344v, 1991.

Lamblin et al., "Primary Structure Determination of Five Sialylated Oligosaccharides Derived from Bronchial Mucus Glycoproteins of Patients Suffering from Cystic Fibrosis. The Occurrence of the NeuAcα(2→3)Galβ(1→4)[Fucα(1→3)]GlcNAcβ(1→○) Structural Element Revealed by 500-Mhz H NMR Spectroscopy," *Journal of Biological Chemistry 259*(14):9051-9058, 1984.

Larsen et al., PASDGEM-Dependent Adhesion of Platelets to Monocytes and Neutrophils is Mediated by a Lineage-Specific Carbohydrate, LNF III (CD15), *Cell 63*:467-474, 1990.

Lindenberg et al., "Carbohydrate binding properties of mouse embryos," *J. Reprod. Fert. 89*:431-439, 1990.

Lipartiti et al., "Monosialoganglioside GM1 Reduces NMDA Neurotoxicity in Neonatal Rat Brain," *Experimental Neurology 113*:301-305, 1991.

Lowe et al., "A transfected human fucosyltransferase cDNA determines biosynthesis of oligosaccharide ligand(s) for endothelial-leukocyte adhesion molecule I," *Biochem. Soc. Trans. 19*(3):649-653, 1991.

Lowe et al., "ELAM-1-Dependent Cell Adhesion to Vascular Endothelium Determined by a Transfected Human Fucosyltransferase cDNA," *Cell 63*:475-484, 1990.

Macher et al., "A Novel Carbohydrate, Differentiation Antigen on Fucogangliosides of Human Myeloid Cells Recognized by Monoclonal Antibody VIM-2," *Journal of Biological Chemistry 263*(21):10186-10191, 1988.

Magnani et al., "Identification of the Gastrointestinal and Pancreatic Cancer-associated Antigen Detected by Monoclonal Antibody 19-9 in the Sera of Patients as a Mucin," *Cancer Res. 43*:5489-5492, 1983.

Magnani et al., "A Monoclonal Antibody-defined Antigen Associated with Gastrointestinal Cancer Is a Ganglioside Containing Sialylated Lacto-*N*-fucopentaose II," *Journal of Biological Chemistry 257*(23):14365-14369, 1982.

Magnani, J., "Carbohydrate Sequences Detected by Murine Monoclonal Antibodies," *Chemistry and Physics of Lipids* 42:65-74, 1986.

Magnani, J., "Potent Glycomimetic Inhibitors of the Adhesion Molecule, PA-IIL, for the Bacterial Pathogen, *Pseudomonas auroginosa*," *Glycobiology* 13(11): 854, Abstract No. 104, Oct. 2003.

Mulligan and Berg, "Selection for animal cells that express the *Escherichia coli* gene coding for xanthine-gunine phosphoribosyltransferase," *Proc. Natl. Acad. Sci. USA* 78:2072-2076, 1981.

Nicolaou et al., "Total Synthesis of the Tumor-Associated Le$^X$ Family of Glycosphingolipids," *J. Amer. Chem. Soc.* 112:3693-3695, 1990.

Nudelman et al., "Novel Fucolipids of Human Adenocarcinoma: Disialosyl Le$^a$ Antigen (III$^4$FucIII$^6$NeuAcIV$^3$NeuAcLc$_4$) of Human Colonic Adenocarcinoma and the Monoclonal Antibody (FH7) Defining This Structure," *J. Biol. Chem.* 261:5487-5495, 1986.

Örhlein, R., "Carbohydrates and Derivatives as Potential Drug Candidates with Emphasis on the Selectin and Linear-B Area," *Mini Reviews in Medicinal Chemistry* 1: 349-361, 2001.

Palcic et al., "Enzymic Synthesis of Oligosaccharides Terminating in the Tumor-Associated Sialyl-Lewis-a Determinant," *Carbohydr. Res.* 190:1-11, 1989.

Palcic et al., "Regulation of *N*-Acetylglucosaminyltransferase V Activity. Kinetic Comparisons of Parental, Rous Sarcoma Virus-Transformed BHK, and L-Phytohemagglutinin-Resistant BHK Cells Using Synthetic Substrates and an Inhibitory Substrate Analog," *J. Biol. Chem.* 265:6759-6769, 1990.

Palcic et al., "A Bisubstrate Analog Inhibitor for $\alpha(1 \to 2)$-Fucosyltransferase," *J. Biol. Chem.* 264:17174-17181, 1989.

Palma-Vargas, J.M. et al., "Small-Molecule Selectin Inhibitor Protects Against Liver Inflammatory Response After Ischemia and Reperfusion," *J. Am. Coll. Surg.* 185: 365-372, 1997.

Perret, S. et al., "Structural basis for the interaction between human milk oligosaccharides and the bacterial lectin PA-IIL of *Pseudomonas aeruginosa*," *Biochem. J.* 389: 325-332, 2005.

Phillips et al., "ELAM-1 Mediates Cell Adhesion by Recognition of a Carbohydrate Ligand, Sialyl-Le$^X$," *Science* 250:1130-1132, 1990.

Picker et al., "The Neutrophil Selectin LECAM-1 Presents Carbohydrate Ligands to the Vascular Selectins ELAM-1 and GMP-140," *Cell* 66:921-933, 1991.

Prokazova et al., "Sialylated lactosylceramides. Possible inducers of non-specific immunosuppression and atherosclerotic lesions," *European Journal of Biochemistry* 172:1-6, 1988.

Rauvala et al., "Studies on Cell Adhesion and Recognition. I. Extent and Specificity of Cell Adhesion Triggered by Carbohydrate-reactive Proteins (Glycosidases and Lectins) and by Fibronectin," *J. Cell Biol.* 88:127-137, 1981.

Rice and Bevilacqua, "An Inducible Endothelial Cell Surface Glycoprotein Mediates Melanoma Adhesion," *Science* 246:1303-1306, 1989.

Ruoslahti and Pierschbacher, "New Perspectives in Cell Adhesion: RGD and Integrins," *Science* 238:491-497, 1987.

Sakurai et al., "Selection of a Monoclonal Antibody Reactive with a High-Molecular-Weight Glycoprotein Circulating in the Body Fluid of Gastrointestinal Cancer Patients," *Cancer Research* 48:4053-4058, 1988.

Sastry et al., "Cloning of the immunological repertoire in *Escherichia coli* for generation of monoclonal catalytic antibodies: Construction of a heavy chain variable region-specific cDNA library," *Proc. Natl. Acad. Sci. USA* 86:5728-5732, 1989.

Scharfman, A. et al., "*Pseudomonas aeruginosa* binds to neoglycoconjugates bearing mucin carbohydrate determinants and predominantly to sialyl-Lewis x conjugates," *Glycobiology* 9(8): 757-764, 1999.

Scharfman, A. et al., "Recognition of Lewis x Derivatives Present on Mucins by Flagellar Components of *Pseudomonas aeruginosa*," *Infection and Immunity* 69(9): 5243-5248, Sep. 2001.

Shitara et al., "Application of Anti-Sialyl Le$^a$ Monoclonal antibody, KM231, for Immunotherapy of Cancer," *Anticancer Res.* 11:2003-2014, 1991.

Siuzdak et al., "Examination of the Sialyl Lewis X—Calcium Complex by Electrospray Mass Spectrometry," *Bioorganic & Medicinal Chemistry Letters* 4(24): 2863-2866, 1994.

Sprengard, U. et al., "Synthesis and Biological Activity of Novel Sialyl-Lewis$^X$ Conjugates," *Bioorganic & Medicinal Chemistry Letters* 6(5): 509-514, 1996.

Stanley and Atkinson, "The LEC11 Chinese Hamster Ovary Mutant Synthesizes *N*-Linked Carbohydrates Containing Sialylated, Fucosylated Lactosamine Units. Analysis by One- and Two-Dimensional H NMR Spectroscopy," *J. Biol. Chem.* 263(23):11374-11381, 1988.

Stephens and Cockett, "The construction of highly efficient and versatile set of mammalian expression vectors," *Nucleic Acids Research.* 17:7110, 1989.

Streeter et al., "Immunohistologic and Functional Characterization of a Vascular Addressin Involved in Lymphocyte Homing into Peripheral Lymph Nodes," *Journal of Cell Biology* 107: 1853-1862, 1988.

Stroud et al., "Extended Type 1 Chain Glycosphingolipids: Dimeric Le$^a$ (III$^4$V$^4$Fuc$_2$Lc$_6$) as Human Tumor-associated Antigen," *J. Biol. Chem.* 266(13):8439-8446, 1991.

Svenson and Lindberg, "Coupling of Acid Labile *Salmonella* Specific Oligosaccharides to Macromolecular Carriers," *J. Immunol. Meth.* 25:323-335, 1979.

Takada et al., "Adhesion of Human Cancer Cells to Vascular Endothelium Mediated by a Carbohydrate Antigen, Sialyl Lewis A$^1$," *Biochem. Biophys. Res. Commun.* 179(2):713-719, 1991.

Takeichi, M., "Cadherins: a molecular family essential for selective cell-cell adhesion and animal morphogenesis," *Trends Genet.* 3(8):213-217, 1987.

Thoma, G. et al., "A readily Available, Highly Potent E-Selectin Antagonist," *Angew. Chem. Int. Ed.* 40(19): 3644-3647, 2001.

Thoma, G. et al., "Preorganization of the Bioactive Conformation of Sialyl Lewis$^x$ Analogues Correlates with Their Affinity to E-Selectin," *Angew. Chem. Int. Ed.* 40(10): 1941-1945, 2001.

Thoma, G. et al., "Synthesis and Biological Evaluation of a Sialyl Lewis X Mimic with Significantly Improved E-selectin Inhibition," *Bioorganic & Medicinal Chemistry Letters* 11: 923-925, 2001.

Tilton, R.G., "Endotoxin-Induced Leukocyte Accumulation in Aqueous Fluid of Rats is Decreased by a Small Molecule Selectin," *Investigative Opthalmology & Visual Science* 37(3): S918, Abstract No. 4227, Feb. 15, 1996.

Trouet et al., "A covalent linkage between daunorubicin and proteins that is stable in serum and reversible by lysosomal hydrolases, as required for a lysosomotropic drug-carrier conjugate: In vitro and in vivo studies," *Proc. Natl. Acad. Sci. USA* 79:626-629, 1982.

Tyrrell et al., "Structural requirements for the carbohydrate ligand of E-selectin," *Proc. Natl. Acad. Sci. USA* 88:10372-10376, 1991.

Waldmann, H. et al., "Synthesis of 2-Acetamindo-2-Deoxyglucosylasparagine Glyco-Tripeptide and -Pentapeptides by Selective C- and N-Terminal Elongation of the Peptide Chain," *Carbohydrate Research* 196: 75-93, 1990.

Walz et al., "Recognition by ELAM-1 of the Sialyl-Le$^X$ Determinant on Myeloid and Tumor Cells," *Science* 250:1132-1135, 1990.

Ward and Mulligan, "Blocking of adhesion molecules in vivo as anti-inflammatory therapy," *Immunology* 1: 165-171, 1994.

Whisler and Yates, "Regulation of Lymphocyte Responses by Human Gangliosides. I. Characteristics of Inhibitory Effects and the Induction of Impaired Activation," *Journal of Immunology* 125(5):2106-2111, 1980.

Yamazaki, F. et al., "Syntheisis of an appropriately protected core glycotetraoside, a key intermediate for the synthesis of 'bisected' complex-type glycans of a glycoprotein," *Carbohydrate Research* 201: 15-30, 1990.

Zhou et al., "The Selectin GMP-140 Binds to Sialylated, Fucosylated Lactosaminoglycans on Both Myeloid and Nonmyeloid Cells," *Journal of Cell Biology* 115(2):557-564, 1991.

Zopf et al., "Affinity Purification of Antibodies Using Oligosaccharide-Phenethylamine Derivatives Coupled to Sepharose," *Meth. Enzymol.* 50:171-175, 1978.

Cleophax, J. et al., "A chiral synthesis of D-(+)-2,6-dideoxystreptamine and its microbial incorporation into novel antibodies," *Journal of the American Chemical Society* 98 (22): 7110-7112, Oct. 27, 1976.

Kalia, N. et al., "Design and synthesis of sialyl Lewis(x) mimics as E- and P-selectin inhibitors," *Med Res Rev* 22(6):566-601, Nov. 2002.

Kneuer, C et al., "Selectins—potential pharmacological targets?" *Drug Discov Today* 11(21-22):1034-1040, Nov. 2006.

Matsui, NM et al., "P-selectin mediates the adhesion of sickle erythrocytes to the endothelium," *Blood* 98(6):1955-1962, Sep. 15, 2001.

Thoma, G. et al., "Synthesis and biological evaluation of a potent E-selectin antagonist," *J Med Chem* 42 (23): 4909-4913, Nov. 18, 1999.

* cited by examiner

GLYCOMIMETIC REPLACEMENTS FOR HEXOSES AND N-ACETYL HEXOSAMINES

CROSS-REFERENCE TO RELATED APPLICATION

This application claims the benefit under 35 U.S.C. §119 (e) of U.S. Provisional Patent Application No. 60/851,467 filed Oct. 12, 2006 which application is incorporated herein by reference in its entirety.

BACKGROUND

1. Technical Field

The present invention relates generally to compounds and methods for obtaining oligosaccharide mimics, and more particularly for obtaining oligosaccharide mimics by incorporating or substituting in a cyclohexane derivative.

2. Description of the Related Art

Naturally occurring monosaccharides and oligosaccharides play a role, or are capable of playing a role, in a variety of biological processes. In certain cases, non-naturally occurring monosaccharides and oligosaccharides may serve to replace or even improve upon their naturally occurring counterparts. Monosaccharides and particularly oligosaccharides may be difficult, and thus costly, to produce. Even where the degree of difficulty to produce is not particularly elevated, the production of monosaccharides and oligosaccharides may still nevertheless be costly. This problem is multiplied where a costly monosaccharide or oligosaccharide needs to be mass produced. While mimics of monosaccharides and oligosaccharides ("glycomimetics") may improve upon their biological properties, the cost of producing the mimics may not be significantly reduced relative to that which they mimic.

Accordingly, there is a need in the art for reducing the production cost or complexity of glycomimetics. The present invention fulfills these needs and further provides other related advantages.

BRIEF SUMMARY

Briefly stated, the invention provides compounds and methods for obtaining oligosaccharide mimics. In one aspect of the present invention, a method is provided for preparing an oligosaccharide mimic comprising incorporating at least one cyclohexane derivative into an oligosaccharide or glycomimetic compound, wherein the cyclohexane derivative has the formula:

wherein, $R^1$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; C(=O)OX, alkanyl substituted with C(=O)OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH;
$R^2$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, $C_1$-$C_8$ alkenyl, $C_1$-$C_8$ alkynyl, aryl or heteroaryl either of which may be substituted with one or more of Me, OMe, halide, or OH; —C(=O)NH(CH$_2$)$_n$NH$_2$ where n=0-30, C(=O)NHX or CX$_2$OH, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; with the proviso that $R^1$ and $R^2$ are not both H;

the cyclohexane derivative is at least attached to the oligosaccharide or glycomimetic compound at an OH, $R^1$ or $R^2$. Also included are products prepared by the method.

In another aspect of the present invention, a method is provided for substituting a monosaccharide mimic for at least one hexose or hexosamine in an oligosaccharide compound or glycomimetic compound or in an oligosaccharide or glycomimetic of an oligosaccharide-containing or glycomimetic-containing compound comprising replacing at least one hexose or hexosamine in an oligosaccharide or glycomimetic compound with a cyclohexane derivative, wherein the cyclohexane derivative has the formula:

wherein, $R^1$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; C(=O)OX, alkanyl substituted with C(=O)OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH;
$R^2$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, $C_1$-$C_8$ alkenyl, $C_1$-$C_8$ alkynyl, aryl or heteroaryl either of which may be substituted with one or more of Me, OMe, halide, or OH; —C(=O)NH(CH$_2$)$_n$NH$_2$ where n=0-30, C(=O)NHX or CX$_2$OH, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; with the proviso that $R^1$ and $R^2$ are not both H;

the cyclohexane derivative is at least attached to the oligosaccharide or glycomimetic compound at an OH, $R^1$ or $R^2$. Also included are products prepared by the method.

In another aspect, the present invention provides an oligosaccharide or glycomimetic compound that contains at least one cyclohexane derivative, wherein the cyclohexane derivative has the formula:

wherein,
  $R^1$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; C(=O)OX, alkanyl substituted with C(=O)OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH;
  $R^2$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, $C_1$-$C_8$ alkenyl, $C_1$-$C_8$ alkynyl, aryl or heteroaryl either of which may be substituted with one or more of Me, OMe, halide, or OH; —C(=O)NH(CH$_2$)$_n$NH$_2$ where n=0-30, C(=O)NHX or CX$_2$OH, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; with the proviso that $R^1$ and $R^2$ are not both H;

the cyclohexane derivative is at least attached to the oligosaccharide or glycomimetic compound at an OH, $R^1$ or $R^2$.

In another aspect, the present invention provides a compound comprising:

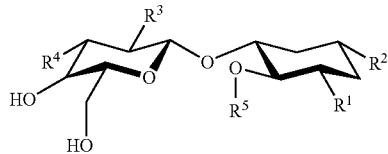

$R^1$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; C(=O)OX, alkanyl substituted with C(=O)OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH;

$R^2$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, $C_1$-$C_8$ alkenyl, $C_1$-$C_8$ alkynyl, aryl or heteroaryl either of which may be substituted with one or more of Me, OMe, halide, or OH; —C(=O)NH(CH$_2$)$_n$NH$_2$ where n=0-30, C(=O)NHX or CX$_2$OH, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; with the proviso that $R^1$ and $R^2$ are not both H;

$R^3$=—OH,

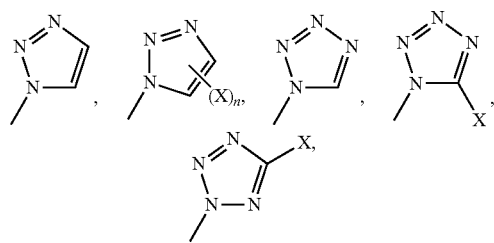

—O—C(=O)—X, —NH$_2$, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl,

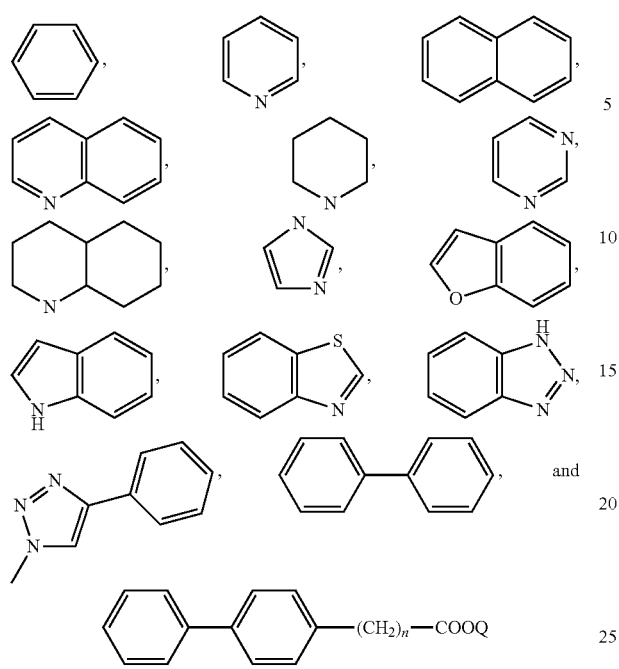

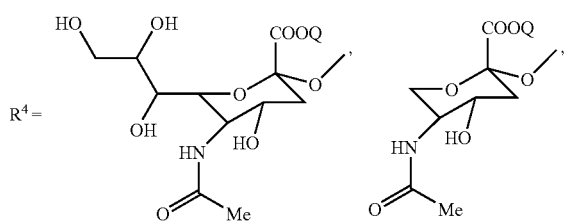

6'sulfated GlcNAc, 6'carboxylated GlcNAc, 6'sulfated GalNAc, 6'sulfated galactose, 6'carboxylated galactose,

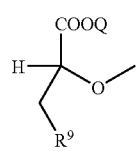

where Q is H or a physiologically acceptable salt or
C$_1$-C$_8$ alkanyl, C$_1$-C$_8$ alkenyl, C$_1$-C$_8$ alkynyl, aryl, heteroaryl, (CH$_2$)$_n$-aryl or (CH$_2$)$_n$-heteroaryl where n is 1-10, and where R$^9$ is aryl, heteroaryl, cyclohexane, t-butane, adamantane, or triazole, and any of R$^9$ may be substituted with one to three independently selected of Cl, F, CF$_3$, C$_1$-C$_8$ alkoxy, NO$_2$, C$_1$-C$_8$ alkanyl, C$_1$-C$_8$ alkenyl, C$_1$-C$_8$ alkynyl or OY, C(=O)OY, NY$_2$ or C(=O)NHY where Y is H, C$_1$-C$_8$ alkanyl, C$_1$-C$_8$ alkenyl, C$_1$-C$_8$ alkynyl or C$_1$-C$_{14}$ aryl; or

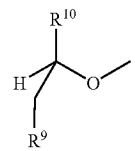

where R$^{10}$ is one of

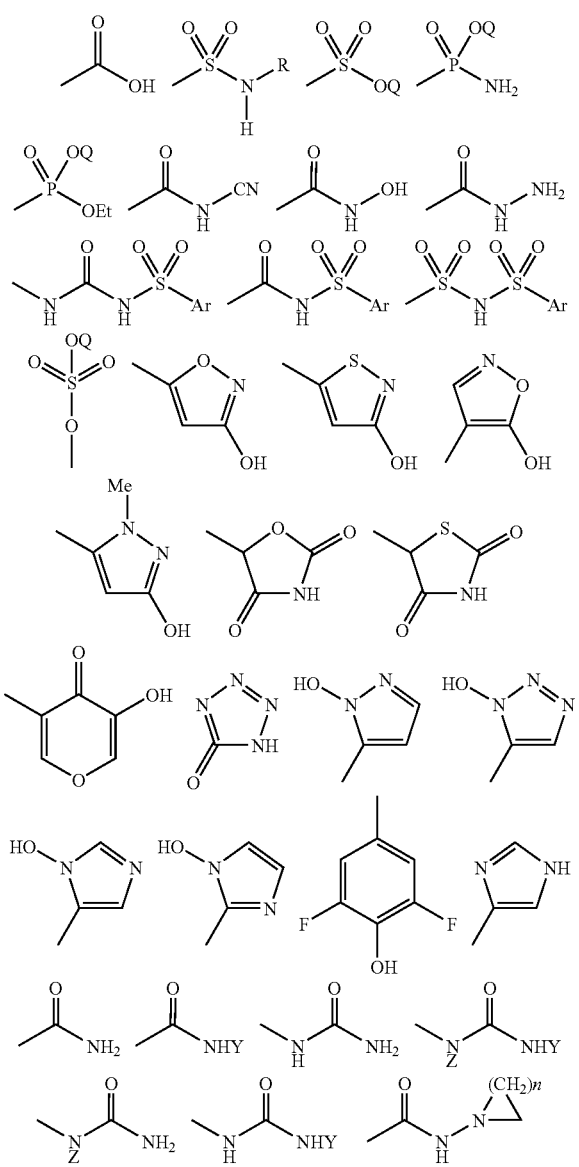

where Q is H or a physiologically acceptable salt, C$_1$-C$_8$ alkanyl, C$_1$-C$_8$ alkenyl, C$_1$-C$_8$ alkynyl, aryl, heteroaryl, (CH$_2$)$_m$-aryl or (CH$_2$)$_m$-heteroaryl where m is 1-10, n=1-4, Z and Y=C$_1$-C$_8$ alkanyl, C$_1$-C$_8$ alkenyl, C$_1$-C$_8$ alkynyl, halogenated C$_1$-C$_8$ alkanyl, aryl and heteroaryl substituted with Me, OMe, halide, OH; and $R^5$=H, D-mannose, L-galactose, D-arabinose, L-fucose, polyols,

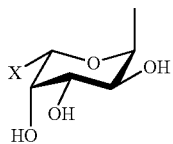

where X=$CF_3$, cyclopropyl or $C_1$-$C_8$ alkanyl,
$C_1$-$C_8$ alkenyl, $C_1$-$C_8$ alkynyl, aryl, heteroaryl, $(CH_2)_m$-aryl or $(CH_2)_m$-heteroaryl where m is 1-10, or

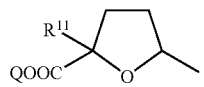

where Q is H or a physiologically acceptable salt,
$C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where $R^{11}$ is aryl, heteroaryl,

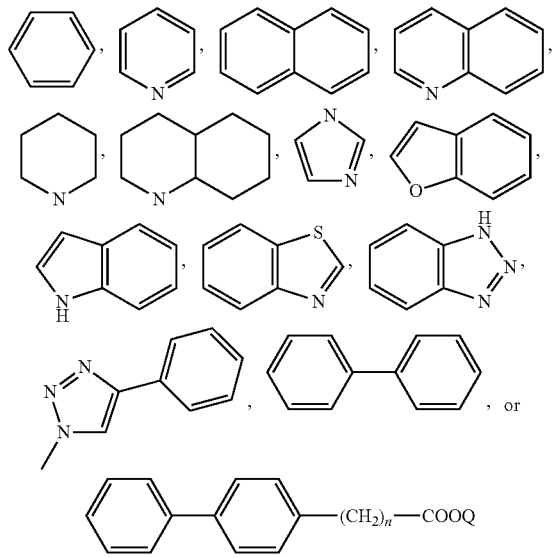

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where n=0-10, and any one of the above ring compounds may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl or $C_1$-$C_8$ alkynyl.

The compound may include a polyethylene glycol attached thereto. Alternatively, multimers may be formed whereby the compound is attached to another of the compound by polyethylene glycol. As used herein, "another of the compound" refers to either a second compound identical to the first compound, or a second compound that is encompassed by the disclosure herein but not identical to the first compound.

In another aspect, the present invention provides a compound consisting of:

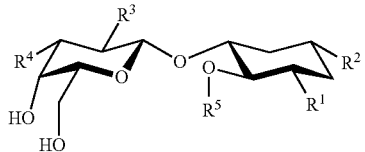

$R^1$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; C(=O)OX, alkanyl substituted with C(=O)OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH;

$R^2$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, $C_1$-$C_8$ alkenyl, $C_1$-$C_8$ alkynyl, aryl or heteroaryl either of which may be substituted with one or more of Me, OMe, halide, or OH; —C(=O)NH$(CH_2)_n$$NH_2$ where n=0-30, C(=O)NHX or $CX_2$OH, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; with the proviso that $R^1$ and $R^2$ are not both H;

$R^3$=—OH,

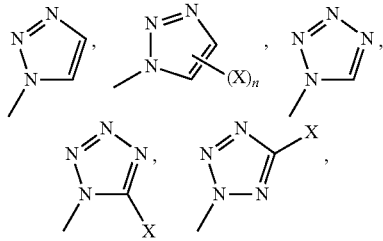

—O—C(=O)—X, —$NH_2$, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl,

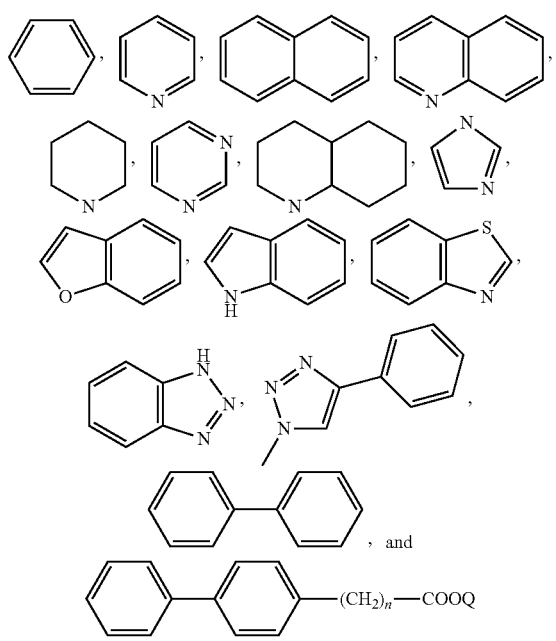

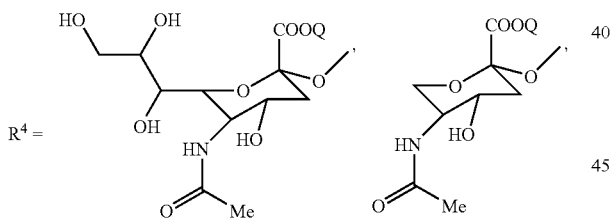

6'sulfated GlcNAc, 6'carboxylated GlcNAc, 6'sulfated GalNAc, 6'sulfated galactose, 6'carboxylated galactose,

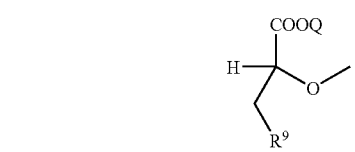

where Q is H or a physiologically acceptable salt or
C$_1$-C$_8$ alkanyl, C$_1$-C$_8$ alkenyl, C$_1$-C$_8$ alkynyl, aryl, heteroaryl, (CH$_2$)$_n$-aryl or (CH$_2$)$_n$-heteroaryl where n is 1-10, and where R$^9$ is aryl, heteroaryl, cyclohexane, t-butane, adamantane, or triazole, and any of R$^9$ may be substituted with one to three independently selected of Cl, F, CF$_3$, C$_1$-C$_8$ alkoxy, NO$_2$, C$_1$-C$_8$ alkanyl, C$_1$-C$_8$ alkenyl, C$_1$-C$_8$ alkynyl or OY, C(=O)OY, NY$_2$ or C(=O)NHY where Y is H, C$_1$-C$_8$ alkanyl, C$_1$-C$_8$ alkenyl, C$_1$-C$_8$ alkynyl or C$_1$-C$_{14}$ aryl; or

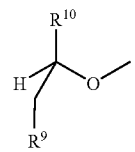

where R$^{10}$ is one of

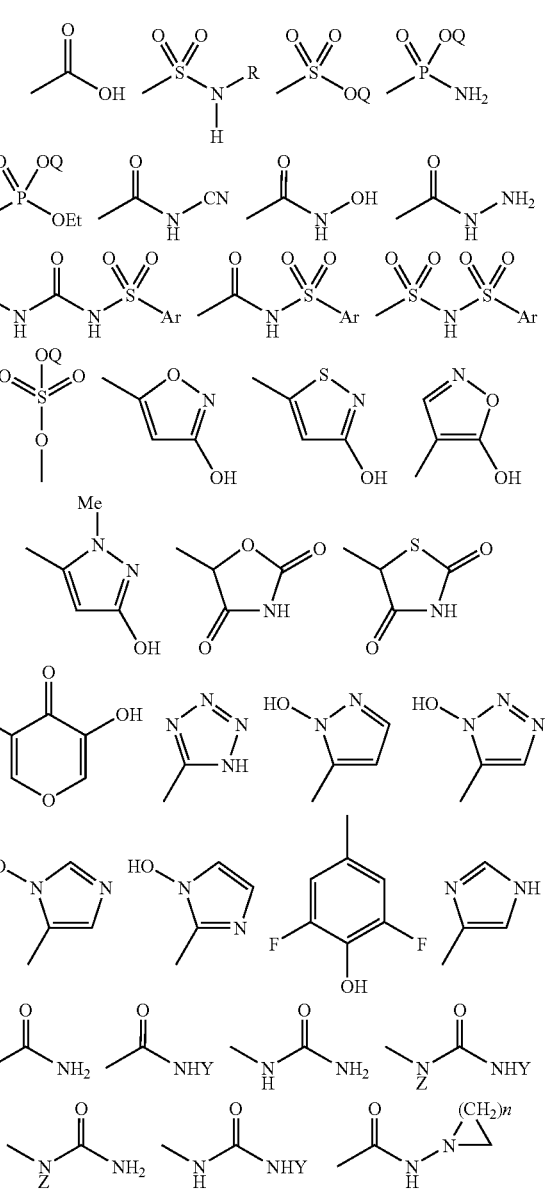

where Q is H or a physiologically acceptable salt, C$_1$-C$_8$ alkanyl, C$_1$-C$_8$ alkenyl, C$_1$-C$_8$ alkynyl, aryl, heteroaryl, (CH$_2$)$_m$-aryl or (CH$_2$)$_m$-heteroaryl where m is 1-10, n=1-4, Z and Y=C$_1$-C$_8$ alkanyl, C$_1$-C$_8$ alkenyl, C$_1$-C$_8$ alkynyl, halogenated C$_1$-C$_8$ alkanyl, aryl and heteroaryl substituted with Me, OMe, halide, OH; and $R^5$=H, D-mannose, L-galactose, D-arabinose, L-fucose, polyols,

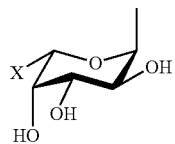

where X=$CF_3$, cyclopropyl or $C_1$-$C_8$ alkanyl,
$C_1$-$C_8$ alkenyl, $C_1$-$C_8$ alkynyl, aryl, heteroaryl, $(CH_2)_m$-aryl or $(CH_2)_m$-heteroaryl where m is 1-10, or

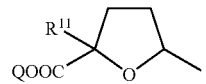

where Q is H or a physiologically acceptable salt,
$C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where $R^{11}$ is aryl, heteroaryl,

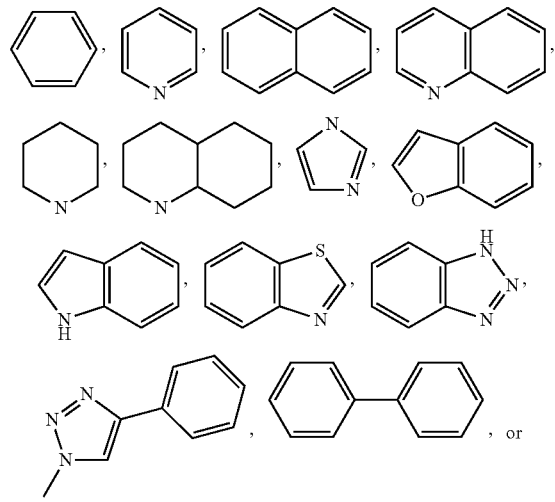

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where n=0-10, and any one of the above ring compounds may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl or $C_1$-$C_8$ alkynyl.

The compound may include a polyethylene glycol attached thereto. Alternatively, multimers may be formed whereby the compound is attached to another of the compound by polyethylene glycol.

In an embodiment, the present invention provides a compound having the formula:

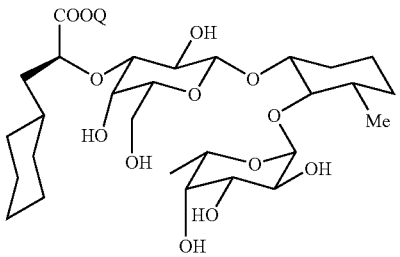

where Q is H or a physiologically acceptable salt, and Me is methyl. The compound may include a polyethylene glycol attached thereto. Alternatively, multimers may be formed whereby the compound is attached to another of the compound by polyethylene glycol.

In an embodiment, the present invention provides a compound having the formula:

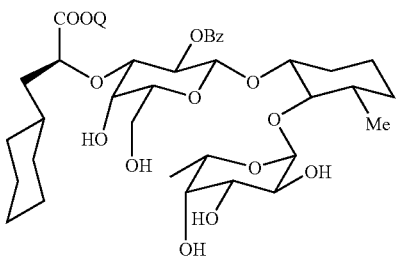

where Q is H or a physiologically acceptable salt, Me is methyl and Bz is benzoyl. The compound may include a polyethylene glycol attached thereto. Alternatively, multimers may be formed whereby the compound is attached to another of the compound by polyethylene glycol.

In an embodiment, the present invention provides a compound having the formula:

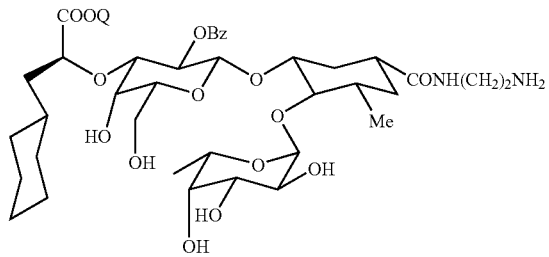

where Q is H or a physiologically acceptable salt, Me is methyl and Bz is benzoyl.

The compound may include a polyethylene glycol attached thereto. Alternatively, multimers may be formed whereby the compound is attached to another of the compound by polyethylene glycol.

In an embodiment, the present invention provides a compound having the formula:

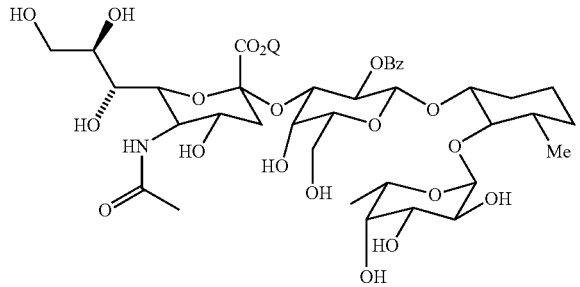

where Q is H or a physiologically acceptable salt, Me is methyl and Bz is benzoyl. The compound may include a polyethylene glycol attached thereto. Alternatively, multimers may be formed whereby the compound is attached to another of the compound by polyethylene glycol.

In an embodiment, the present invention provides a compound having the formula:

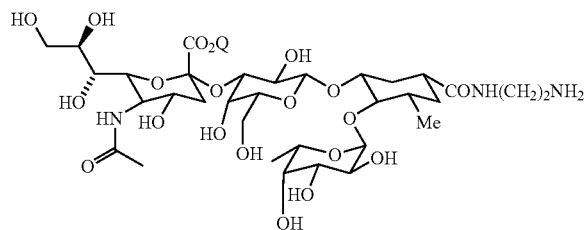

where Q is H or a physiologically acceptable salt, and Me is methyl. The compound may include a polyethylene glycol attached thereto. Alternatively, multimers may be formed whereby the compound is attached to another of the compound by polyethylene glycol.

In an embodiment, the present invention provides a compound having the formula:

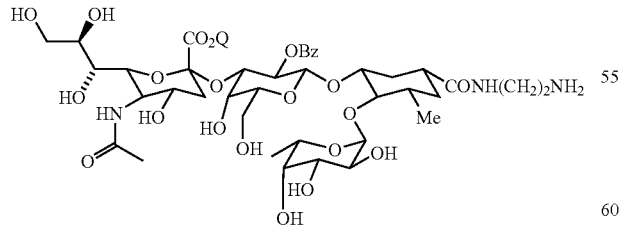

where Q is H or a physiologically acceptable salt, Me is methyl and Bz is benzoyl. The compound may include a polyethylene glycol attached thereto. Alternatively, multimers may be formed whereby the compound is attached to another of the compound by polyethylene glycol.

In an embodiment, the present invention provides a compound having the formula:

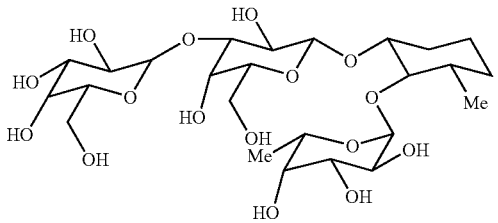

where Me is methyl. The compound may include a polyethylene glycol attached thereto. Alternatively, multimers may be formed whereby the compound is attached to another of the compound by polyethylene glycol.

In an embodiment, the present invention provides a compound having the formula:

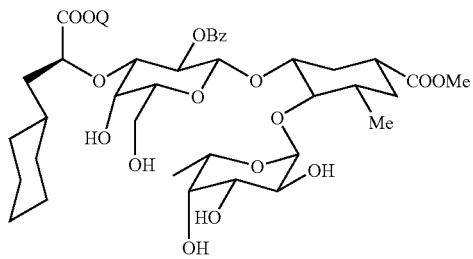

where Q is H or a physiologically acceptable salt, Me is methyl and Bz is benzoyl. The compound may include a polyethylene glycol attached thereto. Alternatively, multimers may be formed whereby the compound is attached to another of the compound by polyethylene glycol.

In an embodiment, the present invention provides a compound having the formula:

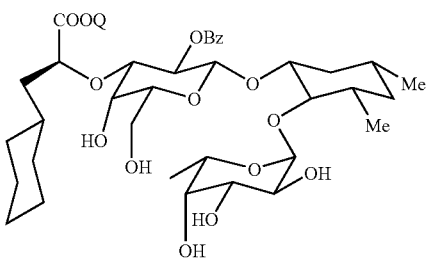

where Q is H or a physiologically acceptable salt, Me is methyl and Bz is benzoyl. The compound may include a polyethylene glycol attached thereto. Alternatively, multimers may be formed whereby the compound is attached to another of the compound by polyethylene glycol.

In an embodiment, the present invention provides a compound having the formula:

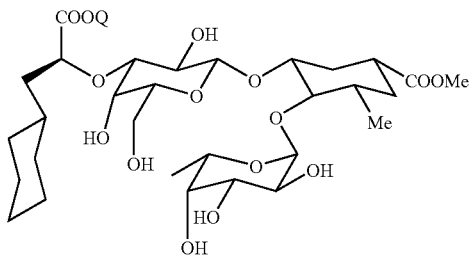

where Q is H or a physiologically acceptable salt, and Me is methyl. The compound may include a polyethylene glycol attached thereto. Alternatively, multimers may be formed whereby the compound is attached to another of the compound by polyethylene glycol.

In an embodiment, the present invention provides a compound having the formula:

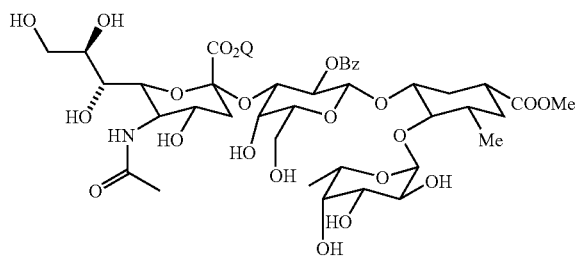

where Q is H or a physiologically acceptable salt, Me is methyl and Bz is benzoyl. The compound may include a polyethylene glycol attached thereto. Alternatively, multimers may be formed whereby the compound is attached to another of the compound by polyethylene glycol.

In an embodiment, the present invention provides a compound having the formula:

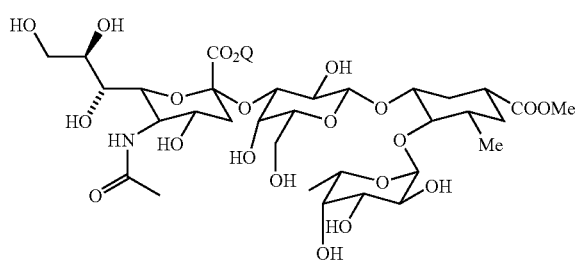

where Q is H or a physiologically acceptable salt, and Me is methyl. The compound may include a polyethylene glycol attached thereto. Alternatively, multimers may be formed whereby the compound is attached to another of the compound by polyethylene glycol.

In an embodiment, the present invention provides a compound having the formula:

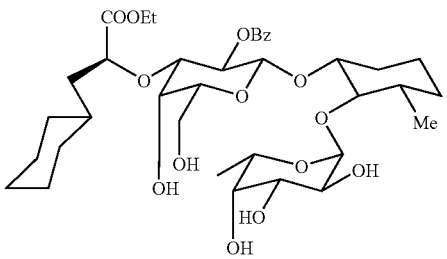

where Me is methyl, Et is ethyl, and Bz in benzoyl. The compound may include a polyethylene glycol attached thereto. Alternatively, multimers may be formed whereby the compound is attached to another of the compound by polyethylene glycol.

In an embodiment, the present invention provides a compound having the formula:

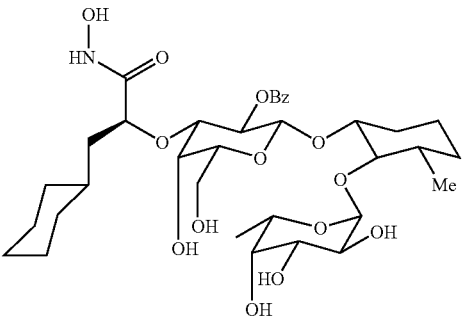

where Me is methyl and Bz in benzoyl. The compound may include a polyethylene glycol attached thereto. Alternatively, multimers may be formed whereby the compound is attached to another of the compound by polyethylene glycol.

In an embodiment, the present invention provides a compound having the formula:

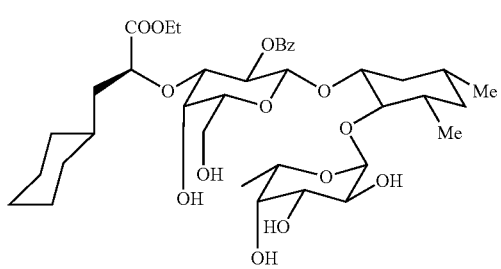

where Me is methyl, Et is ethyl and Bz is benzoyl. The compound may include a polyethylene glycol attached thereto. Alternatively, multimers may be formed whereby the compound is attached to another of the compound by polyethylene glycol.

In an embodiment, the present invention provides a compound having the formula:

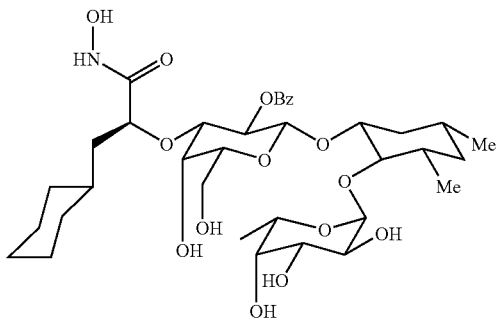

where Me is methyl and Bz is benzoyl. The compound may include a polyethylene glycol attached thereto. Alternatively, multimers may be formed whereby the compound is attached to another of the compound by polyethylene glycol.

These and other aspects of the present invention will become apparent upon reference to the following detailed description and attached drawings. All references disclosed herein are hereby incorporated by reference in their entirety as if each was incorporated individually.

DETAILED DESCRIPTION

Figure 1:
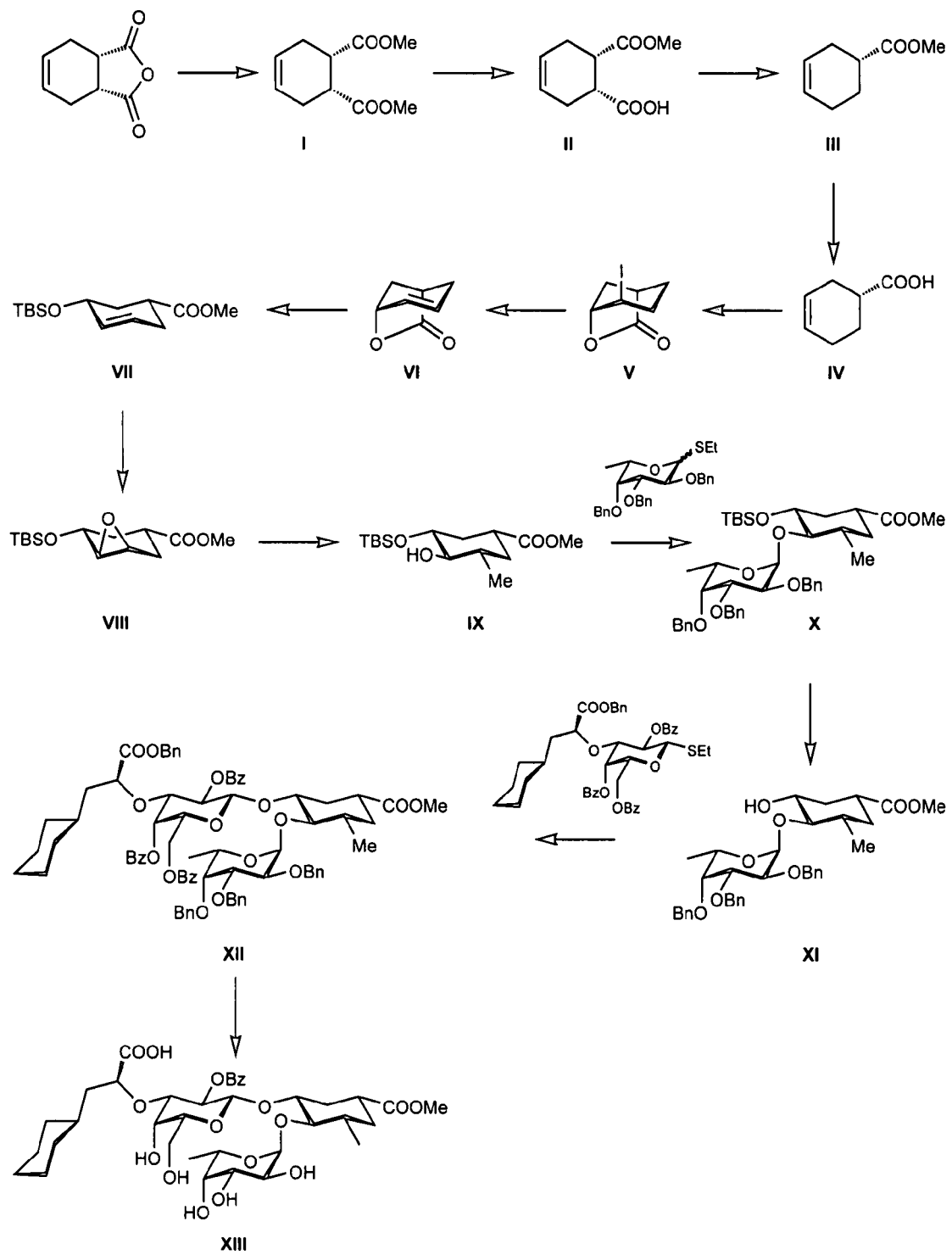
FIG. 1 is a diagram illustrating the synthesis of GlcNAc mimics from tetrahydrophthalic anhydride.

As noted above, the present invention provides compounds and methods for obtaining monosaccharide and oligosaccharide mimics. Such mimics have a variety of uses in vitro and in vivo, including as antagonists of E-selectin.

Within the present invention, an oligosaccharide mimic may be prepared by incorporating one or more cyclohexane derivatives into an oligosaccharide or glycomimetic compound. An oligosaccharide refers to two or more monosaccharides covalently joined. Oligosaccharides are polymers containing monosaccharide units, typically with 2 to about 100 monosaccharides and any integer in-between. Each monosaccharide of an oligosaccharide is independently selected; although two or more monosaccharides may be identical.

The cyclohexane derivative of the methods of the present invention has the formula:

$R^1$ may be H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; C(=O)OX, alkanyl substituted with C(=O) OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH. $R^2$ may be H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, $C_1$-$C_8$ alkenyl, $C_1$-$C_8$ alkynyl, aryl or heteroaryl either of which may be substituted with one or more of Me, OMe, halide, or OH; —C(=O)NH(CH$_2$)$_n$NH$_2$ where n=0-30, C(=O)NHX or CX$_2$OH, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; with the proviso that $R^1$ and $R^2$ are not both H. The cyclohexane derivative is attached to the oligosaccharide or glycomimetic compound at least at one of the OH, the $R^1$ or the $R^2$. In embodiments, attachment is at least at one of the OH or the $R^2$. Other options for attachment include at both of the OH, e.g., one monosaccharide or monosaccharide mimic attached at one of the OH and another monosaccharide or monosaccharide mimic attached at the other OH.

Such a cyclohexane derivative may also be used in a method for substituting a monosaccharide mimic (a cyclohexane derivative) for at least one hexose or hexosamine. The hexose or hexosamine may be in an oligosaccharide or glycomimetic compound or in an oligosaccharide or glycomimetic possessed by an oligosaccharide-containing or glycomimetic-containing compound. Such a substitution is accomplished by replacing one or more hexose or hexosamine in an oligosaccharide or glycomimetic compound with a cyclohexane derivative. If it is more than one, then each is independently selected. Examples of oligosaccharide-containing compounds include glycoproteins, glycopeptides, glycolipids and glyconucleic acids.

As used herein, a "$C_1$-$C_8$ alkanyl" refers to an alkane substituent with one to eight carbon atoms and may be straight chain, branched or cyclic (cycloalkanyl). Examples are methyl, ethyl, propyl, isopropyl, butyl and t-butyl. A "halogenated $C_1$-$C_8$ alkanyl" refers to a "$C_1$-$C_8$ alkanyl" possessing at least one halogen. Where there is more than one halogen present, the halogens present may be the same or different or both (if at least three present). A "$C_1$-$C_8$ alkenyl" refers to an alkene substituent with one to eight carbon atoms, at least one carbon-carbon double bond, and may be straight chain, branched or cyclic (cycloalkenyl). Examples are similar to "$C_1$-$C_8$ alkanyl" examples except possessing at least one carbon-carbon double bond. A "$C_1$-$C_8$ alkynyl" refers to an alkyne substituent with one to eight carbon atoms, at least one carbon-carbon triple bond, and may be straight chain, branched or cyclic (cycloalkynyl). Examples are similar to "$C_1$-$C_8$ alkanyl" examples except possessing at least one carbon-carbon triple bond. An "alkoxy" refers to an oxygen substituent possessing a "$C_1$-$C_8$ alkanyl," "$C_1$-$C_8$ alkenyl" or "$C_1$-$C_8$ alkynyl." This is —O-alkyl; for example methoxy, ethoxy, n-propoxy, i-propoxy, n-butoxy and the like; and alkenyl or alkynyl variations thereof (except for methoxy). It further refers to the group O-alkyl-W-alkyl where W is O or N; for example —O—$(CH_2)_n$—W—$(CH_2)_m$ where n and m are independently 1-10. An "aryl" refers to an aromatic substituent with one to fourteen carbon atoms in one or multiple rings which may be separated by a bond or fused. A "heteroaryl" is similar to an "aryl" except the aromatic substituent possesses at least one heteroatom (such as N, O or S) in place of a ring carbon. Examples of aryls and heteroaryls include phenyl, naphthyl, pyridinyl, pyrimidinyl, triazolo, furanyl, oxazolyl, thiophenyl, quinolinyl and diphenyl. As used herein, the term "independently selected" refers to the selection of identical or different substituents. "Me" and "Et" represent methyl and ethyl, respectively. "Bz" represents benzoyl. "Ar" represents aryl. Examples of physiologically acceptable salts include Na, K, Li, Mg and Ca. Monosaccharide substituents recited herein (e.g., D-mannose, L-galactose, D-arabinose and L-fucose) may be in the furanose, pyranose or open form.

A linker arm may be desirable for attachment, for example, to a monosaccharide, a monosaccharide mimic or something else such as an amino acid, nucleic acid or lipid. A linker may include a spacer group, such as —$(CH_2)_n$— or —$O(CH_2)_n$— where n is generally about 1-20 (all number ranges disclosed herein include any whole integer range therein). An example of a linker is —$NH_2$, e.g., —$CH_2$—$NH_2$ when it includes a short spacer group.

Embodiments of linkers include the following:

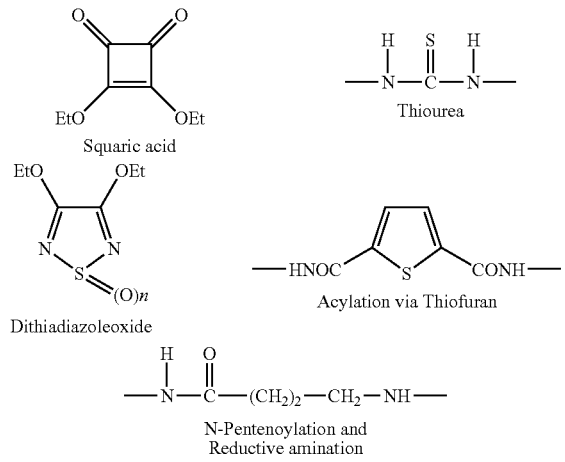

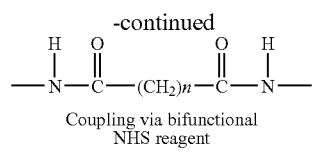

Other linkers with or without a spacer group (e.g., CONH$(CH_2)_2NH_2$, COOMe, or polyethylene glycol or derivative) will be familiar to those in the art or in possession of the present disclosure.

Alternatively, or in combination with a linker arm, a cyclohexane derivative may be attached at one or both OH.

The methods of the present invention provide for a variety of compounds. For example, in one embodiment is provided an oligosaccharide or glycomimetic compound that contains at least one cyclohexane derivative, wherein the cyclohexane derivative has the formula:

wherein,
$R^1$ is defined as above;
$R^2$ is defined as above; and
the cyclohexane derivative is at least attached to the oligosaccharide or glycomimetic compound at an OH, $R^1$ or $R^2$.

In another embodiment is provided a compound comprising:

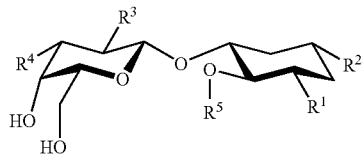

$R^1$ of the formula may be H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; C(=O)OX, alkanyl substituted with C(=O)OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH;

$R^2$ of the formula may be H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, $C_1$-$C_8$ alkenyl, $C_1$-$C_8$ alkynyl, aryl or heteroaryl either of which may be substituted with one or more of Me, OMe, halide, or OH; —C(=O)NH(CH$_2$)$_n$NH$_2$ where n=0-30, C(=O)NHX or CX$_2$OH, where X=C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; O(=O)X, OX, NHX, NH(=O)X, where X=H, C$_1$-C$_8$ alkanyl, C$_1$-C$_8$ alkenyl, C$_1$-C$_8$ alkynyl, halogenated C$_1$-C$_8$ alkanyl, aryl or heteroaryl either of which may be substituted with one or more of Me, OMe, halide, or OH; with the proviso that R$^1$ and R$^2$ are not both H;

R$^3$ of the formula may be —OH,

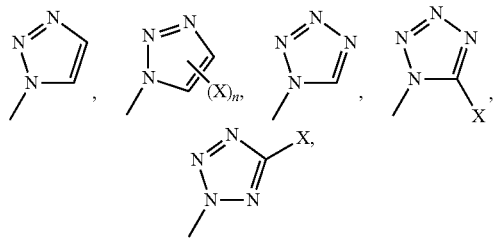

—O—C(=O)—X, —NH$_2$, —NH—C(=O)—NHX, or —NH—C(=O)—X where n=0-2 and X is independently selected from C$_1$-C$_8$ alkanyl, C$_1$-C$_8$ alkenyl, C$_1$-C$_8$ alkynyl,

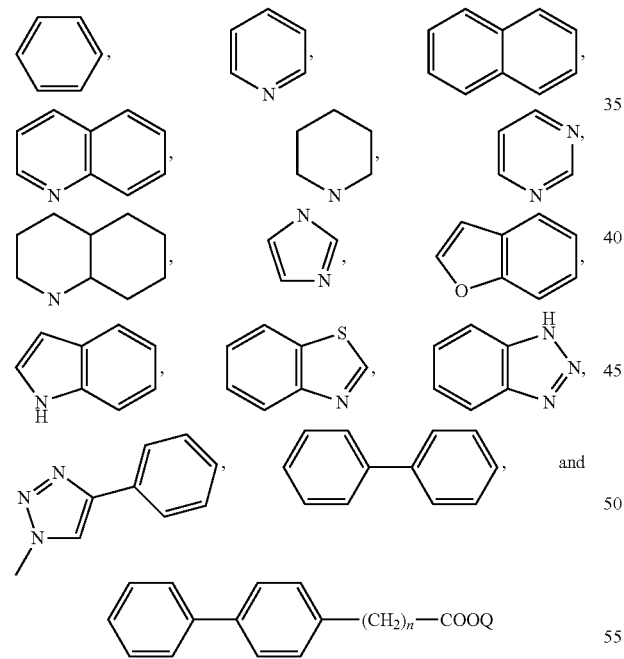

where Q is H or a physiologically acceptable salt, C$_1$-C$_8$ alkanyl, C$_1$-C$_8$ alkenyl, C$_1$-C$_8$ alkynyl, aryl, heteroaryl, (CH$_2$)$_m$-aryl or (CH$_2$)$_m$-heteroaryl where m is 1-10, and where n=0-10, and any of the above ring compounds may be substituted with one to three independently selected of Cl, F, CF$_3$, C$_1$-C$_8$ alkoxy, NO$_2$, C$_1$-C$_8$ alkanyl, C$_1$-C$_8$ alkenyl, C$_1$-C$_8$ alkynyl, C$_1$-C$_{14}$ aryl, or OY, C(=O)OY, NY$_2$ or C(=O)NHY where Y is H, C$_1$-C$_8$ alkanyl, C$_1$-C$_8$ alkenyl, C$_1$-C$_8$ alkynyl, or C$_1$-C$_{14}$ aryl;

R$^4$ of the formula may be

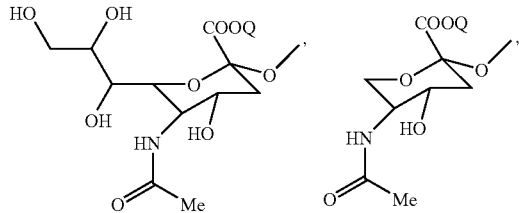

6'sulfated GlcNAc, 6'carboxylated GlcNAc, 6'sulfated GalNAc, 6'sulfated galactose, 6'carboxylated galactose,

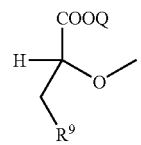

where Q is H or a physiologically acceptable salt or C$_1$-C$_8$ alkanyl, C$_1$-C$_8$ alkenyl, C$_1$-C$_8$ alkynyl, aryl, heteroaryl, (CH$_2$)$_n$-aryl or (CH$_2$)$_n$-heteroaryl where n is 1-10, and where R$^9$ is aryl, heteroaryl, cyclohexane, t-butane, adamantane, or triazole, and any of R$^9$ may be substituted with one to three independently selected of Cl, F, CF$_3$, C$_1$-C$_8$ alkoxy, NO$_2$, C$_1$-C$_8$ alkanyl, C$_1$-C$_8$ alkenyl, C$_1$-C$_8$ alkynyl or OY, C(=O)OY, NY$_2$ or C(=O)NHY where Y is H, C$_1$-C$_8$ alkanyl, C$_1$-C$_8$ alkenyl, C$_1$-C$_8$ alkynyl or C$_1$-C$_{14}$ aryl; or

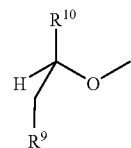

where R$^{10}$ is one of

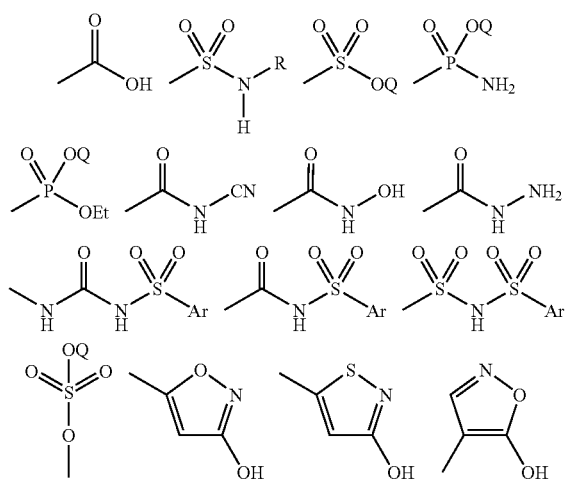

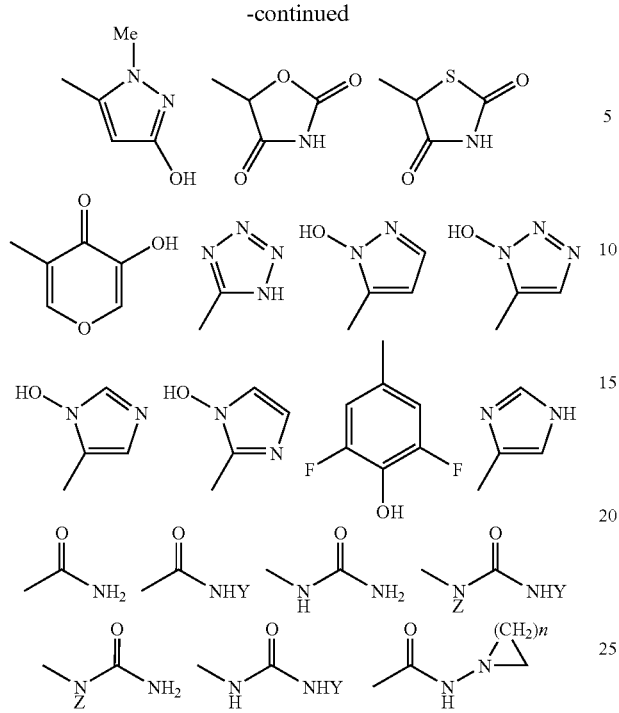

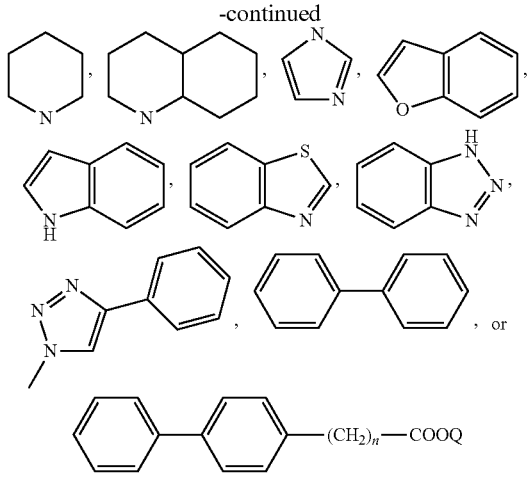

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where n=0-10, and any one of the above ring compounds may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl or $C_1$-$C_8$ alkynyl.

In another embodiment is provided a compound consisting of:

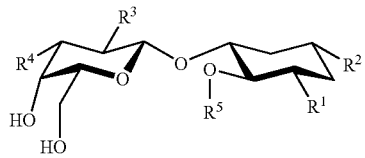

$R^1$ is H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; C(=O)OX, alkanyl substituted with C(=O)OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH;

$R^2$ is H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, $C_1$-$C_8$ alkenyl, $C_1$-$C_8$ alkynyl, aryl or heteroaryl either of which may be substituted with one or more of Me, OMe, halide, or OH; —C(=O)NH$(CH_2)_n$NH$_2$ where n=0-30, C(=O)NHX or CX$_2$OH, where X=$C_1$-$C_8$ alkanyl, $C_1$-$C_8$ alkenyl, $C_1$-$C_8$ alkynyl, where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, n=1-4, Z and Y=$C_1$-$C_8$ alkanyl, $C_1$-$C_8$ alkenyl, $C_1$-$C_8$ alkynyl, halogenated $C_1$-$C_8$ alkanyl, aryl and heteroaryl substituted with Me, OMe, halide, OH; and $R^5$ of the formula may be H. D-mannose, L-galactose, D-arabinose, polyols, L-fucose,

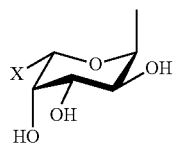

where X=$CF_3$, cyclopropyl or $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, or

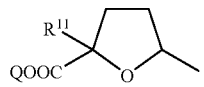

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where $R^{11}$ is aryl, heteroaryl,

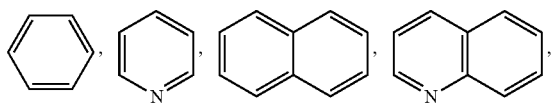

halogenated $C_1$-$C_8$ alkanyl, aryl or heteroaryl either of which may be substituted with one or more of Me, OMe, halide, or OH; O(=O)X, OX, NHX, NH(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; with the proviso that $R^1$ and $R^2$ are not both H;

$R^3$ is —OH,

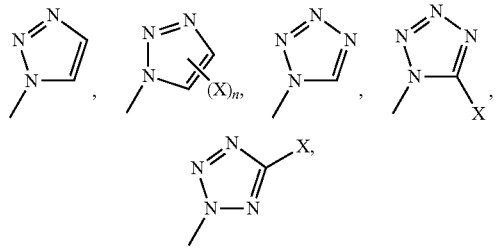

—O—C(=O)—X, —NH$_2$, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl,

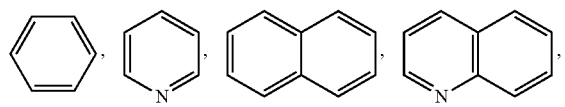

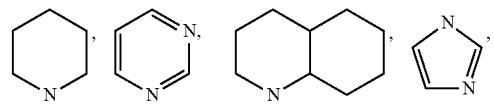

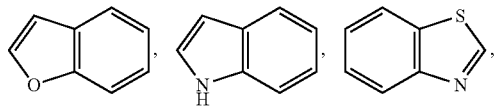

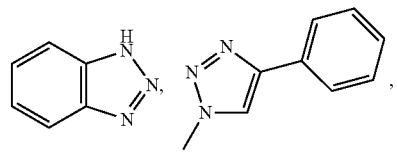

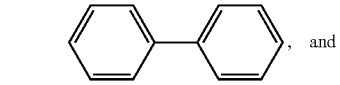

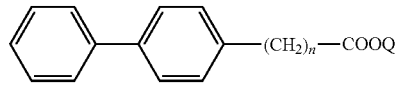

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where n=0-10, and any of the above ring compounds may be substituted with one to three independently selected of Cl, F, $CF_3$, $C_1$-$C_8$ alkoxy, $NO_2$, $C_1$-$C_8$ alkanyl, $C_1$-$C_8$ alkenyl, $C_1$-$C_8$ alkynyl, $C_1$-$C_{14}$ aryl, or OY, C(=O)OY, $NY_2$ or C(=O)NHY where Y is H, $C_1$-$C_8$ alkanyl, $C_1$-$C_8$ alkenyl, $C_1$-$C_8$ alkynyl, or $C_1$-$C_{14}$ aryl;

$R^4$ is 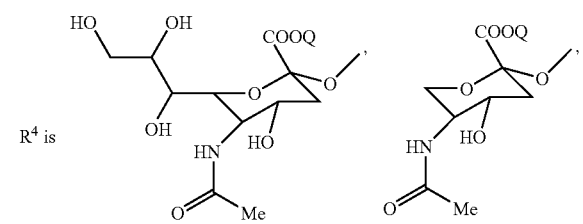

6'sulfated GlcNAc, 6'carboxylated GlcNAc, 6'sulfated GalNAc, 6'sulfated galactose, 6'carboxylated galactose,

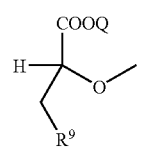

where Q is H or a physiologically acceptable salt or $C_1$-$C_8$ alkanyl, $C_1$-$C_8$ alkenyl, $C_1$-$C_8$ alkynyl, aryl, heteroaryl, $(CH_2)_n$-aryl or $(CH_2)_n$-heteroaryl where n is 1-10, and where $R^9$ is aryl, heteroaryl, cyclohexane, t-butane, adamantane, or triazole, and any of $R^9$ may be substituted with one to three independently selected of Cl, F, $CF_3$, $C_1$-$C_8$ alkoxy, $NO_2$, $C_1$-$C_8$ alkanyl, $C_1$-$C_8$ alkenyl, $C_1$-$C_8$ alkynyl or OY, C(=O)OY, $NY_2$ or C(=O)NHY where Y is H, $C_1$-$C_8$ alkanyl, $C_1$-$C_8$ alkenyl, $C_1$-$C_8$ alkynyl or $C_1$-$C_{14}$ aryl; or

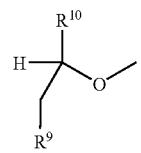

where $R^{10}$ is one of

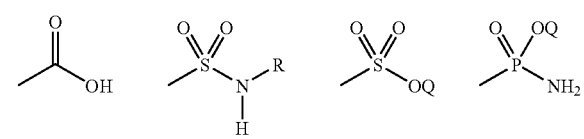

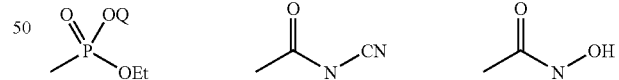

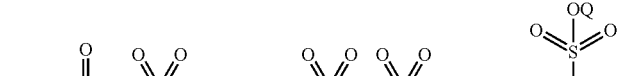

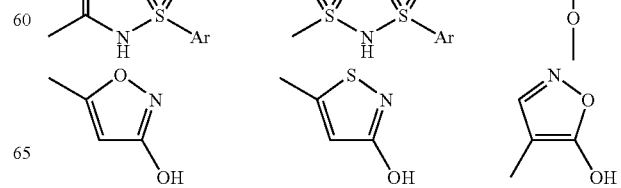

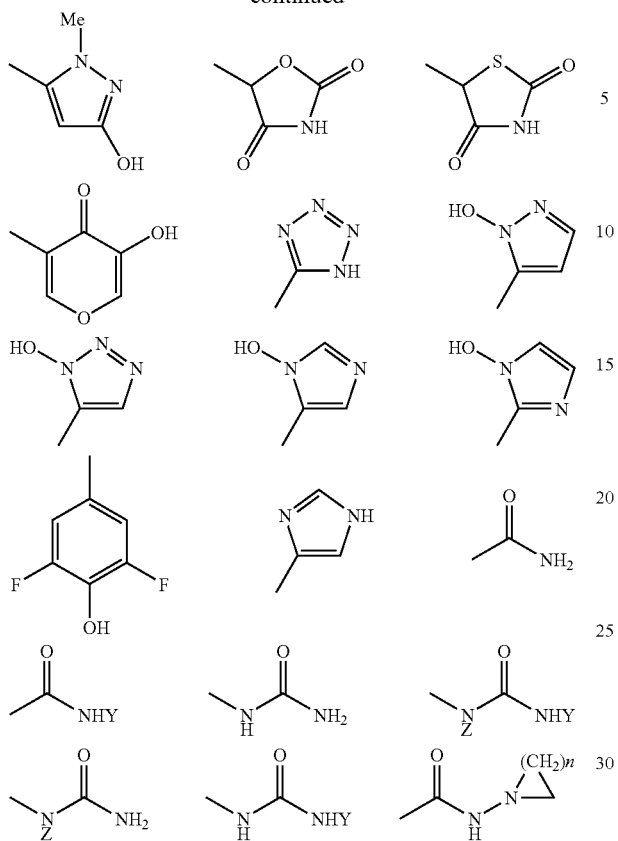

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, n=1-4, Z and Y=$C_1$-$C_8$ alkanyl, $C_1$-$C_8$ alkenyl, $C_1$-$C_8$ alkynyl, halogenated $C_1$-$C_8$ alkanyl, aryl and heteroaryl substituted with Me, OMe, halide, OH; and $R^5$ is H, D-mannose, L-galactose, D-arabinose, L-fucose, polyols,

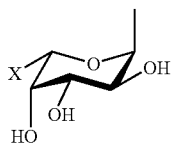

where X=$CF_3$, cyclopropyl or $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, or

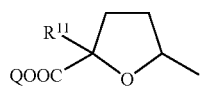

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where $R^{11}$ is aryl, heteroaryl,

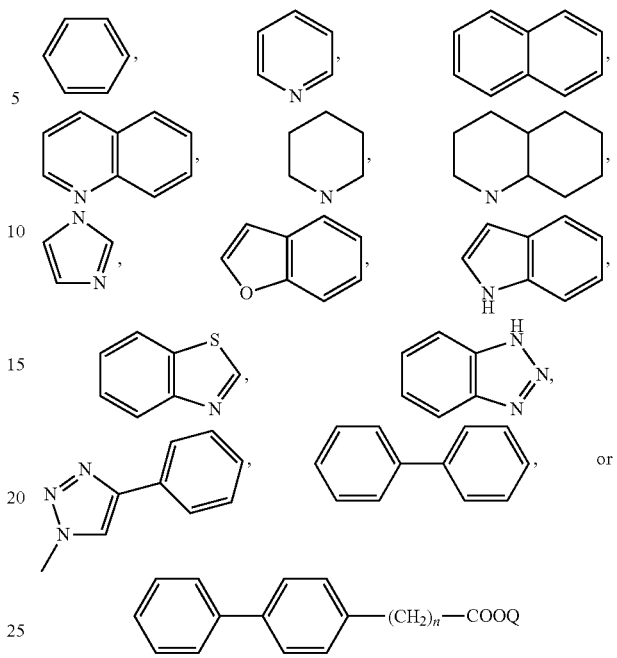

where Q is H or a physiologically acceptable salt, $C_1$-$C_8$ alkanyl, $C_1$-$C_8$ alkenyl, $C_1$-$C_8$ alkynyl, aryl, heteroaryl, $(CH_2)_m$-aryl or $(CH_2)_m$-heteroaryl where m is 1-10, and where n=0-10, and any one of the above ring compounds may be substituted with one to three independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl or $C_1$-$C_8$ alkynyl.

In another embodiment is provided a compound having the formula:

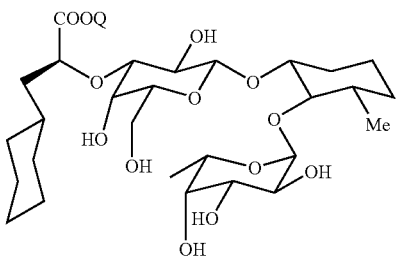

where Q is H or a physiologically acceptable salt, and Me is methyl.

In another embodiment is provided a compound having the formula:

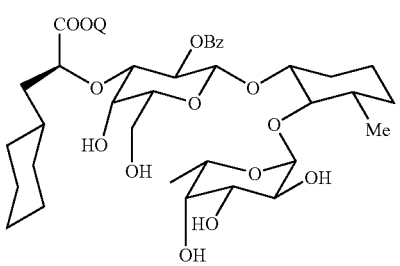

where Q is H or a physiologically acceptable salt, Me is methyl and Bz is benzoyl.

In another embodiment is provided a compound having the formula:

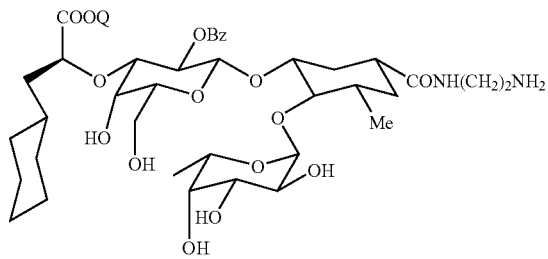

where Q is H or a physiologically acceptable salt, Me is methyl and Bz is benzoyl.

In another embodiment is provided a compound having the formula:

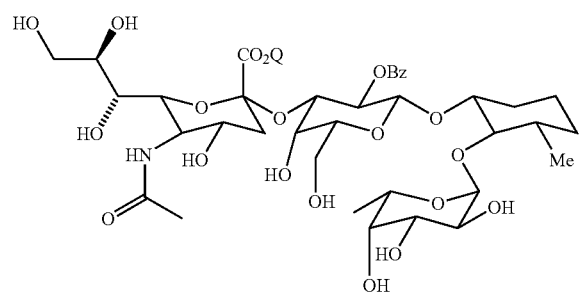

where Q is H or a physiologically acceptable salt, Me is methyl and Bz is benzoyl.

In another embodiment is provided a compound having the formula:

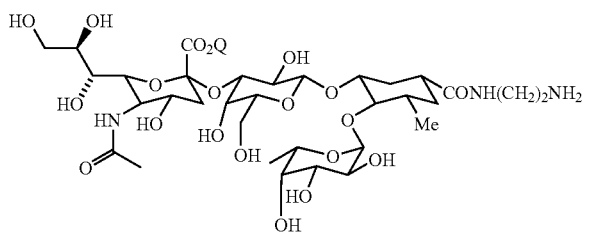

where Q is H or a physiologically acceptable salt, and Me is methyl.

In another embodiment is provided a compound having the formula:

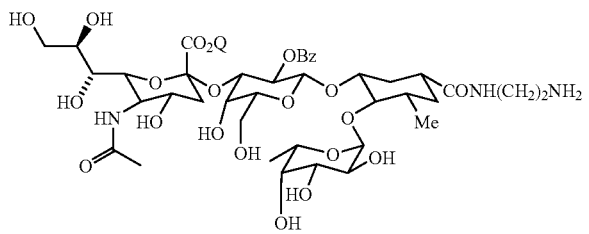

where Q is H or a physiologically acceptable salt, Me is methyl and Bz is benzoyl.

In another embodiment is provided a compound having the formula:

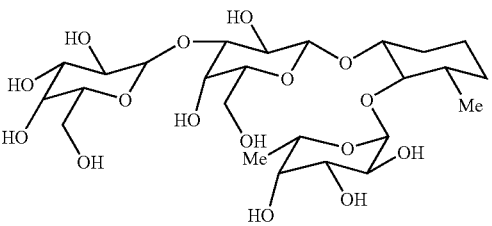

where Me is methyl.

In an embodiment, the present invention provides a compound having the formula:

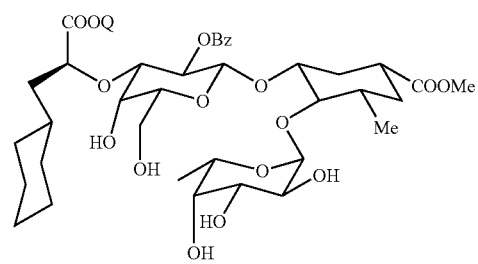

where Q is H or a physiologically acceptable salt, Me is methyl and Bz is benzoyl.

In an embodiment, the present invention provides a compound having the formula:

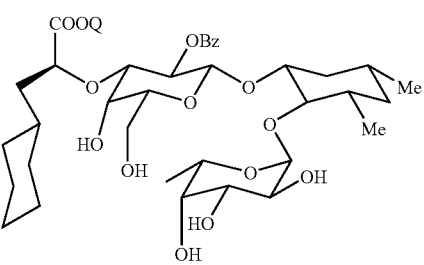

where Q is H or a physiologically acceptable salt, Me is methyl and Bz is benzoyl.

In an embodiment, the present invention provides a compound having the formula:

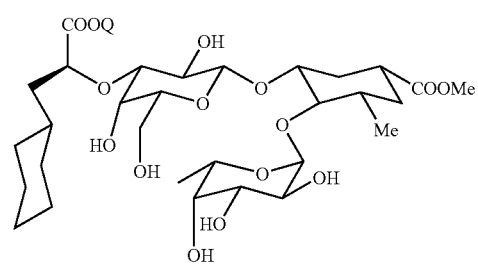

where Q is H or a physiologically acceptable salt, and Me is methyl.

In an embodiment, the present invention provides a compound having the formula:

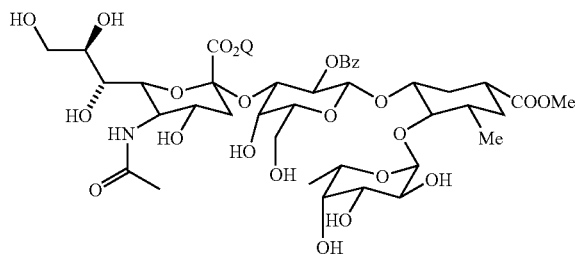

where Q is H or a physiologically acceptable salt, Me is methyl and Bz is benzoyl.

In an embodiment, the present invention provides a compound having the formula:

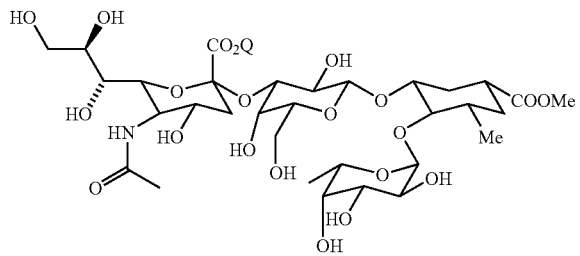

where Q is H or a physiologically acceptable salt, and Me is methyl.

In an embodiment, the present invention provides a compound having the formula:

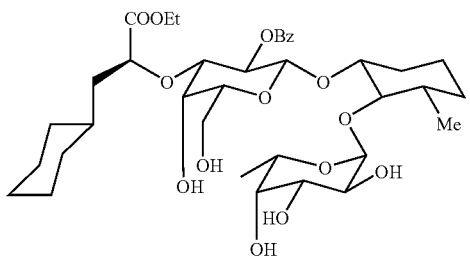

where Me is methyl, Et is ethyl, and Bz in benzoyl. The compound may include a polyethylene glycol attached thereto. Alternatively, multimers may be formed whereby the compound is attached to another of the compound by polyethylene glycol.

In an embodiment, the present invention provides a compound having the formula:

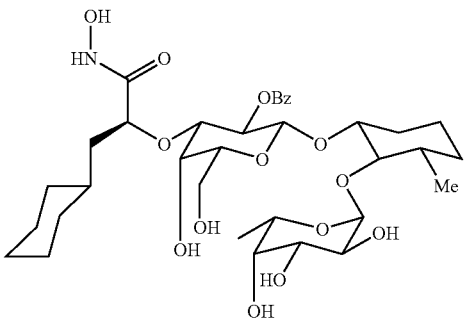

where Me is methyl and Bz in benzoyl. The compound may include a polyethylene glycol attached thereto. Alternatively, multimers may be formed whereby the compound is attached to another of the compound by polyethylene glycol.

In an embodiment, the present invention provides a compound having the formula:

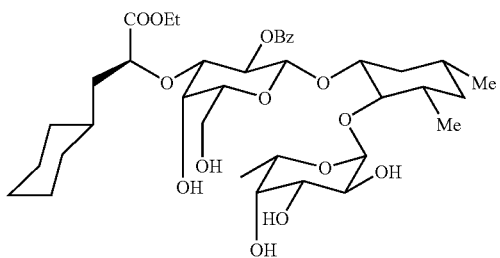

where Me is methyl, Et is ethyl and Bz is benzoyl. The compound may include a polyethylene glycol attached thereto. Alternatively, multimers may be formed whereby the compound is attached to another of the compound by polyethylene glycol.

In an embodiment, the present invention provides a compound having the formula:

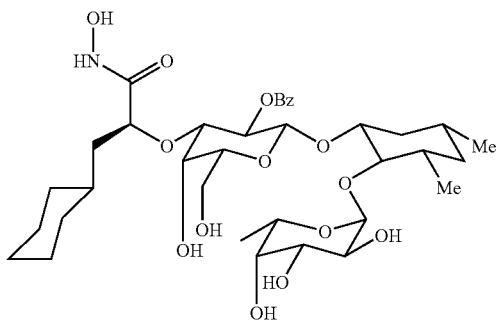

where Me is methyl and Bz is benzoyl. The compound may include a polyethylene glycol attached thereto. Alternatively, multimers may be formed whereby the compound is attached to another of the compound by polyethylene glycol.

For the compounds described herein, a free acid substituent, e.g., $CO_2H$ and $(O=)S(=O)OH$, encompasses a sodium salt of the acid, e.g., COONa and $(O=)S(=O)ONa$, and vice versa. Furthermore, a sodium salt of the acid is merely representative and any physiologically acceptable acid salt (e.g., Li, K, Mg and Ca) is encompassed. In addition, for the compounds described herein, a free acid substituent (or salt thereof) may be modified as an ester (e.g., alkanyl ester) or as an amide or amide-like (e.g., CONHOH).

Figure 10:
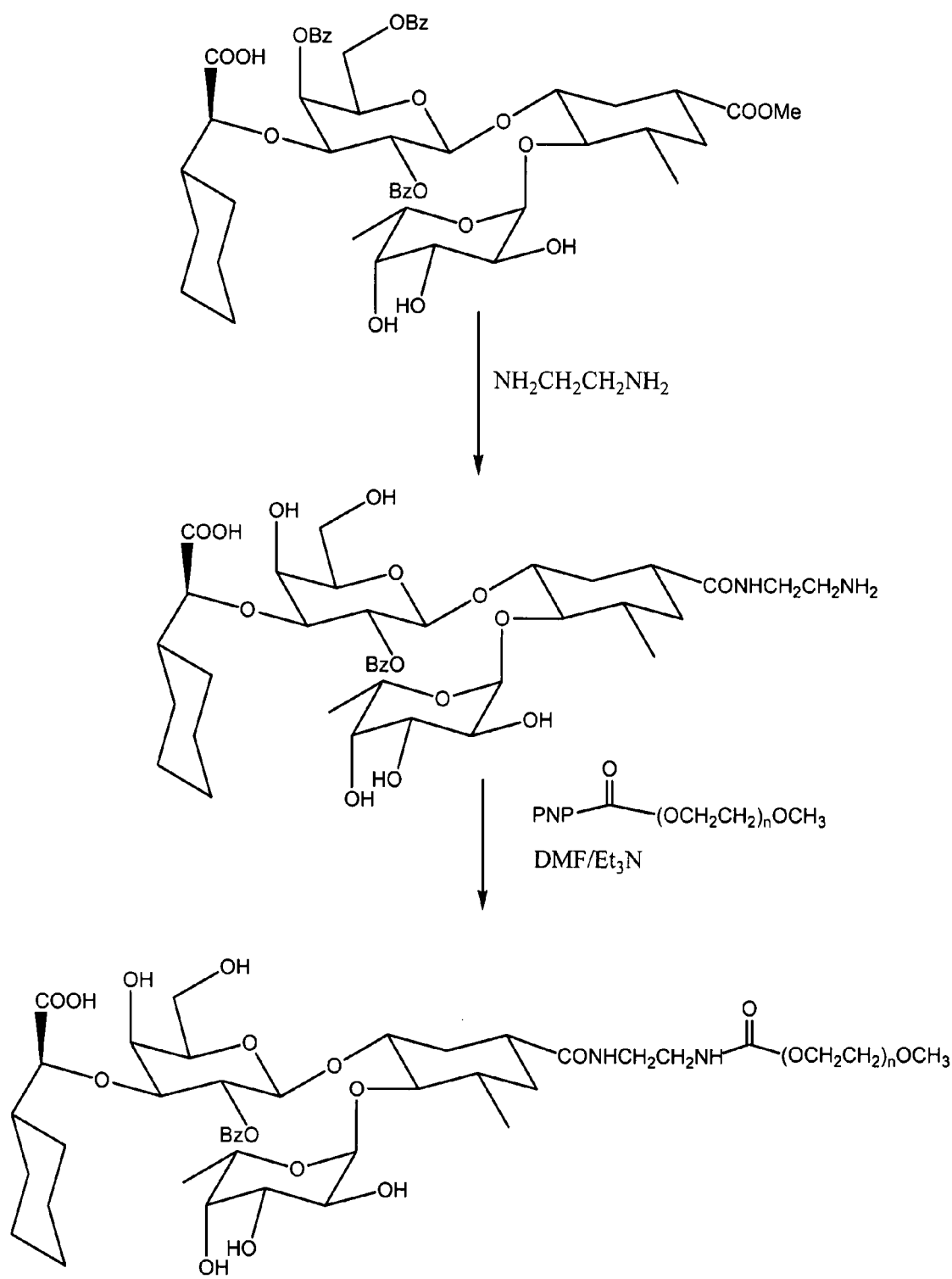
FIG. 10 is a diagram illustrating the synthesis of a pegylated mimic.

For the compounds described herein (both generically and specifically), a polyethylene glycol (PEG), including derivatives thereof, may be attached to a compound. Alternatively, multimers of the same compound or different compounds of the compounds described herein (i.e., two or more compounds joined to one another) may be formed using PEG. Examples of particular compounds amenable to the attachment of a PEG or to the formation of a multimer including PEG, are disclosed above as embodiments of the present invention. Procedures for preparing a pegylated compound or pegylated multimers will be familiar to those in the art or in possession of the present disclosure. Examples are depicted in FIG. 10 (a pegylated compound) and FIG. 11 (a pegylated tetramer).

The following Examples are offered by way of illustration and not by way of limitation.

EXAMPLES

Example 1

Synthesis of GlcNAc Mimic from Tetrahydrophthalic Anhydride (FIG. 1)

Synthesis of Intermediate I:

Amberlyste 15 (50.0 g) was placed in a flask and dried in high vacuo for 1 h. Methanol (1 l) was added, followed by cis-1,2,3,6-tetrahydrophthalic anhydride (50.0 g, 328 mmol) and trimethylorthoformate (100 ml, 914 mmol). The reaction mixture was then vigorously stirred. After 5 days, additional trimethylorthoformate (50 ml, 457 mmol) was added. The reaction was stopped after 9 days (TLC-control: petroleum ether/Et$_2$, 1:2), filtered over celite and washed with methanol. The solvent was removed in vacuo (20 mbar). The brown residue was transferred with CH$_2$Cl$_2$ (150 ml) into a separation funnel and washed with satd. NaHCO$_3$ solution and brine (each 150 ml). The aqueous layers were extracted 3 times with CH$_2$Cl$_2$ (3×150 ml). The combined organic layers were dried over Na$_2$SO$_4$, filtered and concentrated in vacuo (20 mbar) to afford diester I as a brownish oil (57.5 g, 88%).

Synthesis of Intermediate II:

To a stirred suspension of diester I (2.00 g, 10.1 mmol) in pH 7.00 phosphate buffer solution (103 ml, 0.07 M), PLE (8.00 mg, 216 units) was added. The pH was kept at 7 by adding continuously NaOH solution (1.0 M) via syringe pump. The reaction was stirred at 20° C. until one equivalent of NaOH (10 ml) was used (56.5 h, TLC-control: petroleum ether/Et$_2$O, 1:2). The reaction mixture was transferred into a separation funnel with ethyl acetate (100 ml). The layers were separated and the organic layer was extracted twice with pH 7.00 phosphate buffer solution (2×60 ml). The combined aqueous layers were acidified to pH 2 with 1 M HCl solution and extracted four times with ethyl acetate (4×150 ml). To separate the layers NaCl was added. The combined organic layers were dried over Na$_2$SO$_4$, filtered and concentrated in vacuo to afford the monoester II as a yellowish oil (1.67 g, 90%). 96.0% ee. (GC), 96.4% ee. (rot.), $[\alpha]_D^{21}$+15.23° (c=0.195, EtOH), (Lit. +15.8° (c=0.2, EtOH), [*Angew. Chem. Int. Ed. Engl.*, 1984, 23, 142]).

Synthesis of Intermediate III:

A solution of monoester II (0.992 g, 5.38 mmol) in dry CH$_2$Cl$_2$ (18 ml) was treated with (COCl)$_2$ (0.7 ml, 8.15 mmol) and DMF (14 μl), stirred for 3 h at r.t. and evaporated (rotavapor purged with argon). A solution of the residue in dry THF (20 ml) was added dropwise over a period of 20 minutes to a boiling suspension of 2-mercaptopyridine-1-oxide sodium salt (974.8 mg, 6.49 mmol), t-BuSH (3.1 ml, 27.5 mmol), and 4-DMAP (26.3 mg, 0.216 mmol) in dry THF (50 ml). The solution was stirred at reflux for 3 h (TLC-control: petroleum ether/Et$_2$O, 10:1). The reaction mixture was then cooled down to r.t. (room temperature) and transferred into a separation funnel with ethyl acetate (50 ml) and washed with water (100 ml). The aqueous layer was extracted twice with ethyl acetate (2×100 ml). The combined organic layers were dried over Na$_2$SO$_4$, filtered and concentrated in vacuo (200 mbar). The crude product was purified by column chromatography (petroleum ether/Et$_2$O, 30:1 to 15:1) to afford methylester III as a yellowish oil (584.9 mg, 83%). $[\alpha]_D^{21}$+78.23° (c=1.010, CHCl$_3$).

Synthesis of Intermediate IV:

To a stirred suspension of methylester III (5.19 g, 37.0 mmol) in pH 7.00 phosphate buffer solution (520 ml, 0.07 M), PLE (51.2 mg, 1382 units) was added. The pH was kept at 7 by adding NaOH solution (1.0 M) via syringe pump. The reaction was stirred at r.t. until one equivalent of NaOH (37 ml) was used (11 h, TLC-control: petroleum ether/Et$_2$O, 1:1). The reaction mixture was transferred into a separation funnel and washed twice with ethyl acetate (2×300 ml). The layers were separated and the organic layers were extracted twice with pH 7.00 phosphate buffer solution (2×300 ml). The combined aqueous layers were acidified to pH 2 with aqueous HCl (30 ml, 4 M) and extracted three times with ethyl acetate (3×400 ml). The combined organic layers were dried over Na$_2$SO$_4$, filtered and concentrated in vacuo (100 mbar). The crude product was filtered through a short plug of silica affording acid IV as a pale yellowish oil (3.92 g, 84%). 96.3% ee. (GC), 94.3% ee. (rot.), $[\alpha]_D^{21}$+89.12° (c=6.730, MeOH), (Lit. +94.5° (c=7, MeOH), [*Acta Chem. Scand.*, 1970, 24, 2693]).

Synthesis of Intermediate V:

Acid IV (8.30 g, 65.7 mmol) was placed in a flask purged with argon and suspended in water (180 ml). The reaction mixture was cooled down to 0° C. and NaHCO$_3$ (16.6 g, 197 mmol) was added, followed by a solution of KI (65.4 g, 394 mmol) and iodine (17.5 g, 68.9 mmol) in water (150 ml). The reaction was stirred at r.t. for 24 h and then extracted three times with CH$_2$Cl$_2$ (3×60 ml). The combined organic layers were washed with a solution of Na$_2$S$_2$O$_3$ (50 g) in water (250 ml). The aqueous layer was extracted twice with CH$_2$Cl$_2$ (2×60 ml). The combined organic layers were protected from light, dried over Na$_2$SO$_4$, filtered and concentrated in vacuo (20 mbar) and quickly in high vacuo to afford iodolactone V as an off-white solid (15.79 g, 95%). $[\alpha]_D^{21}$+35.960 (c=0.565, CHCl$_3$).

Synthesis of Intermediate VI:

Iodolactone V (15.73 g, 62.2 mmol) was dissolved in dry THF (340 ml). Then DBU (14 ml, 93.3 mmol) was added and the mixture was refluxed for 20 h (TLC-control: petroleum ether/Et$_2$, 1:1). The reaction mixture was cooled down to r.t., transferred with Et$_2$O (200 ml) into a separation funnel and extracted with aqueous HCl (400 ml, 0.5 M) and brine (400 ml). The aqueous layers were extracted three times with Et$_2$O (3×200 ml). The combined organic layers were dried over Na$_2$SO$_4$, filtered and concentrated in vacuo (350 mbar). The crude product was purified by column chromatography (petroleum ether/CH$_2$Cl$_2$/Et$_2$O, 20:5:1 to 8:5:1) to afford lactone VI as a yellowish oil (7.28 g, 94%). $[\alpha]_D^{21}$+187.31° (c=1.080, CHCl$_3$).

Synthesis of Intermediate VII:

NaHCO$_3$ (4.36 g, 51.8 mmol) was dried in high vacuum for 2 h. Then, freshly distilled methanol (268 ml) was added followed by lactone VI (6.38 g, 51.4 mmol). The reaction mixture was then stirred under argon for 12 h (TLC-control: petroleum ether/Et$_2$O, 1:1). The solvent was evaporated and the residue transferred into a separation funnel with CH$_2$Cl$_2$ (60 ml) and extracted with water (60 ml) and brine (60 ml). The aqueous layers were extracted twice with CH$_2$Cl$_2$ (2×60 ml). The combined organic layers were dried over Na$_2$SO$_4$, filtered and concentrated in vacuo (50 mbar) to obtain the alcohol as a yellowish oil (7.77 g, 96%). To a solution of the alcohol in dry CH$_2$Cl$_2$ (150 ml), tert-butyldimethylsilyl chloride (14.93 g, 99 mmol) was added in small portions, followed by DBU (18.4 ml, 123.4 mmol). The reaction was stirred at r.t for 12 h (TLC-control: petroleum ether/Et$_2$O, 20:1) and then quenched with methanol (20 ml). The reaction mixture was transferred into a separation funnel with CH$_2$Cl$_2$ (100 ml), washed with satd. NaHCO$_3$ solution (100 ml) and brine (100 ml). The aqueous layers were extracted twice with CH$_2$Cl$_2$ (2×100 ml). The combined organic layers were dried over Na$_2$SO$_4$, filtered and evaporated (200 mbar). The crude product was purified by column chromatography (petroleum ether/Et$_2$O, 40:1 to 20:1) to afford silylether VII as a colorless oil (13.96 g, quantitative yield). $[\alpha]_D^{21}$+1.97° (c=1.045, CHCl$_3$).

Synthesis of Intermediate VIII:

A solution of silylether VII (1.21 g, 4.47 mmol) in CH$_2$Cl$_2$ (36 ml) was cooled to 10° C., then m-CPBA (1.92 g, 11.1 mmol) was added in one portion. The reaction mixture was stirred at 10° C. for 15 h. Over a period of 2 hours the temperature was raised to r.t and the reaction stopped (TLC-control: petroleum ether/Et$_2$O, 5:1). The mixture was diluted with CH$_2$Cl$_2$ (150 ml) and transferred into a separation funnel. The excess of m-CPBA was destroyed by washing twice with satd. Na$_2$S$_2$O$_3$ solution (2×150 ml). The organic layer was successively washed with satd. NaHCO$_3$ solution (150 ml) and brine (150 ml). The aqueous layers were extracted twice with CH$_2$Cl$_2$ (2×100 ml). The combined organic layers were dried over Na$_2$SO$_4$, filtered and concentrated in vacuo. The crude product was purified by column chromatography (petroleum ether/Et$_2$O, 12:1 to 10:1) to obtain epoxide VIII as yellowish oil (1.001 g, 78%). $[\alpha]_D^{21}$-25.60 (c=0.985, CHCl$_3$).

Synthesis of Intermediate IX:

CuCN (635.4 mg, 7.09 mmol) was dried in high vacuo at 150° C. for 30 minutes, suspended in dry THF (10 ml) and cooled down to −78° C. MeLi (1.6 M in Et$_2$O, 8.90 ml, 14.2 mmol) was slowly added via syringe and the temperature was raised over a period of 30 minutes to −10° C. The mixture was again cooled down to −78° C. followed by the addition of freshly distilled BF$_3$ etherate (360 µl) in THF (2 ml). After stirring for 20 minutes, epoxide VIII (408.0 mg, 1.42 mmol) in THF (10 ml) was added. The reaction was stopped after 5 h stirring at −78° C. (TLC-control: petroleum ether/Et$_2$O, 3:1). The excess of MeLi was quenched with a mixture of methanol (4 ml) and triethylamine (4 ml). The mixture was transferred with Et$_2$O (100 ml) into a separation funnel and extracted with 25% aq. NH$_3$/satd. NH$_4$Cl (1:9) solution. The organic layer was then successively washed with brine (60 ml), 5% acetic acid (60 ml), satd. NaHCO$_3$ solution (60 ml) and brine (60 ml). The aqueous layers were extracted twice with Et$_2$O (2×100 ml). The combined organic layers were dried over Na$_2$SO$_4$, filtered and concentrated in vacuo (20 mbar). The crude product was purified by column chromatography (petroleum ether/Et$_2$O, 10:1 to 8:1) to afford GlcNAc-mimic IX a reddish oil (337.0 mg, 78%). $[\alpha]_D^{21}$-28.34° (c=1.020, CHCl$_3$).

Synthesis of Intermediate X:

After a mixture of IX (347.5 mg, 1.15 mmol), ethyl 2,3,4-tri-O-benzyl-L-fucothiopyranoside (1.111 g, 2.32 mmol), (Bu)$_4$NBr (1.122 g, 3.48 mmol), 2,6-di-tert-butyl-4-methylpyridine (713.3 mg, 3.47 mmol), and powdered 4 Å molecular sieves (3 g) in CH$_2$Cl$_2$ (12 ml) and DMF (3 ml) was stirred at r.t. under Ar for 4 h, CuBr$_2$ (775.9 mg, 3.47 mmol) was added and the reaction mixture was stirred at r.t. for 20 h (TLC-control: toluene/petroleum ether/EtOAc, 3:3:1). The reaction mixture was filtered over Celite and the filtrate was diluted with CH$_2$Cl$_2$ (20 ml). The organic layer was washed with satd. NaHCO$_3$ solution and brine (each 40 ml) and the aqueous layers were extracted three times with CH$_2$Cl$_2$ (3×40 ml). The combined organic layers were dried with Na$_2$SO$_4$, filtered and co-evaporated with toluene to dryness. The residue was purified by column chromatography (petroleum ether/Et$_2$O, 7:1 to 5:1) to yield compound X as a yellowish oil (631.4 mg, 76%). $[\alpha]_D^{21}$-40.66° (c=0.790, CHCl$_3$).

Synthesis of Intermediate XI:

To a solution of disaccharide mimic X (139.5 mg, 0.194 mmol) in THF (5 ml), TBAF (390 µl, 0.390 mmol) was added. After 26 h additional TBAF (200 µl, 0.200 mmol) was added, and the solution was continued stirring. The reaction was stopped after 50 h and concentrated in vacuo (TLC-control: petroleum ether/ethyl acetate, 5:1). The crude product was purified by column chromatography (petroleum ether/ethyl acetate, 3:1) to afford the unprotected disaccharide mimic XI as a white solid (95.7 mg, 81%). $[\alpha]_D^{21}$-43.03° (c=1.090, CHCl$_3$).

Synthesis of Intermediate XII:

Dry CH$_2$Cl$_2$ (16 ml) was added to a mixture of the thioglycoside (562.3 mg, 0.719 mmol), glycosyl acceptor XI (335.6 mg, 0.555 mmol) and activated 4 Å molecular sieves (4 g) under argon atmosphere. A suspension of DMTST (440.6 mg, 1.706 mmol) and activated 4 Å molecular sieves (2 g) in CH$_2$Cl$_2$ (8 ml) was prepared in a second flask. Both suspensions were stirred at room temperature for 4 h, before adding the DMTST suspension via syringe to the other suspension with some additional CH$_2$Cl$_2$ (1 ml). The reaction was stopped after 63 h (TLC-control: petroleum ether/Et$_2$O, 1:1), and filtered through celite, washing with CH$_2$Cl$_2$. The filtrate was successively washed with satd. solution of NaHCO$_3$ (40 ml) and water (100 ml). The aqueous layers were three times extracted with DCM (3×60 ml). The combined organic layers were dried with Na$_2$SO$_4$, filtered and concentrated in vacuo. The crude product was purified by repeated column chromatography (petroleum ether/Et$_2$O, 1:1) to afford tetrasaccharide XII as a white foam (484.9 mg, 66%). $[\alpha]_D^{21}$-52.80 (c=1.050, CHCl$_3$).

Synthesis of Product XIII:

A mixture of XII (132.5 mg, 0.100 mmol), Pd(OH)$_2$/C (50 mg), dioxane (3 ml) and water (0.75 ml) was hydrogenated in a Parr-shaker under 4 bar at r.t. After 20 h the mixture was filtered through Celite and set up with new Pd(OH)$_2$/C (50 mg) for another 26 h, after which TLC control indicated completion of the reaction. The reaction mixture was filtered over Celite and evaporated to dryness. The residue was redissolved in methanol (4 ml) and sodium methanolate (0.150 mmol in 160 µl MeOH) was added. After stirring at r.t. for 16 h the reaction was quenched by addition of acetic acid (17 µl). The mixture was concentrated in vacuo and purified by preparative, reversed-phase HPLC to afford compound XIII as a white solid (57.1 mg, 76%). $[\alpha]_D^{21}$-85.02° (c=0.570, MeOH).

Example 2

Figure 2:
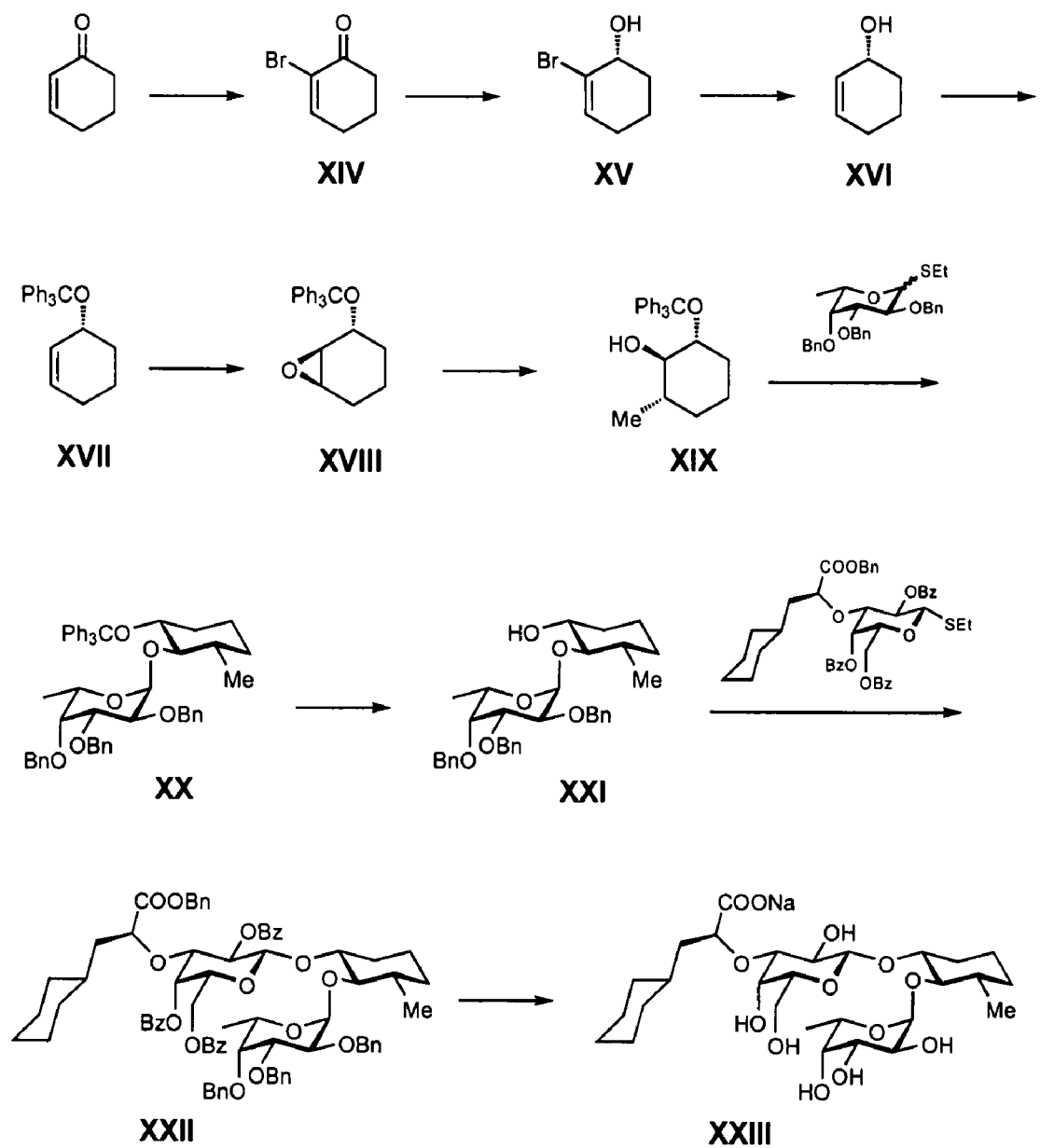
FIG. 2 is a diagram illustrating the synthesis of GlcNAc mimics from cyclohexenon.

Synthesis of GlcNAc Mimics from Cyclohexenon (FIG. 2)

Synthesis of Intermediate XIV:

2-Cyclohexenone (9.8 ml, 101 mmol) was dissolved in $CH_2Cl_2$ (250 ml) in a light protected flask, then the solution was cooled to 0° C. Bromine (5.4 ml, 105 mmol) in $CH_2Cl_2$ (100 ml) was added via dropping funnel over 35 min. The clear yellow solution was stirred at 0° C. for 2.5 h, then $Et_3N$ (23.1 ml, 166 mmol) in $CH_2Cl_2$ (20 ml) was added portionwise via dropping funnel, causing a color change from clear yellow to brown with precipitate. The mixture was stirred at room temperature for 2 h, then stopped. The reaction mixture was diluted with $CH_2Cl_2$ (50 ml) and washed twice with HCl 3% (2×50 ml). The aqueous layers were extracted with $CH_2Cl_2$ (2×25 ml) and the combined organic layers were washed with a mixture of brine (80 ml) and water (100 ml). The layers were separated and the aqueous layer was extracted with $CH_2Cl_2$ (2×50 ml). The combined organic layers were concentrated in vacuo to afford a brown residue still dissolved in a few ml of $CH_2Cl_2$, and was then treated with activated charcoal and filtered through celite. The clear green mixture was concentrated to dryness. Recrystallization from hexane/EtOAc (100 ml:few drops) gave offwhite crystals. The crystals were dried in a desiccator for 12 h affording bromide XIV (11.0 g, 62.8 mmol, 62%). $^1$H-NMR ($CDCl_3$, 500.1 MHz): δ=2.07 (m, 2 H, H-5), 2.45 (m, 2 H, H-4), 2.63 (m, 2 H, H-6), 7.42 (t, $^3J$=4.4 Hz, 1 H, H-3).

Synthesis of Intermediate XV:

(S)-α,α-diphenylprolinol (290 mg, 1.14 mmol) was dissolved in THF (20 ml) in a flame dried, light protected flask, then under stirring $B(OMe)_3$ (153 μl, 1.37 mmol) was added via syringe to the solution. The mixture was stirred for 1 h at room temperature, before $BH_3.N,N$-diethylaniline (2.00 ml, 11.2 mmol) was added and the resulting solution cooled to −10° C. A solution of bromide XIV (2.00 g, 11.4 mmol) in THF (15 ml) was then added over 45 min. The clear yellow mixture was stirred for 3 h at 0° C. After complete conversion of the ketone the reaction was quenched with HCl (1 M, 20 ml). The resulting mixture was diluted with $CH_2Cl_2$ (40 ml) and water (50 ml). After separation the organic layer was washed with brine (20 ml) and both aqueous layers were extracted twice with $CH_2Cl_2$ (2×25 ml). The combined organic layers were dried with $Na_2SO_4$ and concentrated in vacuo. Chromatographic purification of the crude product (petroleum ether/$Et_2O$, 2:1 to 1.5:1) gave XV (1.89 g, 10.7 mmol, 93%) as a colorless oil and with an optical yield of 96% ee determined by optical rotation and derivatisation with (1R)-(−)-MTPA-Cl. $[α]_D^{21=}$+83.0 (c=1.01; $CHCl_3$); $^1$H-NMR ($CDCl_3$, 500.1 MHz): δ=1.59-1.66 (m, 1 H, H-5$_a$), 1.69-1.77 (m, 1 H, H-5$_b$), 1.86-1.97 (m, 2 H, H-6$_a$, H-6$_b$), 2.00-2.07 (m, 1 H, H-4$_a$), 2.09-2.16 (m, 1 H, H-4$_b$), 2.26 (m, 1 H, OH), 4.20 (m, 1 H, H-1), 6.19 (t, $^3J$=4.0 Hz, 1 H, H-3).

Synthesis of Intermediate XVI:

XV (7.33 g, 41.4 mmol) was dissolved in $Et_2O$ (43 ml) in a flame dried flask equipped with a dropping funnel. tert-BuLi (1.7 M in pentane, 133 mmol) was dropwise added at −78° C. over 1 h and 15 min. After complete addition, the clear yellowish mixture was stirred for further 1 h and 30 min at −78° C. and was then warmed up to −20° C. over 3 hrs and 15 min. The reaction was quenched by addition of satd. solution of $NaHCO_3$ (50 ml) and stirred for a further hour at room temperature. The reaction was diluted by addition of water (20 ml) and $Et_2O$ (20 ml). The layers were separated and the aqueous layer extracted twice with $Et_2O$ (2×30 ml). The combined organic layers were dried with $Na_2SO_4$ and concentrated in vacuo (>200 mbar) to afford a yellow mixture (still presence of solvent) which was purified by column chromatography (petroleum ether/$Et_2O$, 2:1 to 1:1). The product was mostly concentrated in vacuo (>200 mbar), then the rest of the solvent was removed by distillation under argon with vigreux column to afford alcohol XVI (3.39 g, 34.6 mmol, 85%) as a clear brown oil. $[α]_D^{21=}$+117.7 (c=0.95; $CHCl_3$); $^1$H-NMR ($CDCl_3$, 500.1 MHz): δ=1.53-1.64 (m, 3 H, H-5$_a$, H-6$_a$, OH), 1.68-1.77 (m, 1 H, H-5$_b$), 1.87 (m, 1 H, H-6$_b$), 1.92-2.06 (m, 2 H, H-4$_a$, H-4$_b$), 4.19 (s, 1 H, H-1), 5.74 (dd, $^3J$=2.4, 10.0 Hz, 1 H, H-2), 5.82 (m, 1 H, H-3).

Synthesis of Intermediate XVII:

Alcohol XVI (1.51 g, 15.3 mmol) was stirred in $CH_2Cl_2$ (35 ml) at room temperature. Trityl chloride (9.54 g, 34.2 mmol) was added to the mixture, then DBU (5.9 ml, 39.5 mmol) was added via syringe. The brown mixture was stirred for 45 h, then stopped. The reaction mixture was diluted with $CH_2Cl_2$ (50 ml) and washed with satd. solution of $NaHCO_3$ (50 ml). The layers were separated and the aqueous layer was extracted twice with $CH_2Cl_2$ (2×25 ml). The combined organic layers were dried with $Na_2SO_4$ and concentrated to dryness. The resulting viscous brown oil was purified by column chromatography (petroleum ether/toluene, 11:1 to 4:1) affording tritylether XVII (3.72 g, 10.9 mmol, 71%) as a yellow solid. $[α]_D^{21=}$+74.6 (c=1.15; $CHCl_3$); $^1$H-NMR ($CDCl_3$, 500.1 MHz): δ=1.31-1.41 (m, 3 H, H-5$_a$, H-6), 1.68-1.76 (m, 1 H, H-5$_b$), 1.80 (m, 1 H, H-4$_a$), 1.98 (m, 1 H, H-4$_b$), 4.06 (s, 1 H, H-1), 5.03 (m, 1 H, H-2), 5.61 (m, 1 H, H-3), 7.21-7.54 (m, 15 H, 3 $C_6H_5$); elemental analysis calcd (%) for $C_{25}H_{24}O$ (340.46): C 88.20, H. 7.10; found: C 88.01, H 7.29.

Synthesis of Intermediate Anti-XVIII:

Tritylether XVII (948 mg, 2.79 mmol) was dissolved under argon atmosphere in $CH_2Cl_2$ (30 ml) and $NaHCO_3$ (281 mg, 3.34 mmol) was added. The mixture was cooled to 0° C. and under stirring m-chloroperbenzoic acid (70%, 960 mg, 5.56 mmol) was added. After stirring for 1.5 h the reaction temperature was gradually raised to room temperature and the mixture was stirred for another 3.5 h. The reaction was diluted with $CH_2Cl_2$ (50 ml) and transferred to a separation funnel. The excess of m-chloroperbenzoic acid was destroyed by washing with satd. solution of $Na_2S_2O_3$ (2×150 ml). The organic layer was then successively washed with satd. $Na_2CO_3$ solution (150 ml) and brine (150 ml). The aqueous layers were each time extracted with $CH_2Cl_2$ (2×50 ml). The combined organic layers were dried with $Na_2SO_4$ and concentrated in vacuo. The crude product was purified by column chromatography (petroleum ether/EtOAc, 20:1 to 15:1) affording epoxide anti-XVIII (714 mg, 2.00 mmol, 72%) as colorless solid. $[α]_D^{21=}$+26.6 (c=0.67; $CHCl_3$); $^1$H-NMR ($CDCl_3$, 500.1 MHz): δ=1.02-1.11 (m, 1 H, H-5$_a$), 1.15-1.22 (m, 1 H, H-6$_a$), 1.37-1.43 (m, 1 H, H-5$_b$), 1.53 (m, 1 H, H-6$_b$), 1.64-1.71 (m, 1 H, H-4$_a$), 1.90 (m, 1 H, H-4$_b$), 2.25 (m, 1 H, H-2), 2.97 (m, 1 H, H-3), 3.86 (m, 1 H, H-1), 7.23-7.53 (m, 15 H, 3 $C_6H_5$); elemental analysis calcd (%) for $C_{25}H_{24}O_2$ (356.46): C 84.24, H 6.79; found: C 83.86, H 6.85.

Synthesis of Intermediate XIX:

Copper(I) iodide (499 mg, 2.62 mmol) was dried at high vacuo at 200° C. for 30 minutes, then flushed with argon and suspended in dry diethylether (10 ml). After cooling to −20° C. MeLi (1.6 M in ether, 3.26 ml, 5.22 mmol) was slowly added and the solution was stirred for 15 minutes. A solution of epoxide anti-XVIII (310 mg, 0.870 mmol) in diethylether (7 ml) was added to the cuprate. After stirring for 30 minutes at −20° C. the reaction mixture was slowly brought to room temperature and stirred for one week. The reaction was diluted with tert-butyl methyl ether (10 ml) and quenched at 0° C. with satd. solution of NaHCO$_3$ (10 ml). The reaction mixture was further diluted and extracted with tert-butyl methyl ether and satd. solution of NaHCO$_3$ (each 20 ml). The aqueous layer was extracted twice with tert-butyl methyl ether (2×50 ml). The combined organic layers were dried with Na$_2$SO$_4$ and concentrated. The residue was purified by flash chromatography (petroleum ether/EtOAc/Et$_3$N, 13:1:0.07) to yield XIX (206 mg, 64%) as yellowish resin. [α]$_D^{21}$=−57.6 (c=0.52; CHCl$_3$); $^1$H-NMR (CDCl$_3$, 500.1 MHz): δ=0.78 (m, 1 H, H-5$_a$), 0.94 (m, 1 H, H-4$_a$), 1.00 (d, $^3$J=6.4 Hz, 3 H, CH$_3$), 1.17 (m, 1 H, H-3), 1.32 (m, 1 H, H-6$_a$), 1.40 (m, 1 H, H-5$_b$), 1.46-1.49 (m, 2 H, H-4$_b$, H-6$_b$), 2.67 (s, 1 H, OH), 2.83 (ddd, $^3$J=4.1, 8.6, 11.1 Hz, 1 H, H-1), 3.32 (t, $^3$J=9.2 Hz, 1 H, H-2), 7.21-7.30, 7.49-7.50 (m, 15 H, 3 C$_6$H$_5$); elemental analysis calcd (%) for C$_{26}$H$_{28}$O$_2$ (372.51): C 83.83, H 7.58; found: C 83.51, H 7.56.

Synthesis of Intermediate XX:

A solution of Br$_2$ (43 μl, 0.837 mmol) in CH$_2$Cl$_2$ (1 ml) was added dropwise at 0° C. to a solution of ethyl 2,3,4-tri-O-benzyl-L-fucothiopyranoside (349 mg, 0.729 mmol) in CH$_2$Cl$_2$ (2 ml). After stirring for 50 min at 0° C., cyclohexene (100 μl) was added and the solution stirred for another 20 min. The mixture was dropwise added to a solution of XIX (208 mg, 0.558 mmol) and Et$_4$NBr (154 mg, 0.733 mmol) in DMF/CH$_2$Cl$_2$ (10 ml, 1:1) which has been stirred with activated 3 Å molecular sieves (850 mg) for 2 h. The mixture was stirred for 14 h at room temperature. The reaction was quenched with pyridine (1 ml) and filtered over celite with addition of CH$_2$Cl$_2$ (20 ml). The solution was washed with brine (40 ml) and the aqueous layer was extracted with CH$_2$Cl$_2$ (3×30 ml). The combined organic phases were dried with Na$_2$SO$_4$, the solvent was removed azeotropic with toluene, and the residue was purified by flash chromatography (petroleum ether/toluene/ethyl acetate/Et$_3$N, 20:5:1:0.26) to afford 254 mg (58%, 0.322 mmol) of XX as colorless foam. [α]$_D^{21}$=−36.4 (c=0.51; CHCl$_3$); $^1$H-NMR (CDCl$_3$, 500.1 MHz): δ=0.81 (d, $^3$J=6.5 Hz, 3 H, Fuc H-6), 1.05 (m, 1 H, H-6$_a$), 1.18 (d, $^3$J=7.6 Hz, 3 H, CH$_3$), 1.15-1.28 (m, 2 H, H-4$_a$, H-5$_a$), 1.34 (m, 1 H, H-6$_b$), 1.75 (m, 1 H, H-4$_b$), 1.85-1.90 (m, 2 H, H-3, H-5$_b$), 2.91 (m, 1 H, H-2), 3.52 (m, 1 H, Fuc H-4), 3.64 (m, 1 H, Fuc H-5), 3.76 (dd, $^3$J=2.7, 10.1 Hz, 1 H, Fuc H-3), 3.81 (m, 1 H, H-1), 3.88 (dd, $^3$J=3.6, 10.1 Hz, 1 H, Fuc H-2), 4.54 (m, 1 H, CH$_2$Ph), 4.61 (d, 1 H, Fuc H-1), 4.61, 4.64, 4.65, 4.77, 4.92 (5 m, 5 H, 3 CH$_2$Ph), 7.17-7.34, 7.48-7.50 (m, 30 H, 6 C$_6$H$_5$).

Synthesis of Intermediate XXI:

To a stirred solution of tritylether XX (241 mg, 0.305 mmol) in CH$_2$Cl$_2$ (4 ml), ZnBr$_2$ (208 mg, 0.924 mmol) and triethylsilane (55 μl, 0.344 mmol) was added. The reaction was quenched after 8 h by adding 100 μl water. CH$_2$Cl$_2$ (10 ml) was added and the reaction mixture extracted with satd. solution of NaHCO$_3$ (30 ml). After separation the aqueous layer was extracted twice with DCM (2×20 ml). The combined organic layers were washed with satd. solution of NaHCO$_3$ (50 ml) and the aqueous layer was extracted twice with DCM (2×50 ml). The combined organic layers were dried with Na$_2$SO$_4$ and concentrated in vacuo. Chromatographic purification of the crude product (petroleum ether/toluene/ethyl acetate, 5:5:1) gave 140 mg (84%, 0.256 mmol) of XXI is yellowish solid. [α]$_D^{21}$=−35.0 (c=0.45; CHCl$_3$); $^1$H-NMR (CDCl$_3$, 500.1 MHz): δ=0.98 (m, 1 H, H-4$_a$), 1.08 (d, $^3$J=6.4 Hz, 3 H, CH$_3$), 1.16 (d, $^3$J=6.5 Hz, 3 H, Fuc H-6), 1.22-1.30 (m, 2 H, H-5$_a$, H-6$_a$), 1.51 (m, 1 H, H-3), 1.61-1.67 (m, 2 H, H-4$_b$, H-5$_b$), 2.00 (m, 1 H, H-6$_b$), 2.87 (t, $^3$J=9.3 Hz, 1 H, H-2), 3.37 (m, 1 H, H-1), 3.70 (m, 1 H, Fuc H-4), 3.97 (dd, $^3$J=2.7, 10.2 Hz, 1 H, Fuc H-3), 4.10-4.14 (m, 2 H, Fuc H-2, Fuc H-5), 4.65, 4.70, 4.76, 4.77, 4.86, 4.99 (6 m, 6 H, 3 CH$_2$Ph), 5.00 (d, 1 H, Fuc H-1), 7.25-7.39 (m, 15 H, 3 C$_6$H$_5$); elemental analysis calcd (%) for C$_{34}$H$_{42}$O$_6$ (546.69): C 74.70, H 7.74; found: C 74.68, H 7.80.

Synthesis of Intermediate XXII:

Dry CH$_2$Cl$_2$ (8 ml) was added to a mixture of the thioglycoside (254 mg, 0.325 mmol), the glycosyl acceptor XXI (137 mg, 0.251 mmol) and activated 4 Å molecular sieves (2 g) under argon atmosphere. A suspension of DMTST (206 mg, 0.798 mmol) and activated 4 Å molecular sieves (1 g) in CH$_2$Cl$_2$ was prepared in a second flask. Both suspensions were stirred at room temperature for 4 h, before adding the DMTST suspension via syringe to the other suspension. The reaction was stopped after 43 h and filtered through celite, washing with CH$_2$Cl$_2$. The filtrate was successively washed with satd. solution of NaHCO$_3$ (20 ml) and water (60 ml). The aqueous layers were each time extracted with DCM (3×30 ml). The combined organic layers were dried with Na$_2$SO$_4$ and concentrated in vacuo. The crude product was purified by column chromatography (petroleum ether/toluene/ethyl acetate, 7:7:1 to 5:5:1) to afford 187 mg (59%, 0.148 mmol) of XXII as colorless foam. [α]$_D^{21}$=−51.0 (c=0.51; CHCl$_3$); $^1$H-NMR (CDCl$_3$, 500.1 MHz): δ=0.45-1.46 (m, 19 H, CyCH$_2$, MeCy), 1.04 (d, $^3$J=6.3 Hz, 3 H, CH$_3$), 1.44 (d, $^3$J=6.4 Hz, 3 H, Fuc H-6), 1.86 (m, 1 H, MeCy), 3.21 (t, $^3$J=9.1 Hz, 1 H, H-2), 3.48 (m, 1 H, H-1), 3.51 (s. 1 H, Fuc H-4), 3.82 (dd, $^3$J=3.3, 9.9 Hz, 1 H, Gal H-3), 3.91 (m, 1 H, Gal H-5), 4.02 (dd, $^3$J=3.3, 10.3 Hz, 1 H, Fuc H-2), 4.05 (dd, $^3$J=2.3, 10.3 Hz, 1 H, Fuc H-3), 4.12 (dd, $^3$J=4.6, 7.9 Hz, 1 H, Lac H-2), 4.24 (dd, $^3$J=7.2 Hz, $^2$J=11.4 Hz, 1 H, Gal H-6$_a$), 4.26 (m, 1 H, CH$_2$Ph), 4.38 (dd, $^3$J=5.7 Hz, $^2$J=11.4 Hz, 1 H, Gal H-6$_b$), 4.51 (m, 1 H, CH$_2$Ph), 4.54 (d, $^3$J=8.2 Hz, 1 H, Gal H-1), 4.63, 4.67, 4.74, 4.77 (4 m, 4 H, 2 CH$_2$Ph), 4.88 (m, 1 H, Fuc H-5), 5.05 (m, 1 H, CH$_2$Ph), 5.06 (d, $^3$J=3.5 Hz, 1 H, Fuc H-1), 5.11 (m, 1 H, CH$_2$Ph), 5.60 (m, 1 H, Gal H-2), 5.84 (m, 1 H, Gal H-4), 7.17-7.34, 7.42-7.46, 7.52-7.58, 8.03-8.12 (m, 35 H, 7 C$_6$H$_5$); elemental analysis calcd (%) for C$_{77}$H$_{84}$O$_{16}$ (1265.48): C 73.08, H 6.69; found: C 73.16, H 6.76.

Synthesis of Product XXIII:

Pd/C (50 mg, 10% Pd) was suspended under argon atmosphere in ethanol (3 ml) with a catalytic amount of acetic acid. Compound XXII (101 mg, 79.8 μmol) was added and the resulting mixture was hydrogenated under 70 psi at room temperature. After 1 day another 50 mg of Pd/C were added and hydrogenation was continued for another 5 days. The reaction was quenched with CH$_2$Cl$_2$ and filtered on celite, washing with methanol. The filtrate was concentrated under vacuum, redissolved in methanol/water (3:1, 4 ml) and lithium hydroxide (100 mg, 4.18 mmol) was added. After 2 days stirring the mixture was neutralized with Dowex 50×8 (H$^+$), filtered through a Dowex 50 ion exchanger column (Na$^+$ form) and concentrated in vacuo. The residue was purified by column chromatography (CH$_2$Cl$_2$/methanol/water, 5:1:0.1 to 5:2.5:0.25), followed by Sephadex G15 column and lyophilization from dioxane to give 36.5 mg (74%, 59.4 μmol) of XXIII as colorless foam. [α]$_D^{21}$=−84.8 (c=0.32; MeOH); $^1$H-NMR (MeOD, 500.1 MHz): δ=0.87-1.00 (m, 2 H, CyCH$_2$, MeCy), 1.04-1.38 (m, 6 H, CyCH$_2$, MeCy), 1.13 (d, $^3$J=6.3 Hz, 3 H, CH$_3$), 1.20 (d, $^3$J=6.5 Hz, 3 H, Fuc H-6), 1.55-1.74 (m, 10 H, CyCH$_2$, MeCy), 1.92 (m, 1 H), 2.13 (m, 1 H, MeCy), 3.20 (t, $^3$J=9.3 Hz, 1 H, H-2), 3.24 (dd, $^3$J=2.8, 9.3 Hz, 1 H, Gal H-3), 3.42 (m, 1 H, Gal H-5), 3.62-3.68 (m, 3 H, Gal H-2, Gal H-6$_a$, H-1), 3.70-3.75 (m, 3 H, Fuc H-2, Fuc H-4, Gal H-6$_b$), 3.85 (dd, $^3$J=3.3, 10.3 Hz, 1 H, Fuc H-3), 3.88 (m, 1 H, Gal H-4) 4.07 (dd, $^3$J=3.1, 9.3 Hz, 1 H, Lac H-2), 4.29 (d, $^3$J=7.8 Hz, 1 H, Gal H-1), 4.89 (m, 1 H, Fuc H-5), 5.00 (d, $^3$J=3.9 Hz, 1 H, Fuc H-1); elemental analysis calcd (%) for C$_{28}$H$_{47}$NaO$_{13}$.1H$_2$O (614.65+18.02): C 53.16, H 7.81; found: C 53.22, H 7.91.

Example 3

Figure 3:
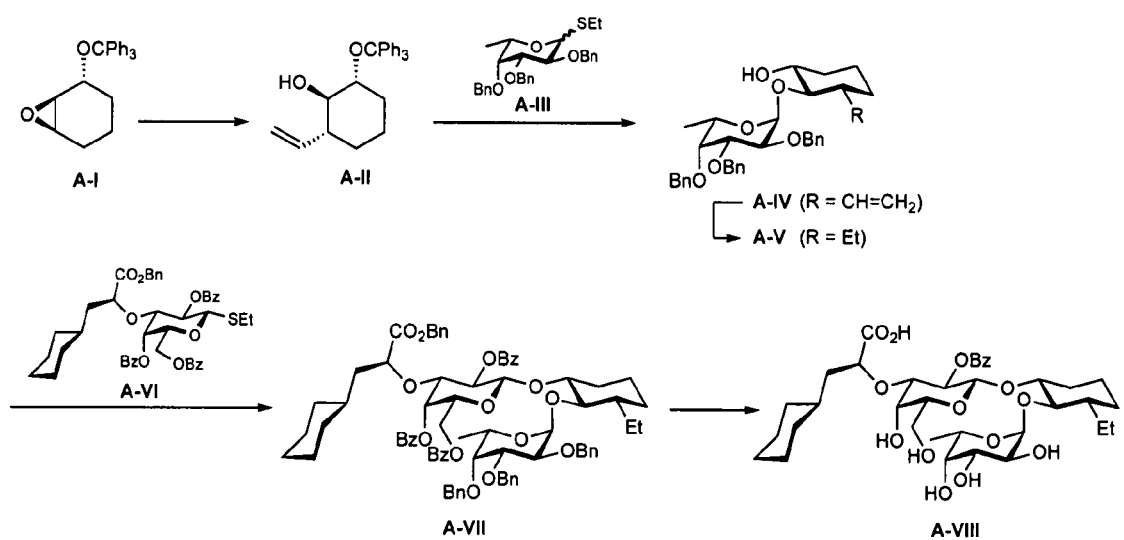
FIG. 3 is a diagram illustrating the synthesis of mimics.

{(1R,2R,3S)-2-[(6-Deoxy-α-L-Galactopyranosyl)
Oxy]-3-Ethyl-Cyclohex-1-yl}2-O-Benzoyl-3-O-
[(1S)-1-Carboxy-2-Cyclohexyl-Ethyl]-β-D-Galacto-
pyranoside (A-VIII; FIG. 3)

General Procedure a for Nucleophilic Opening of Epoxide A-I with Cuprate Reagents.

CuCN (3.81 mmol) was dried in vacuo at 150° C. for 30 min, suspended in dry THF (10 mL) and cooled to −78° C. A solution of the appropriate organo lithium compound (7.63 mmol) was slowly added via syringe and the temperature was raised over a period of 30 min to −20° C. and the mixture stirred at this temperature for 10 min. The mixture was cooled to −78° C. followed by the addition of freshly distilled $BF_3$ etherate (1.53 mmol) in THF (2 mL). After stirring for 20 min, epoxide A-I (0.761 mmol) dissolved in THF (8 mL) was added. The reaction was slowly warmed to −50° C. over 5 h and then stirred at this temperature for 24 h. After slowly warming the reaction to −30° C. over another 21 h the reaction was quenched with a 25% aq. $NH_3$/satd. $NH_4Cl$ (1:9, 20 mL) solution. The mixture was transferred with $Et_2O$ (30 mL) into a separation funnel and extracted with additional 25% aq. $NH_3$/satd. $NH_4Cl$ (1:9, 30 mL) solution. The layers were separated and the organic layer was washed with brine (50 mL). The aqueous layers were extracted with $Et_2O$ (2×30 mL). The combined organic layers were dried over $Na_2SO_4$, filtered and concentrated in vacuo. The crude product was purified by column chromatography (petroleum ether/$Et_2O$, 20:1 to 13:1, +1% $Et_3N$) to afford the corresponding GlcNAc mimic.

General Procedure B for α-Fucosylation and Detritylation.

A solution of $Br_2$ (0.837 mmol) in $CH_2Cl_2$ (1 mL) was added dropwise at 0° C. to a solution of ethyl 2,3,4-tri-O-benzyl-1-thio-L-fucopyranoside (A-III, 0.729 mmol) in $CH_2Cl_2$ (2 mL). After stirring for 50 min at 0° C., cyclohexene (100 µL) was added and the solution stirred for another 20 min. The mixture was added dropwise to a solution of the appropriate GlcNAc mimic (0.558 mmol) and $Et_4NBr$ (0.733 mmol) in DMF/$CH_2Cl_2$ (10 mL, 1:1), which has been stirred with activated 3 Å molecular sieves (850 mg) for 2 h. The mixture was stirred for 14 h at r.t. The reaction was quenched with pyridine (1 mL) and filtered over celite with addition of $CH_2Cl_2$ (20 mL). The solution was washed with brine (40 mL) and the aqueous layer was extracted with $CH_2Cl_2$ (3×30 mL). The combined organic phases were dried with $Na_2SO_4$, filtered and the solvents were removed azeotropically with toluene. The residue was purified by flash chromatography (petroleum ether/diethyl ether, 12:1 to 7:1, +1% $Et_3N$) to afford the fucosylated tritylether. To a stirred solution of the tritylether (0.305 mmol) in $CH_2Cl_2$ (4 mL), $ZnBr_2$ (0.924 mmol) and triethylsilane (0.344 mmol) were added. The reaction was quenched after 8 h by adding water (100 µL). $CH_2Cl_2$ (10 mL) was added and the reaction mixture extracted with satd. aqueous $NaHCO_3$ (30 mL). The aqueous layer was extracted with DCM (2×20 mL). The combined organic layers were washed with satd. aqueous $NaHCO_3$ (50 mL) and the aqueous layer was extracted with DCM (2×50 mL). The combined organic layers were dried with $Na_2SO_4$, filtered and concentrated in vacuo. Chromatographic purification of the crude product (petroleum ether/toluene/ethyl acetate, 7:7:1 to 4:4:1) afforded the corresponding disaccharide mimic.

General Procedure C for DMTST Promoted Glycosylations.

A solution of the thioglycoside A-VI (0.292 mmol) and the appropriate glycosyl acceptor (0.225 mmol) in dry $CH_2Cl_2$ (8 mL) was added via syringe to activated 3 Å molecular sieves (2 g) under argon. A suspension of dimethyl(methylthio) sulfonium triflate (DMTST) (0.685 mmol) and activated 3 Å molecular sieves (1 g) in $CH_2Cl_2$ (4 mL) was prepared in a second flask. Both suspensions were stirred at r.t. for 4 h, then the DMTST suspension was added via syringe to the other suspension with some additional $CH_2Cl_2$ (2 ml). The reaction was stopped after 2 d, filtered through celite and the celite washed with $CH_2Cl_2$ (10 mL). The filtrate was successively washed with satd. aqueous $NaHCO_3$ (25 mL) and water (40 mL). The aqueous layers were extracted with $CH_2Cl_2$ (3×25 mL). The combined organic layers were dried with $Na_2SO_4$, filtered and concentrated in vacuo. The crude product was purified by column chromatography (petroleum ether/toluene/ethyl acetate, 10:10:1 to 5:5:1) to afford the corresponding tetrasaccharide mimic as a colorless foam.

General Procedure D for Deprotection with $Pd(OH)_2$/C and Sodium Methoxide.

$Pd(OH)_2$/C (50 mg, 10% Pd) was suspended under argon in dioxane/$H_2O$ (4:1, 3.75 mL). The appropriate protected compound (77.7 µmol) was added and the resulting mixture was hydrogenated under 70 psi at r.t. After 24 h the mixture was filtered through celite and reacted with fresh $Pd(OH)_2$/C (50 mg) for additional 48 h, until TLC control indicated completion of the reaction. The reaction mixture was filtered through celite and evaporated to dryness. The residue was redissolved in methanol (5 mL) and sodium methoxide (0.194 mmol in 190 µl MeOH) was added. After stirring at r.t. for 16 h the reaction was quenched by addition of acetic acid (22 µL). The mixture was concentrated in vacuo and purified by preparative, reversed-phase HPLC to afford the corresponding antagonists as colorless solids.

(1R,2R,3R)-3-Ethenyl-1-O-triphenylmethyl-cyclohexane-1,2-diol (A-II)

A vinyl lithium solution was generated in situ by treating a solution of tetravinyl tin (409 µL, 2.25 mmol) in THF (3 mL) with nBuLi (2.5 M in hexane, 3.35 mL, 8.38 mmol) during 30 min at 0° C. CuCN (373 mg, 4.16 mmol) in THF (8 mL) was treated with the vinyl lithium solution and $BF_3$ etherate (209 µL, 1.66 mmol) in THF (1.5 mL) according to general procedure A. Epoxide A-I (296 mg, 0.830 mmol) in THF (8 mL) was slowly added and the reaction slowly warmed to −30° C. (−78° C.: 15 min; −78° C. to −50° C.: 1.5 h; −50°: 13 h; −50° C. to −30° C.: 1.5 h; −30° C.: 24 h). Work-up and purification according to general procedure A yielded A-II (258 mg, 81%) as a yellowish resin.

$[α]_D^{21}$=−33.7 (c=0.53, $CHCl_3$); $^1$H-NMR ($CDCl_3$, 500.1 MHz) δ: 0.84 (m, 1 H, H-$5_a$), 1.15 (m, 1 H, H-$4_a$), 1.32 (m, 1 H, H-$6_a$), 1.43-1.55 (m, 3 H, H-$5_b$, H-$6_b$, H-$4_b$), 1.81 (m, 1 H, H-3), 2.66 (s, 1 H, OH), 2.91 (ddd, $^3J$=3.9, 8.6, 11.3 Hz, 1 H, H-1), 3.51 (t, $^3J$=9.3 Hz, 1 H, H-2), 5.02 (A of ABX, $^3J_{A,X}$=10.4 Hz, $^2J_{A,B}$=1.7 Hz, $^3J_{A,3}$=0.7 Hz, 1 H, vinyl $H_A$), 5.04 (B of ABX, $^3J_{B,X}$=17.2 Hz, $^2J_{A,B}$=1.7 Hz, $^3J_{B,3}$=1.1 Hz, 1 H, vinyl $H_B$), 5.83 (X of ABX, $^3J_{A,X}$=10.4 Hz, $^3J_{B,X}$=17.2 Hz, $^3J_{Z,3}$=7.6 Hz, 1 H, vinyl $H_X$), 7.21-7.31, 7.48-7.50 (2 m, 15 H, 3 $C_6H_5$); $^{13}$C-NMR ($CDCl_3$, 125.8 MHz) δ: 23.18 (C-5), 30.39 (C-4), 32.21 (C-6), 47.30 (C-3), 76.74 (C-2), 78.53 (C-1), 114.77 (vinyl C), 127.11, 127.77, 128.75, 145.07 (18 C, 3 $C_6H_5$), 140.57 (vinyl C); IR (film on NaCl) v: 3577 (m, OH), 3059 (m), 2932 (vs), 2860 (s), 1641 (vw), 1597 (vw), 1489 (s), 1448 (s), 1278 (m), 1225 (m), 1152 (w), 1064 (vs), 991 (s), 915 (m) cm$^{−1}$; elemental analysis calcd (%) for $C_{27}H_{28}O_2$ (384.51): C 84.34, H 7.34; found: C 84.15, H 7.33.

[(1R,2R,3R)-3-Ethenyl-1-hydroxy-cyclohex-2-yl]2,3,4-tris-O-benzyl-6-deoxy-α-L-galactopyranoside (A-IV)

According to general procedure B, A-III (205 mg, 0.428 mmol) in $CH_2Cl_2$ (1.5 mL) was treated with a solution of $Br_2$ (25.5 μL, 0.496 mmol) in $CH_2Cl_2$ (1 mL) for 40 min at 0° C. After destroying the excess of bromine, the fucosyl bromide solution was added to a solution of A-II (126 mg, 0.329 mmol) and $Et_4NBr$ (90.8 mg, 0.432 mmol) in $DMF/CH_2Cl_2$ (6 mL, 1:1), which has been stirred with activated 3 Å molecular sieves (500 mg) for 4 h. The reaction was stirred for 67 h at r.t. and then quenched with pyridine (1 mL). Work-up and purification according to general procedure B yielded the tritylether (213 mg). To a stirred solution of the tritylether in $CH_2Cl_2$ (4 mL), $ZnBr_2$ (179 mg, 0.793 mmol) and triethylsilane (63 μL, 0.397 mmol) were added. The reaction was quenched after 2 h by adding $H_2O$ (100 μL). Work-up and purification according to general procedure B yielded A-IV (110 mg, 60% over two steps) as a colorless solid.

$[α]_D^{21}$=−22.1 (c=0.52, $CHCl_3$); $^1$H-NMR ($CDCl_3$, 500.1 MHz) δ: 1.15 (d, $^3J_{F6,F5}$=6.5 Hz, 3 H, Fuc H-6), 1.17 (m, 1 H, H-4$_a$), 1.26-1.30 (m, 2 H, H-5$_a$, H-6$_a$), 1.72 (m, 1 H, H-5$_b$), 1.78 (m, 1 H, H-4$_b$), 2.02 (m, 1 H, H-6$_b$), 2.13 (m, 1 H, H-3), 3.04 (t, $^3J$=9.5 Hz, 1 H, H-2), 3.45 (m, 1 H, H-1), 3.69 (m, 1 H, Fuc H-4), 3.98 (dd, $^3J_{F3,F4}$=2.6 Hz, $^3J_{F2,F3}$=10.1 Hz, 1 H, Fuc H-3), 4.10 (dd, $^3J_{F1,F2}$=3.6 Hz, $^3J_{F2,F3}$=10.1 Hz, 1 H, Fuc H-2), 4.12 (m, 1 H, Fuc H-5), 4.65, 4.70, 4.76, 4.78, (4 m, 4 H, 2 $CH_2Ph$), 4.85 (m, 2 H, $CH_2Ph$, vinyl H), 4.98 (m, 1 H, vinyl H), 4.99 (m, 1H, $CH_2Ph$), 5.03 (d, $^3J_{F1,F2}$=3.6 Hz, 1 H, Fuc H-1), 6.25 (m, 1 H, vinyl H), 7.27-7.40 (m, 15 H, 3 $C_6H_5$); $^{13}$C-NMR ($CDCl_3$, 125.8 MHz) δ: 16.55 (Fuc C-6), 22.81 (C-5), 29.67 (C-4), 32.39 (C-6), 44.33 (C-3), 67.56 (Fuc C-5), 72.97, 73.01 ($CH_2Ph$, C-1), 73.38, 74.85 (2 $CH_2Ph$), 76.41 (Fuc C-2), 77.54 (Fuc C-4), 78.86 (Fuc C-3), 90.26 (C-2), 97.98 (Fuc C-1), 113.46 (vinyl C), 127.43, 127.48, 127.53, 127.63, 127.82, 128.23, 128.36 (18 C, 3 $C_6H_5$), 140.43 (vinyl C), IR (KBr) ν: 3429 (s, OH), 3065 (w), 3031 (w), 2932 (s), 2866 (s), 1636 (vw), 1497 (w), 1454 (m), 1348 (m), 1308 (w), 1246 (vw), 1212 (w), 1161 (s), 1138 (s), 1101 (vs), 1064 (vs), 1027 (vs), 953 (m), 911 (w) $cm^{-1}$; elemental analysis calcd (%) for $C_{35}H_{42}O_6$ (558.70): C 75.24, H 7.58; found: C 74.91, H 7.55.

[(1R,2R,3S)-3-Ethyl-1-hydroxy-cyclohex-2-yl]2,3,4-tris-O-benzyl-6-deoxy-α-L-galactopyranoside (A-V)

A solution of A-IV (90.0 mg, 0.161 mmol) in THF (4 mL) was added to Pd/C (45.2 mg, 10% Pd) under argon. The mixture was hydrogenated under atmospheric pressure at r.t. After 30 min the reaction was filtered through celite, concentrated under reduced pressure and purified by column chromatography (toluene/petroleum ether/ethyl acetate, 7:7:1 to 5:5:1) to yield A-V (69.8 mg, 77%) as a colorless solid.

$[α]_D^{21}$=−37.2 (c=0.50, $CHCl_3$); $^1$H-NMR ($CDCl_3$, 500.1 MHz) δ: 0.78 (t, $^3J$=7.5 Hz, 3 H, $CH_2CH_3$), 0.88 (m, 1 H, H-4$_a$), 1.06-1.26 (m, 3 H, $CH_2CH_3$, H-5$_a$, H-6$_a$), 1.16 (d, $^3J_{F5,F6}$=6.5 Hz, 3 H, Fuc H-6), 1.30 (m, 1 H, H-3), 1.67 (m, 1 H, H-5$_b$), 1.79 (m, 1 H, H-4$_b$), 1.99-2.07 (m, 2 H, H-6$_b$, $CH_2CH_3$), 2.96 (dd, $^3J$=8.6, 10.2 Hz, 1 H, H-2), 3.38 (ddd, $^3J$=4.8, 8.5, 10.6 Hz, 1 H, H-1), 3.70 (m, 1 H, Fuc H-4), 3.98 (dd, $^3J_{F3,F4}$=2.7 Hz, $^3J_{F3,F2}$=10.2 Hz, 1 H, Fuc H-5), 4.10-4.14 (m, 2 H, Fuc H-2, Fuc H-5), 4.66, 4.70, 4.77, 4.80, 4.84 (5 m, 5 H, $CH_2Ph$), 4.89-5.00 (m, 2 H, Fuc H-1, $CH_2Ph$), 7.27-7.40 (m, 15 H, 3 $C_6H_5$); $^{13}$C-NMR ($CDCl_3$, 125.8 MHz) δ: 10.99 ($CH_2CH_3$), 16.60 (Fuc C-6), 23.09 (C-5), 24.17 ($CH_2CH_3$), 29.50 (C-4), 32.60 (C-6), 42.64 (C-3), 67.48 (Fuc C-5), 72.83, 73.13, 73.47 (C-1, 2 $CH_2Ph$), 74.84 ($CH_2Ph$), 76.32 (Fuc C-2), 77.37 (Fuc C-4), 78.86 (Fuc C-3), 91.07 (C-2), 98.31 (Fuc C-1), 127.40, 127.46, 127.50, 127.64, 127.80, 128.21, 128.33, 128.39, 138.31, 138.39, 138.70 (18 C, 3 $C_6H_5$); HR-MS (ESI) m/z: calcd for $C_{35}H_{44}NaO_6$ [M+Na]$^+$: 583.3030; found: 583.3018 (2.1 ppm).

{(1R,2R,3S)-2-[(2,3,4-tris-O-benzyl-6-deoxy-α-L-galactopyranosyl)oxy]-3-ethyl-cyclohex-1-yl}2,4,6-tri-O-benzoyl-3-O-[(1S)-1-benzyloxycarbonyl-2-cyclohexyl-ethyl]-β-D-galactopyranoside (A-VII)

According to general procedure C, thioglycoside A-VI (112 mg, 0.144 mmol) and glycosyl acceptor A-V (61.6 mg, 0.110 mmol) in dry $CH_2Cl_2$ (4 mL) were added via syringe to activated 3 Å molecular sieves (1 g). A suspension of DMTST (87.0 mg, 0.337 mmol) and activated 3 Å molecular sieves (500 mg) in $CH_2Cl_2$ (2 mL) was prepared in a second flask. Both suspensions were stirred at r.t. for 4 h, then the DMTST suspension was added via syringe to the other suspension with some additional $CH_2Cl_2$ (1 mL). The reaction was stopped after 49.5 h and work-up and purification according to general procedure C afforded A-VII (110 mg, 78%) as a colorless foam.

$[α]_D^{21}$=−51.5 (c=0.42, $CHCl_3$); $^1$H-NMR ($CDCl_3$, 500.1 MHz) δ: 0.45-1.61 (m, 20 H, $CyCH_2$, EtCy), 0.75 (t, $^3J$=7.3 Hz, 3 H, $CH_2CH_3$), 1.41 (d, $^3J_{F5,F6}$=6.4 Hz, 3 H, Fuc H-6), 1.84 (m, 1 H, H-6$_b$), 1.92 (m, 1 H, $CH_2CH_3$), 3.31 (t, $^3J$=8.7 Hz, 1 H, H-2), 3.49-3.52 (m, 2 H, H-1, Fuc H-4), 3.82 (dd, $^3J_{G3,G4}$=3.2 Hz, $^3J_{G2,G3}$=9.8 Hz, 1 H, Gal H-3), 3.92 (m, 1 H, Gal H-5), 3.99-4.05 (m, 2 H, Fuc H-2, Fuc H-3), 4.12 (dd, $^3J$=4.6, 7.9 Hz, 1 H, Lac H-2), 4.25 (dd, $^3J_{G5,G6a}$=7.2 Hz, $^3J_{G6a,G6b}$=11.4 Hz, 1 H, Gal H-6$_a$), 4.28 (m, 1 H, $CH_2Ph$), 4.39 (dd, $^3J_{G5,G6b}$=5.7 Hz, $^3J_{G6a,G6b}$=11.4 Hz, 1 H, Gal H-6$_b$), 4.51-4.55 (m, 2 H, $CH_2Ph$, Gal H-1), 4.63, 4.65, 4.75, 4.78 (4 m, 4 H, $CH_2Ph$), 4.81 (m, 1 H, Fuc H-5), 4.98 (d, $^3J_{F1,F2}$=2.8 Hz, 1 H, Fuc H-1), 5.04, 5.11 (2 m, 2 H, $CH_2Ph$), 5.60 (m, 1 H, Gal H-2), 5.84 (m, 1 H, Gal H-4), 7.17-7.33, 7.42-7.46, 7.52-7.58, 8.04-8.12 (4 m, 35 H, 7 $C_6H_5$); $^{13}$C-NMR ($CDCl_3$, 125.8 MHz) δ: 10.94 ($CH_2CH_3$), 16.82 (Fuc C-6), 23.18 ($CH_2CH_3$), 22.11, 25.45, 25.71, 26.07, 27.89, 30.41, 32.60, 33.19, 33.40, 40.49 (10 C, EtCy, $CyCH_2$), 44.71 (C-3), 62.50 (Gal C-6), 66.35 (Fuc C-5), 66.64 ($CH_2Ph$), 70.17 (Gal C-4), 71.40 (Gal C-5), 72.07 ($CH_2Ph$), 72.17 (Gal C-2), 74.29, 74.91 (2 $CH_2Ph$), 76.42 (Fuc C-2), 78.06 (Gal C-3), 78.38 (Lac C-2), 79.22, 79.27 (Fuc C-4, C-2), 79.77 (Fuc C-3), 80.95 (C-1), 97.96 (Fuc C-1), 100.05 (Gal C-1), 126.94, 127.06, 127.21, 127.39, 127.77, 128.05, 128.10, 128.38, 128.44, 128.50, 128.54, 129.66, 129.93, 133.03, 133.17, 133.27, 135.40, 138.64, 139.01, 139.17 (42 C, 7 $C_6H_5$), 164.58, 166.11, 166.22, 172.48 (4 C=O); elemental analysis calcd (%) for $C_{78}H_{86}O_{16}$ (1279.51)+½$H_2O$: C 72.20, H 6.84; found: C 72.37, H 6.82; HR-MS (ESI) m/z: calcd for $C_{78}H_{86}NaO_{16}$ [M+Na]$^+$: 1301.5808; found: 1301.5855 (3.6 ppm).

{(1R,2R,3S)-2-[(6-deoxy-α-L-galactopyranosyl)oxy]-3-ethyl-cyclohex-1-yl}2-O-benzyl-3-O-[(1S)-1-carboxy-2-cyclohexyl-ethyl]-β-D-galactopyranoside (A-VIII: FIG. 3)

A-VII (38.2 mg, 29.9 μmol) was hydrogenated with Pd(OH)$_2$/C (50 mg, 10% Pd) in dioxane/$H_2O$ (4:1, 3.75 mL) according to general procedure D. After 24 h the reaction mixture was filtered through celite and evaporated to dryness. The residue was redissolved in methanol (5 mL) and sodium methoxide (74.6 μmol in 73 μl MeOH) was added. After stirring at r.t. for 16 h the reaction was quenched by addition of acetic acid (8.5 μL). The mixture was concentrated in vacuo and purified by preparative, reversed-phase HPLC to afford A-VIII (16.3 mg, 77%) as a colorless solid.

$[\alpha]_D^{21}$=−89.3 (c=0.47, MeOH); $^1$H-NMR (MeOD, δ500.1 MHz) δ: 0.55-1.69 (m, 20 H, CyCH$_2$, EtCy), 0.83 (t, $^3J$=7.3 Hz, 3 H, CH$_2$CH$_3$), 1.32 (d, $^3J$=6.6 Hz, 3 H, Fuc H-6), 1.90 (m, 1 H, CH$_2$CH$_3$), 1.99 (m, 1 H, H-6$_b$), 3.24 (t, $^3J$=8.9 Hz, 1 H, H-2), 3.57 (m, 1 H, Gal H-5), 3.62 (m, 1 H, H-1), 3.67 (dd, $^3J_{G3,G4}$=3.0 Hz, $^3J_{G2,G3}$=9.8 Hz, 1 H, Gal H-3), 3.70-3.75 (m, 3 H, Gal H-6$_a$, Fuc H-2, Fuc H-4), 3.79 (dd, $^3J_{G5,G6b}$=6.9 Hz, $^2J_{G6a,G6b}$=11.3 Hz, 1 H, Gal H-6$_b$), 3.86 (dd, $^3J_{F3,F4}$=3.3 Hz, $^3J_{F2,F3}$=10.3 Hz, 1 H, Fuc H-3), 3.97 (m, 1 H, Gal H-4), 4.07 (dd, $^3J$=3.0, 9.8 Hz, 1 H, Lac H-2), 4.67 (d, $^3J_{G1,G2}$=8.1 Hz, 1 H, Gal H-1), 4.90 (m, 1 H, Fuc H-5), 4.91 (m, 1 H, Fuc H-1), 5.43 (dd, $^3J_{G1,G2}$=8.3 Hz, $^3J_{G2,G3}$=9.4 Hz, 1 H, Gal H-2), 7.49-7.52, 7.61-7.64, 8.08-8.09 (3 m, 5 H, C$_6$H$_5$); $^{13}$C-NMR (MeOD, 125.8 MHz) δ: 11.12 (CH$_2$CH$_3$), 16.72 (Fuc C-6), 23.39, 24.59, 26.54, 26.72, 27.27, 29.47, 31.86, 33.14, 34.20, 35.06, 42.76 (11 C, EtCy, CH$_2$Cy), 45.96 (C-3), 62.68 (Gal C-6), 67.77 (Fuc C-5), 67.83 (Gal C-4), 70.30 (Fuc C-2), 71.38 (Fuc C-3), 73.12 (Gal C-2), 73.92 (Fuc C-4), 75.90 (Gal C-5), 77.94 (Lac C-2), 80.77 (C-1), 81.11 (C-2), 83.55 (Gal C-3), 100.20 (Fuc C-1), 100.52 (Gal C-1), 129.67, 130.84, 131.63, 134.37 (6 C, C$_6$H$_5$), 166.79 (C=O), 178.76 (CO$_2$H); HR-MS (ESI) m/z: calcd for C$_{36}$H$_{54}$NaO$_{14}$ [M+Na]$^+$: 733.3406; found: 733.3409 (0.4 ppm).

Example 4

Figure 4:
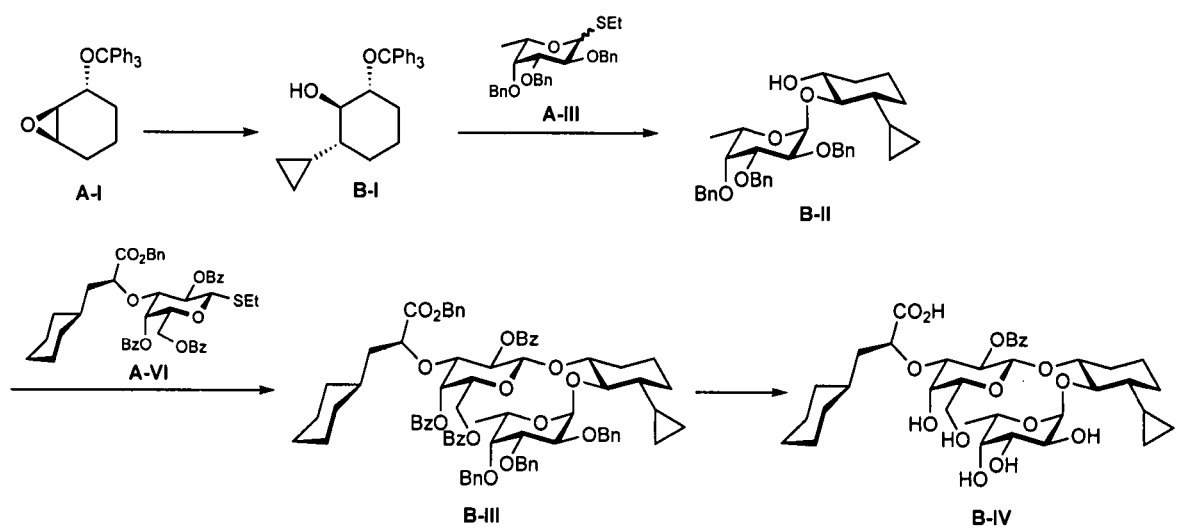
FIG. 4 is a diagram illustrating the synthesis of mimics.

{(1R,2R,3R)-3-Cyclopropyl-2-[(6-Deoxy-α-L-Galactopyranosyl)Oxy]-Cyclohex-1-yl}2-O-Benzoyl-3-O-[(1S)-1-Carboxy-2-Cyclohexyl-Ethyl]-β-D-Galactopyranoside (B-IV; FIG. 4)

(1R,2R,3R)-3-Cyclopropyl-1-O-triphenylmethyl-cyclohexane-1,2-diol (B-I)

A cPrLi solution was generated in situ by treating a solution of bromocyclopropane (370 μL, 4.63 mmol) in THF (4 mL) with tBuLi (1.7 M in pentane, 5.45 mL, 9.27 mmol) during 80 min at −78° C. CuCN (210 mg, 2.34 mmol) in THF (5 mL) was treated with the cPrLi solution and BF$_3$ etherate (115 μL, 0.914 mmol) in THF (1 mL) according to general procedure A. Epoxide A-I (165 mg, 0.463 mmol) in THF (5 mL) was slowly added and the reaction slowly warmed to −30° C. (−78° C.: 1.5 h; −78° C. to −50° C.: 1.5 h; −50°: 24 h; −50° C. to −30° C.: 40 min). Work-up and purification according to general procedure A yielded B-I (150.7 mg, 82%).

$[\alpha]_D^{21}$=−38.8 (c=0.50, CH$_2$Cl$_2$); $^1$H-NMR (CD$_2$Cl$_2$, 500.1 MHz) δ: −0.16 (m, 1 H, cPr), 0.13-0.23 (m, 2 H, cPr), 0.34-0.43 (m, 2 H, cPr, H-3), 0.54-0.67 (m, 2 H, cPr, H-5$_a$), 0.91 (m, 1 H, H-4$_a$), 1.18 (m, 1 H, H-6$_a$), 1.27-1.35 (m, 2 H, H-5$_b$, H-6$_b$), 1.44 (m 1 H, H-4$_b$), 2.52 (s, 1 H, OH), 2.71 (ddd, $^3J$=4.1, 8.6, 11.0 Hz, 1H, H-1), 3.47 (t, $^3J$=9.1 Hz, 1 H, H-2), 7.15-7.23, 7.42-7.43 (2 m, 15 H, 3 C$_6$H$_5$); $^{13}$C-NMR (CD$_2$Cl$_2$, 125.8 MHz) δ: 0.85, 4.26, 14.56 (3 C, cPr), 23.11 (C-5), 29.50 (C-4), 32.15 (C-6), 46.68 (C-3), 78.55 (C-2), 78.92 (C-1), 86.37 (OCPh$_3$), 127.07, 127.73, 128.82, 145.37 (18 C, 3 C$_6$H$_5$); IR (KBr) v: 3571 (m, OH), 3058 (w), 2930 (m), 2858 (m), 1596 (vw), 1490 (m), 1448 (s), 1284 (w), 1225 (w), 1152 (w), 1063 (vs), 926 (w), 844 (vw), 824 (vw), 761 (m), 746 (m), 707 (vs) cm$^{-1}$; elemental analysis calcd (%) for C$_{28}$H$_{30}$O$_2$ (398.54): C 84.38, H 7.59; found: C 84.16, H 7.78.

[(1R,2R,3R)-3-Cyclopropyl-1-hydroxy-cyclohex-2-yl]2,3,4-tris-O-benzyl-6-deoxy-α-L-galactopyranoside (B-II)

According to general procedure B, A-III (223 mg, 0.466 mmol) in CH$_2$Cl$_2$ (1.5 mL) was treated with a solution of Br$_2$ (27.5 μL, 0.535 mmol) in CH$_2$Cl$_2$ (1 mL) for 30 min at 0° C. After destroying the excess of bromine, the fucosyl bromide solution was added to a solution of B-I (142 mg, 0.356 mmol) and Et$_4$NBr (98.9 mg, 0.471 mmol) in DMF/CH$_2$Cl$_2$ (6 mL, 1:1), which has been stirred with activated 3 Å molecular sieves (1 g) for 4 h. The reaction was stirred for 67 h at r.t. and then quenched with pyridine (1 mL). Work-up and purification according to general procedure B yielded the tritylether (237 mg). To a stirred solution of the tritylether in CH$_2$Cl$_2$ (4 mL), ZnBr$_2$ (193 mg, 0.859 mmol) and triethylsilane (70 μL, 0.441 mmol) were added. The reaction was quenched after 1.75 h by adding H$_2$O (100 μL). Work-up and purification according to general procedure B yielded B-II (136 mg, 67% over two steps) as a colorless solid.

$[\alpha]_D^{21}$=−29.0 (c=0.65, CHCl$_3$); $^1$H-NMR (CDCl$_3$, 500.1 MHz) δ: −0.06 (m, 1 H, cPr), 0.08 (m, 1 H, cPr), 0.22 (m, 1 H, cPr), 0.33 (m, 1 H, cPr), 0.87 (m, 1 H, H-4$_a$), 0.96 (m, 1 H, cPr), 1.05-1.27 (m, 6 H, Fuc H-6, H-3, H-5$_a$, H-6$_a$), 1.54 (m, 1 H, H-4$_b$), 1.64 (m, 1 H, H-5$_b$), 1.96 (m, 1 H, H-6$_b$), 3.11 (t, $^3J$=9.1 Hz, 1 H, H-2), 3.35 (m, 1 H, H-1), 3.69 (m, 1 H, Fuc H-4), 3.98 (dd, $^3J_{F3,F4}$=2.5 Hz, $^3J_{F2,F3}$=10.1 Hz, 1 H, Fuc H-3), 4.11-4.16 (m, 2 H, Fuc H-2, Fuc H-5), 4.66-4.68 (m, 2 H, CH$_2$Ph), 4.76, 4.77, 4.90, 5.01 (4 m, 4 H, CH$_2$Ph), 5.14 (d, $^3J_{F1,F2}$=3.4 Hz, 1H, Fuc H-1), 7.26-7.41 (m, 15 H, 3 C$_6$H$_5$); $^{13}$C-NMR (CDCl$_3$, 125.8 MHz) δ: 0.76, 4.93, 13.58 (3 C, cPr), 16.56 (Fuc C-6), 22.86 (C-5), 28.32 (C-4), 32.56 (C-6), 44.14 (C-3), 67.64 (Fuc C-5), 73.14, 73.19 (2 CH$_2$Ph), 73.95 (C-1), 74.85 (CH$_2$Ph), 76.74 (Fuc C-2), 77.68 (Fuc C-4), 78.63 (Fuc C-3), 92.33 (C-2), 99.20 (Fuc C-1), 127.42, 127.45, 127.50, 127.64, 128.18, 128.22, 128.35, 128.44, 138.44, 138.58, 138.90 (18 C, 3 C$_6$H$_5$); IR (KBr) v: 3426 (s, OH), 3031 (vw), 3004 (vw), 2933 (s), 1497 (vw), 1453 (m), 1348 (w), 1247 (vw), 1212 (vw), 1161 (m), 1136 (s), 1103 (vs), 1064 (vs), 1026 (vs), 957 (w), 911 (vw), 843 (vw), 736 (s), 696 (s) cm$^{-1}$; elemental analysis calcd (%) for C$_{36}$H$_{44}$O$_6$ (572.73): C 75.50, H 7.74; found: C 75.38, H 7.75.

{(1R,2R,3R)-2-[(2,3,4-tris-O-benzyl-6-deoxy-α-L-galactopyranosyl)oxy]-3-cyclopropyl-cyclohex-1-yl}2,4,6-tri-O-benzyl-3-O-[(1S)-1-benzyloxycarbonyl-2-cyclohexyl-ethyl]-β-D-galactopyranoside (B-III)

According to general procedure C, thioglycoside A-VI (228 mg, 0.292 mmol) and glycosyl acceptor B-II (129 mg, 0.225 mmol) in dry CH$_2$Cl$_2$ (8 mL) were added via syringe to activated 3 Å molecular sieves (2 g). A suspension of DMTST (177 mg, 0.685 mmol) and activated 3 Å molecular sieves (1 g) in CH$_2$Cl$_2$ (4 mL) was prepared in a second flask. Both suspensions were stirred at r.t. for 4 h, then the DMTST suspension was added via syringe to the other suspension with some additional CH$_2$Cl$_2$ (2 mL). The reaction was stopped after 48 h and work-up and purification according to general procedure C afforded B-III (253 mg, 87%) as a colorless foam.

$[\alpha]_D^{21}$=−43.1 (c=0.61, CHCl$_3$); $^1$H-NMR (CDCl$_3$, 500.1 MHz) δ: −0.11 (m, 1 H, cPr), 0.16 (m, 1 H, cPr), 0.32-0.35 (m, 2 H, cPr), 0.46-0.53 (m, 2 H, CyCH$_2$), 0.64-1.46 (m, 18 H, CyCH$_2$, Cy, cPr), 1.38 (d, $^3J_{F5,F6}$=6.4 Hz, 3 H, Fuc H-6), 1.80 (m, 1 H, H-6$_b$), 3.52 (t, $^3J$=7.3 Hz, 1 H, H-2), 3.57 (s, 1 H, Fuc H-4), 3.62 (m, 1 H, H-1), 3.84 (dd, $^3J_{G3,G4}$=2.8

Hz, $^3J_{G2,G3}$=9.8 Hz, 1 H, Gal H-3), 3.93 (m, 1 H, Gal H-5), 4.03 (dd, $^3J_{F1,F2}$=3.2 Hz, $^3J_{F2,F3}$=10.2 Hz, 1 H, Fuc H-2), 4.07 (dd, $^3J_{F3,F4}$=1.7 Hz, $^3J_{F2,F3}$=10.4 Hz, 1 H, Fuc H-3), 4.13 (dd, $^3J$=4.5, 7.8 Hz, 1 H, Lac H-2), 4.32-4.40 (m, 3 H, Gal H-6, CH$_2$Ph), 4.53 (m, 1 H, CH$_2$Ph), 4.58 (d, $^3J_{G1,G2}$=8.1 Hz, 1 H, Gal H-1), 4.62, 4.68 (2 m, 2 H, CH$_2$Ph), 4.74-4.76 (m, 2 H, Fuc H-5, CH$_2$Ph), 4.78 (m, 1 H, CH$_2$Ph), 5.05, 5.11 (2 m, 2 H, CH$_2$Ph), 5.35 (d, $^3J_{F1,F2}$=2.8 Hz, 1 H, Fuc H-1), 5.61 (m, 1 H, Gal H-2), 5.87 (m, 1 H, Gal H-4), 7.20-7.36, 7.42-7.44, 7.52-7.59, 8.03-8.14 (4 m, 35 H, 7 C$_6$H$_5$); $^{13}$C-NMR (CDCl$_3$, 125.8 MHz) δ: 3.06 (cPr), 5.26 (cPr), 13.55 (cPr), 16.81 (Fuc C-6), 20.97, 25.46, 25.72, 26.07, 27.71, 29.44, 32.62, 33.21, 33.40 (9 C, CyCH$_2$, Cy), 40.46 (Lac C-3), 45.35 (C-3), 62.50 (Gal C-6), 66.34 (Fuc C-5), 66.61 (CH$_2$Ph), 70.10 (Gal C-4), 71.49 (Gal C-5), 72.13 (CH$_2$Ph), 72.32 (Gal C-2), 74.22 (CH$_2$Ph), 74.87 (CH$_2$Ph), 76.15 (Fuc C-2), 77.97 (Gal C-3), 78.38 (Lac C-2), 78.82 (C-2), 79.13 (Fuc C-4), 79.66 (C-1), 79.83 (Fuc C-3), 97.02 (Fuc C-1), 99.60 (Gal C-1), 126.96, 127.05, 127.20, 127.38, 127.78, 128.05, 128.09, 128.37, 128.43, 128.47, 128.53, 129.61, 129.73, 129.89, 129.93, 129.96, 133.03, 133.16, 133.23, 135.44, 138.51, 138.95, 139.21 (42 C, 7 C$_6$H$_5$), 164.57, 165.98, 166.16, 172.43 (4 C=O); IR (KBr) ν: 3064 (vw), 3032 (vw), 2927 (s), 2854 (w), 1731 (vs, C=O), 1602 (vw), 1497 (vw), 1452 (m), 1315 (m), 1267 (vs), 1176 (s), 1097 (vs), 1027 (vs), 840 (vw), 713 (vs) cm$^{-1}$; elemental analysis calcd (%) for C$_{79}$H$_{86}$O$_{16}$ (1291.52): C 73.47, H 6.71; found: C 73.32, H 6.81.

{(1R,2R,3R)-3-cyclopropyl-2-[(6-deoxy-α-L-galactopyranosyl)oxy]-cyclohex-1-yl}2-O-benzoyl-3-O-[(1S)-1-carboxy-2-cyclohexyl-ethyl]-β-D-galactopyranoside (B-IV; FIG. 4)

B-III (100 mg, 77.7 µmol) was hydrogenated with Pd(OH)$_2$/C (52 mg, 10% Pd) in dioxane/H$_2$O (4:1, 3.75 mL) according to general procedure D. After 24 h the mixture was filtered through celite and hydrogenated with fresh Pd(OH)$_2$/C (50 mg) for another 48 h. The reaction mixture was filtered through celite and evaporated to dryness. The residue was redissolved in methanol (5 mL) and sodium methoxide (194 µmol in 190 µl MeOH) was added. After stirring at r.t. for 16 h the reaction was quenched by addition of acetic acid (22 µL). The mixture was concentrated in vacuo and purified by preparative, reversed-phase HPLC to afford B-IV (40.5 mg, 72%) as a colorless solid.

$[\alpha]_D^{21}$=−85.4 (c=0.75, MeOH); $^1$H-NMR (MeOD, 500.1 MHz) δ: −0.04 (m, 1 H, cPr), 0.33 (m, 1 H, cPr), 0.45-0.52 (m, 2 H, cPr), 0.56-1.65 (m, 20 H, CyCH$_2$, cPrCy), 1.30 (d, $^3J_{F5,F6}$=6.6 Hz, 3 H, Fuc H-6), 1.94 (m, 1 H, H-6$_b$), 3.45 (t, $^3J$=8.5 Hz, 1 H, H-2), 3.56 (m, 1 H, Gal H-5), 3.62 (m, 1 H, H-1), 3.66 (dd, $^3J_{G3,G4}$=3.1 Hz, $^3J_{G2,G3}$=9.8 Hz, 1 H, Gal H-3), 3.71-3.74 (m, 2 H, Gal H-6$_a$, Fuc H-2), 3.78 (m, 1 H, Fuc H-4), 3.83 (dd, $^3J_{G5,G6b}$=7.1 Hz, $^2J_{G6a,G6b}$=11.4 Hz, 1 H, Gal H-6$_b$), 3.95 (dd, $^3J_{F3,F4}$=3.3 Hz, $^3J_{F2,F3}$=10.2 Hz, 1 H, Fuc H-3), 3.97 (m, 1 H, Gal H-4), 4.06 (dd, $^3J$=2.9, 9.8 Hz, 1 H, Lac H-2), 4.66 (d, $^3J_{G1,G2}$=8.0 Hz, 1 H, Gal H-1), 4.88 (m, 1 H, Fuc H-5), 5.37 (d, $^3J_{F1,F2}$=3.9 Hz, 1 H, Fuc H-1), 5.39 (dd, $^3J_{G1,G2}$=8.1 Hz, $^3J_{G2,G3}$=9.6 Hz, 1 H, Gal H-2), 7.49-7.52, 7.61-7.65, 8.07-8.09 (3 m, 5 H, C$_6$H$_5$); $^{13}$C-NMR (MeOD, 125.8 MHz) δ: 3.96, 7.18, 15.53 (3 C, cPr), 16.72 (Fuc C-6), 22.94, 26.54, 26.73, 27.27, 30.78, 31.45 (6 C, CyCH$_2$, Cy), 33.13, 34.20, 35.07, 42.76 (4 C, CyCH$_2$), 48.49 (C-3), 62.72 (Gal C-6), 67.61 (Fuc C-5), 67.88 (Gal C-5), 70.24 (Fuc C-2), 71.34 (Fuc C-3), 73.16 (Gal C-2), 73.97 (Fuc C-4), 76.02 (Gal C-5), 78.01 (Lac C-2), 80.29 (C-1), 80.52 (C-2), 83.45 (Gal C-3), 98.97 (Fuc C-1), 100.41 (Gal C-1), 129.66, 130.82, 131.63, 134.36 (6 C, C$_6$H$_5$), 166.76 (C=O), 178.83 (CO$_2$H); HR-MS (ESI) m/z: calcd for C$_{37}$H$_{54}$NaO$_{14}$ [M+Na]$^+$: 745.3406; found: 745.3407 (0.1 ppm).

Example 5

Figure 5:
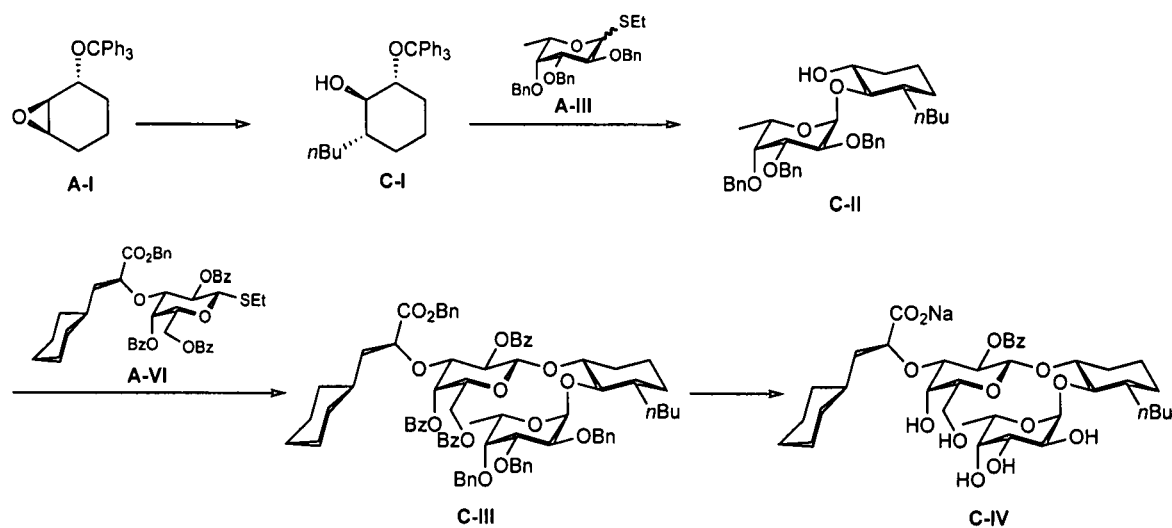
FIG. 5 is a diagram illustrating the synthesis of mimics.

{(1R,2R,3S)-3-Butyl-2-[(6-Deoxy-α-L-Galactopyranosyl)Oxy]-Cyclohex-1-yl}2-O-Benzoyl-3-O-[(1S)-1-Carboxy-2-Cyclohexyl-Ethyl]-β-D-Galactopyranoside Sodium Salt (C-IV; FIG. 5)

(1R,2R,3S)-3-Butyl-1-O-triphenylmethyl-cyclohexane-1,2-diol (C-I)

CuCN (342 mg, 3.81 mmol) in THF (10 mL) was treated with nBuLi (2.5 M in hexane, 3.05 mL, 7.63 mmol) and BF$_3$ etherate (192 µL, 1.53 mmol) in THF (2 mL) according to general procedure A. Epoxide A-I (271 mg, 0.761 mmol) in THF (8 mL) was slowly added and the reaction slowly warmed to −30° C. (−78° C.: 1 h; −78° C. to −50° C.: 4 h; −50°: 24 h; −50° C. to −30° C.: 21 h). Work-up and purification according to general procedure A yielded C-I (220 mg, 70%).

$[\alpha]_D^{21}$=−37.8 (c=0.66, CHCl$_3$); $^1$H-NMR (CDCl$_3$, 500.1 MHz) δ: 0.73 (m, 1 H, H-5$_a$), 0.85 (m, 1 H, H-4$_a$), 0.86 (t, $^3J$=7.2 Hz, 3 H, H-10), 1.03-1.16 (m, 3 H, H-3, H-7$_a$, H-8$_a$), 1.21-1.35 (m, 4 H, H-6$_a$, H-8$_b$, H-9$_a$, H-9$_b$), 1.38-1.49 (m, 2 H, H-5$_b$, H-6$_b$), 1.61 (m, 1 H, H-4$_b$), 1.75 (m, 1 H, H-7$_b$), 2.70 (s, 1 H, OH), 2.82 (ddd, $^3J$=4.0, 8.6, 11.2 Hz, 1 H, H-1), 3.40 (t, $^3J$=9.0 Hz, 1 H, H-2), 7.21-7.30, 7.48-7.50 (2 m, 15 H, 3 C$_6$H$_5$); $^{13}$C-NMR (CDCl$_3$, 125.8 MHz) δ: 14.11 (C-10), 23.10 (C-9), 23.37 (C-5), 28.73 (C-8), 29.38 (C-4), 32.05 (C-7), 32.30 (C-6), 42.45 (C-3), 77.62 (C-2), 79.05 (C-1), 86.43 (CPh$_3$), 127.05, 127.74, 128.70, 145.12 (18 C, 3 C$_6$H$_5$); elemental analysis calcd (%) for C$_{29}$H$_{34}$O$_2$ (414.58): C 84.02, H 8.27; found: C 84.05, H 8.27.

[(1R,2R,3S)-3-Butyl-1-hydroxy-cyclohex-2-yl]2,3,4-tris-O-benzyl-6-deoxy-α-L-galactopyranoside (C-II)

According to general procedure B, A-III (308 mg, 0.644 mmol) in CH$_2$Cl$_2$ (3 mL) was treated with a solution of Br$_2$ (38 µL, 0.740 mmol) in CH$_2$Cl$_2$ (1 mL) for 30 min at 0° C. After destroying the excess of bromine, the fucosyl bromide solution was added to a solution of C-I (205 mg, 0.495 mmol) and Et$_4$NBr (137 mg, 0.650 mmol) in DMF/CH$_2$Cl$_2$ (10 mL, 1:1), which has been stirred with activated 3 Å molecular sieves (700 mg) for 3.5 h. The reaction was stirred for 67 h at r.t. and then quenched with pyridine (1 mL). Work-up and purification according to the general procedure B yielded the tritylether (283 mg) as a yellowish resin. To a stirred solution of the tritylether in CH$_2$Cl$_2$ (4 mL), ZnBr$_2$ (229 mg, 1.02 mmol) and triethylsilane (81 µL, 0.510 mmol) were added. The reaction was quenched after 1.25 h by adding H$_2$O (100 µL). Work-up and purification according to general procedure B yielded C-II (161 mg, 55% over two steps) as a colorless solid.

$[\alpha]_D^{21}$=−21.3 (c=0.56, CHCl$_3$); $^1$H-NMR (CDCl$_3$, 500.1 MHz) δ: 0.82 (t, $^3J$=7.0 Hz, 3 H, H-10), 0.86 (m, 1 H, H-4$_a$), 0.98 (m, 1 H, H-7$_a$), 1.15 (d, $^3J_{F5,F6}$=6.5 Hz, 3 H, Fuc H-6), 1.09-1.37 (m, 7 H, H-3, H-5$_a$, H-6$_a$, H-8$_a$, H-8$_b$, H-9$_a$, H-9$_b$), 1.66 (m, 1 H, H-5$_b$), 1.81 (m, 1 H, H-4$_b$), 1.98 (m, 1 H, H-6$_b$), 2.10 (m, 1 H, H-7$_b$), 2.94 (t, $^3J$=9.3 Hz, 1 H, H-2), 3.36 (m, 1 H, H-1), 3.68 (m, 1 H, Fuc H-4), 3.98 (dd, $^3J_{F3,F4}$=2.6 Hz, $^3J_{F2,F3}$=10.2 Hz, 1 H, Fuc H-3), 4.09-4.14 (m, 2 H, Fuc H-2, Fuc H-5), 4.65, 4.70, 4.75, 4.78, 4.85 (5 m, 5 H, 3 CH$_2$Ph), 4.98-5.00 (m, 2 H, Fuc H-1, 1 CH$_2$Ph), 7.25-7.39 (m, 15 H, 3 C$_6$H$_5$); $^{13}$C-NMR (CDCl$_3$, 125.8 MHz) δ: 14.11 (C-10), 16.57 (Fuc C-6), 22.72 (C-9), 23.19 (C-8), 29.03 (C-8), 30.26 (C-4), 31.24 (C-7), 32.55 (C-6), 41.18 (C-3), 67.54 (Fuc C-5), 72.97 (CH$_2$Ph), 73.26 (C-1), 73.39 (CH$_2$Ph), 74.84 (CH$_2$Ph), 76.38 (Fuc C-2), 77.60 (Fuc C-4), 78.80 (Fuc C-3), 91.47 (C-2), 98.31 (Fuc C-1), 127.40, 127.45, 127.52, 127.61, 127.86, 128.20, 128.21, 128.33, 128.38, 138.32, 138.44, 138.79 (18 C, 3 C$_6$H$_5$); elemental analysis calcd (%) for C$_{37}$H$_{48}$O$_6$ (588.77): C 75.48, H 8.22; found: C 75.55, H 8.28.

{(1R,2R,3S)-2-[(2,3,4-tris-O-benzyl-6-deoxy-α-L-galactopyranosyl)oxy]-3-butyl-cyclohex-1-yl}2,4,6-tri-O-benzyl-3-O-[(1S)-1-benzyloxycarbonyl-2-cyclohexyl-ethyl]-β-D-galactopyranoside (C-III)

According to general procedure C, thioglycoside A-VI (218 mg, 0.279 mmol) and glycosyl acceptor C-II (126 mg, 0.215 mmol) in dry CH$_2$Cl$_2$ (8 mL) were added via syringe to activated 3 Å molecular sieves (2 g). A suspension of DMTST (166 mg, 0.644 mmol) and activated 3 Å molecular sieves (1 g) in CH$_2$Cl$_2$ (4 mL) was prepared in a second flask. Both suspensions were stirred at r.t. for 4.5 h, then the DMTST suspension was added via syringe to the other suspension with some additional CH$_2$Cl$_2$ (2 mL). The reaction was stopped after 65.5 h and work-up and purification according to general procedure C afforded C-III (224 mg, 80%) as a colorless foam.

[α]$_D$$^{21}$=−46.7 (c=0.49, CHCl$_3$); $^1$H-NMR (CDCl$_3$, 500.1 MHz) δ: 0.45-1.84 (m, 26 H, CyCH$_2$, nBuCy), 0.80 (d, $^3$J=6.8 Hz, 3 H, nBu), 1.40 (d, $^3$J=6.5 Hz, 3 H, Fuc H-6), 3.36 (t, $^3$J=8.5 Hz, 1 H, H-2), 3.52 (s, 1 H, Fuc H-4), 3.54 (m, 1 H, H-1), 3.83 (dd, $^3$J$_{G3,G4}$=3.0 Hz, $^3$J$_{G2,G3}$=9.8 Hz, 1 H, Gal H-3), 3.92 (m, 1 H, Gal H-5), 4.01 (dd, $^3$J$_{F1,F2}$=3.2 Hz, $^3$J$_{F2,F3}$=10.3 Hz, 1 H, Fuc H-2), 4.04 (dd, $^3$J$_{F3,F4}$=2.0 Hz, $^3$J$_{F2,F3}$=10.4 Hz, 1 H, Fuc H-3), 4.13 (dd, $^3$J=4.6, 7.8 Hz, 1 H, Lac H-2), 4.28 (dd, $^3$J$_{G5,G6a}$=6.7 Hz, $^2$J$_{G6a,G6b}$=11.4 Hz, 1 H, Gal H-6$_a$), 4.28 (m, 1 H, CH$_2$Ph), 4.39 (dd, $^3$J$_{G5,G6b}$=5.8 Hz, $^2$J$_{G6a,G6b}$=11.4 Hz, 1 H, Gal H-6$_b$), 4.52 (m, 1H, CH$_2$Ph), 4.56 (d, $^3$J$_{G1,G2}$=8.1 Hz, 1 H, Gal H-1), 4.65, 4.68, 4.74, 4.76 (4 m, 4 H, CH$_2$Ph), 4.79 (m, 1 H, Fuc H-5), 5.01 (d, $^3$J$_{F1,F2}$=3.0 Hz, 1 H, Fuc H-1), 5.05, 5.11 (2 m, 2 H, CH$_2$Ph), 5.61 (m, 1 H, Gal H-2), 5.85 (m, 1 H, Gal H-4), 7.20-7.36, 7.42-7.46, 7.52-7.59, 8.04-8.13 (4 m, 35 H, 7 C$_6$H$_5$); $^{13}$C-NMR (CDCl$_3$, 125.8 MHz) δ: 14.26 (CH$_2$CH$_2$CH$_2$CH$_3$), 16.81 (Fuc C-6), 21.84, 22.95, 25.46, 25.71, 26.07, 28.34, 28.55, 30.20, 30.39, 32.61, 33.19, 33.39, 40.48, 42.80 (14 C, CyCH$_2$, nBuCy), 62.52 (Gal C-6), 66.37 (Fuc C-5), 66.63 (CH$_2$Ph), 70.15 (Gal C-4), 71.45 (Gal C-5), 72.11 (CH$_2$Ph), 72.21 (Gal C-2), 73.89, 74.92 (2 CH$_2$Ph), 76.17 (Fuc C-2), 78.05 (Gal C-3), 78.38 (Lac C-2), 78.76 (C-2), 79.23 (Fuc C-4), 79.75 (Fuc C-3), 80.79 (C-1), 97.71 (Fuc C-1), 100.03 (Gal C-1), 126.95, 127.04, 127.21, 127.30, 127.80, 128.04, 128.09, 128.15, 128.39, 128.44, 128.48, 128.49, 128.54, 129.66, 129.71, 129.75, 129.92, 129.94, 133.03, 133.16, 133.25, 135.42, 138.70, 138.99, 139.16 (42 C, 7 C$_6$H$_5$), 164.56, 166.09, 166.21, 172.47 (4 C=O); elemental analysis calcd (%) for C$_{80}$H$_{90}$O$_{16}$ (1307.58): C 73.49, H 6.94; found: C 73.16, H 6.93.

{(1R,2R,3S)-3-butyl-2-[(6-deoxy-X-L-galactopyranosyl)oxy]-cyclohex-1-yl}2-O-benzoyl-3-O-[(1S)-1-carboxy-2-cyclohexyl-ethyl]-β-D-galactopyranoside sodium salt (C-IV: FIG. 5)

C-III (100 mg, 76.5 µmol) was hydrogenated with Pd(OH)$_2$/C (50 mg, 10% Pd) in dioxane/H$_2$O (4:1, 3.75 mL) according to general procedure D. After 19 h the mixture was filtered through celite and hydrogenated with fresh Pd(OH)$_2$/C (50 mg) for another 30 h. The reaction mixture was filtered through celite and evaporated to dryness. The residue was redissolved in methanol (5 mL) and sodium methoxide (0.191 mmol) was added. After stirring at r.t. for 17 h the reaction was quenched by addition of acetic acid (22 µL). The mixture was concentrated in vacuo and purified by column chromatography (CH$_2$Cl$_2$/methanol/water, 3.4:1:0.1 to 2:1:0.1), followed by Dowex 50 (Na$^+$ form) ion exchange column, Sephadex G15 column, microfiltration and lyophilization from dioxane to give C-IV (32.3 mg, 56%) as a colorless foam. For biological testing a small amount was purified by preparative, reversed-phase HPLC to afford the free acid of C-IV as colorless needles.

C-IV sodium salt: [α]$_D$$^{21}$=−77.9 (c=0.61, MeOH); $^1$H-NMR (MeOD, 500.1 MHz) δ: 0.47-1.89 (m, 25 H, CyCH$_2$, nBu, Cy), 0.88 (t, $^3$J=7.1 Hz, 3 H, nBu), 1.31 (d, $^3$J=6.5 Hz, 3 H, Fuc H-6), 2.00 (m, 1 H, H-6$_b$), 3.24 (t, $^3$J=8.9 Hz, 1 H, H-2), 3.56-3.60 (m, 2 H, Gal H-5, Gal H-3), 3.65 (m, 1 H, H-1), 3.72-3.77 (m, 4 H, Gal H-6$_a$, Fuc H-2, Fuc H-4, Lac H-2), 3.80 (dd, $^3$J$_{G5,G6b}$=6.9 Hz, $^2$J$_{G6a,G6b}$=11.5 Hz, 1 H, Gal H-6$_b$), 3.88 (dd, $^3$J$_{F3,F4}$=3.3 Hz, $^3$J$_{F2,F3}$=10.3 Hz, 1 H, Fuc H-3), 3.95 (m, 1 H, Gal H-4), 4.68 (d, $^3$J$_{G1,G2}$=8.1 Hz, 1 H, Gal H-1), 4.85 (m, 1H, Fuc H-5), 4.94 (d, $^3$J$_{F1,F2}$=4.0 Hz, 1 H, Fuc H-1), 5.41 (dd, $^3$J$_{G1,G2}$=8.5 Hz, $^3$J$_{G2,G3}$=9.2 Hz, 1 H, Gal H-2), 7.48-7.51, 7.60-7.63, 8.07-8.09 (3 m, 5 H, C$_6$H$_5$); $^{13}$C-NMR (MeOD, 125.8 MHz) δ: 14.48 (nBu), 16.72 (Fuc C-6), 23.27, 23.92, 26.57, 26.82, 27.41, 29.83, 30.04, 31.69, 31.86, 33.06, 34.44, 35.41, 43.54, 44.30 (14 C, nBu, Cy, CH$_2$CY), 63.06 (Gal C-6), 67.70 (Gal C-4), 67.84 (Fuc C-5), 70.21 (Fuc C-2), 71.34 (Fuc C-3), 73.08 (Gal C-2), 73.90 (Fuc C-4), 75.92 (Gal C-5), 80.69 (Lac C-2), 80.41 (C-1), 81.37 (C-2), 83.69 (Gal C-3), 99.91 (Fuc C-1), 100.53 (Gal C-1), 129.60, 130.84, 131.76, 134.23 (6 C, C$_6$H$_5$), 166.87 (C=O), 183.26 (COOH); HR-MS (ESI) m/z: calcd for C$_{38}$H$_{58}$NaO$_{14}$ [M+H]$^+$: 761.3719; found: 761.3710 (1.2 ppm).

C-IV free acid: $^1$H-NMR (MeOD, 500.1 MHz) δ: 0.54-1.91 (m, 25 H, CyCH$_2$, nBu, Cy), 0.89 (t, $^3$J=7.1 Hz, 3 H, nBu), 1.32 (d, $^3$J=6.6 Hz, 3 H, Fuc H-6), 1.98 (m, 1 H, H-6$_b$), 3.23 (t, $^3$J=8.9 Hz, 1 H, H-2), 3.56 (m, 1 H, Gal H-5), 3.62 (m, 1 H, H-1), 3.66 (dd, $^3$J$_{G3,G4}$=3.0 Hz, $^3$J$_{G2,G3}$=9.8 Hz, 1 H, Gal H-3), 3.70-3.75 (m, 3 H, Gal H-6$_a$, Fuc H-2, Fuc H-4), 3.79 (dd, $^3$J$_{G6b,G5}$=6.9 Hz, $^2$J$_{G6a,G6b}$=11.3 Hz, 1 H, Gal H-6$_b$), 3.85 (dd, $^3$J$_{F3,F4}$=3.3 Hz, $^3$J$_{F2,F3}$=10.3 Hz, 1 H, Fuc H-3), 3.97 (m, 1 H, Gal H-4), 4.06 (dd, $^3$J=2.9, 9.9 Hz, 1 H, Lac H-2), 4.67 (d, $^3$J$_{G1,G2}$=8.1 Hz, 1 H, Gal H-1), 4.88-4.92 (m, 2 H, Fuc H-1, Fuc H-5), 5.43 (dd, $^3$J$_{G1,G2}$=8.2 Hz, $^3$J$_{G2,G3}$=9.6 Hz, 1 H, Gal H-2), 7.49-7.52, 7.62-7.64, 8.07-8.09 (3 m, 5 H, C$_6$H$_5$); $^{13}$C-NMR (MeOD, 125.8 MHz) δ: 14.48 (nBu), 16.74 (Fuc C-6), 23.38, 23.90, 26.54, 26.72, 27.28, 29.83, 29.99, 31.71, 31.81, 33.12, 34.19, 35.07, 42.78, 44.51 (14 C, nBu, Cy, CH$_2$Cy), 62.69 (Gal C-6), 67.79 (2 C, Fuc C-5, Gal C-4), 70.27 (Fuc C-2), 71.43 (Fuc C-3), 73.10 (Gal C-2), 73.94 (Fuc C-4), 75.90 (Gal C-5), 77.93 (Lac C-2), 80.71 (C-1), 81.45 (C-2), 83.57 (Gal C-3), 100.29 (Fuc C-1), 100.52 (Gal C-1), 129.67, 130.85, 131.63, 134.37 (6 C, C$_6$H$_5$), 166.77 (C=O), 178.84 (CO$_2$H).

Example 6

Figure 6:
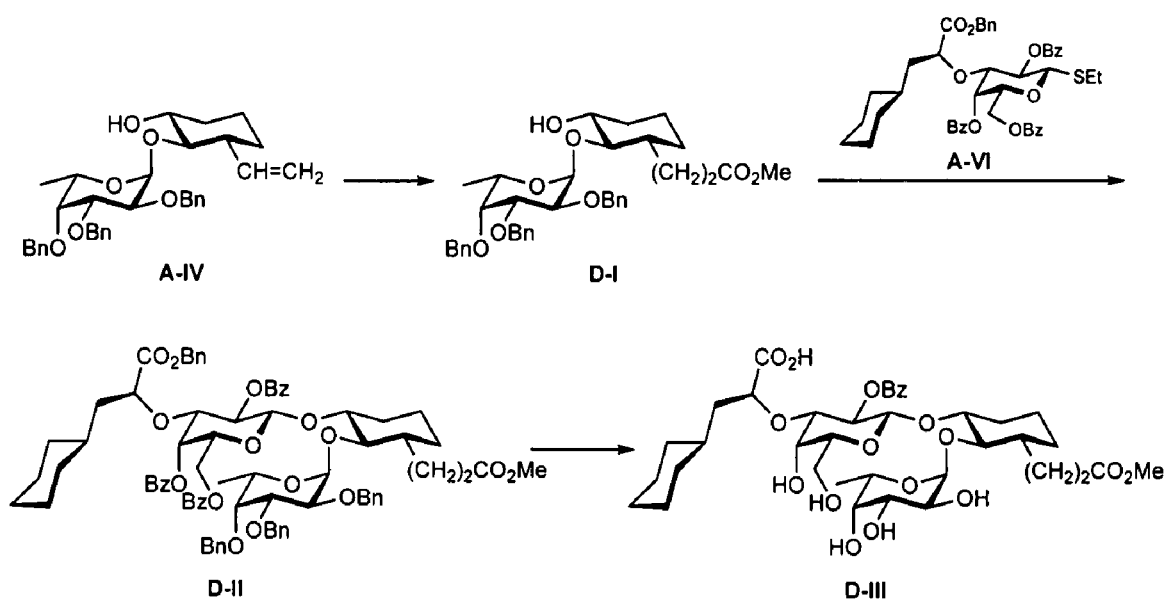
FIG. 6 is a diagram illustrating the synthesis of mimics.

{(1R,2R,3R)-2-[(6-Deoxy-α-L-galactopyranosyl)oxy]-3-(2-methoxycarbonyl-ethyl)-cyclohex-1-yl}2-O-Benzoyl-3-O-[(1S)-1-Carboxy-2-Cyclohexyl-Ethyl]-β-D-Galactopyranoside (D-III; FIG. 6)

[(1R,2R,3R)-1-Hydroxy-3-(2-methoxycarbonyl-ethyl)-cyclohex-2-yl]2,3,4-tris-O-benzyl-6-deoxy-α-L-galactopyranoside (D-I)

A-IV (106 mg, 0.189 mmol) was dissolved in $CH_2Cl_2$ (5 mL) and Grubbs cat. $2^{nd}$ gen. (16.0 mg 18.8 µmol) and methyl acrylate (171 µL, 1.90 mmol) were added. The reaction was heated under reflux for 9 d. After 1 d, 2 d and 7 d additional Grubbs cat. $2^{nd}$ gen. (each 16.0 mg, 18.8 µmol) and methyl acrylate (each 171 µL, 1.90 mmol) were added. The mixture was concentrated under reduced pressure and purified by column chromatography (petroleum ether/ethyl acetate, 5:1 to 4:1) to yield an E/Z mixture (53.9 mg), which was directly used for hydrogenation. A solution of the E/Z-mixture in THF (4 mL) was added to Pd/C (28.0 mg, 10% Pd) under argon. The mixture was hydrogenated under atmospheric pressure at r.t. After 30 min the reaction was filtered through celite, concentrated under reduced pressure and purified by column chromatography (petroleum ether/ethyl acetate, 3:1 to 2:1) to yield D-I (29.1 mg, 25%) as a brownish oil.

$[\alpha]_D^{21}$=−21.2 (c=1.46, $CHCl_3$); $^1$H-NMR ($CDCl_3$, 500.1 MHz) δ: 0.94 (m, 1 H), 1.14 (d, $^3J_{F6,F5}$=6.5 Hz, 3 H, Fuc H-6), 1.19-1.28 (m, 2 H), 1.35-1.47 (m, 2 H), 1.67 (m, 1 H), 1.74 (m, 1 H), 1.99 (m, 1 H), 2.29-2.36 (m, 3 H), 2.97 (t, $^3J$=9.2 Hz, 1 H, H-2), 3.36 (m, 1 H, H-1), 3.57 (s, 3 H, Me), 3.67 (m, 1 H, Fuc H-4), 3.98 (dd, $^3J_{F3,F4}$=2.4 Hz, $^3J_{F2,F3}$=10.2 Hz, 1 H, Fuc H-3), 4.09-4.13 (m, 2 H, Fuc H-2, Fuc H-5), 4.65, 4.71, 4.76, 4.78, 4.85 (5 m, 5 H, $CH_2Ph$), 4.96 (d, $^3J_{F1,F2}$=3.4 Hz, 1 H, Fuc H-1), 4.99 (1 m, 1 H, $CH_2Ph$), 7.25-7.41 (m, 15 H, 3 $C_6H_5$); $^{13}$C-NMR ($CDCl_3$, 125.8 MHz) δ: 16.50 (Fuc C-6), 23.03, 27.48, 30.37, 32.02, 32.33 (5 C), 40.72 (C-3), 51.30 (Me), 67.64 (Fuc C-5), 72.97, 73.00 ($CH_2Ph$, C-1), 73.48, 74.82 (2 $CH_2Ph$), 76.01 (Fuc C-2), 77.50 (Fuc C-4), 78.84 (Fuc C-3), 91.25 (C-2), 98.33 (Fuc C-1), 127.43, 127.47, 127.58, 127.62, 127.92, 128.19, 128.28, 128.34, 128.36, 138.23, 138.36, 138.73 (18 C, 3 $C_6H_5$), 174.33 (COOMe); HR-MS (ESI) m/z: calcd for $C_{37}H_{46}NaO_8$ $[M+Na]^+$: 641.3085; found: 641.3080 (0.8 ppm).

{(1R,2R,3R)-2-[(2,3,4-tris-O-benzyl-6-deoxy-α-L-galactopyranosyl)oxy]-3-(2-methoxycarbonyl-ethyl)-cyclohex-1-yl}2,4,6-tri-O-benzyl-3-O-[(1S)-1-benzyloxycarbonyl-2-cyclohexyl-ethyl]-β-D-galactopyranoside (D-II)

According to general procedure C, thioglycoside A-VI (47.9 mg, 61.3 µmol) and glycosyl acceptor D-I (29.1 mg, 47.0 µmol) in dry $CH_2Cl_2$ (4 mL) were added via syringe to activated 3 Å molecular sieves (500 mg). A suspension of DMTST (37.6 mg, 146 µmol) and activated 3 Å molecular sieves (250 mg) in $CH_2Cl_2$ (2 mL) was prepared in a second flask. Both suspensions were stirred at r.t. for 4 h, then the DMTST suspension was added via syringe to the other suspension with some additional $CH_2Cl_2$ (1 mL). The reaction was stopped after 65.5 h and work-up according to general procedure C and purification by column chromatography (petroleum ether/ethyl acetate, 4:1 to 3:1) afforded D-III (49.5 mg, 79%) as a colorless foam.

$[\alpha]_D^{21}$=−38.1 (c=0.59, $CHCl_3$); $^1$H-NMR ($CDCl_3$, 500.1 MHz) δ: 0.45-1.57 (m, 19 H, $CyCH_2$, Cy), 1.37 (d, $^3J$=6.4 Hz, 3 H, Fuc H-6), 1.61 (m, 1 H, $(CH_2)_2CO_2Me$), 1.82 (m, 1 H, H-6$_b$), 2.13-2.26 (m, 3 H, $(CH_2)_2CO_2Me$), 3.39 (t, $^3J$=8.1 Hz, 1 H, H-2), 3.51 (s, 1 H, Fuc H-4), 3.53-3.56 (m, 4 H, H-1, Me), 3.84 (dd, $^3J_{G3,G4}$=3.3 Hz, $^3J_{G2,G3}$=9.9 Hz, 1 H, Gal H-3), 3.93 (m, 1 H, Gal H-5), 3.98-4.03 (m, 2 H, Fuc H-2, Fuc H-3), 4.13 (dd, $^3J$=4.5, 8.0 Hz, 1 H, Lac H-2), 4.28 (dd, $^3J_{G5,G6a}$=7.2 Hz, $^2J_{G6a,G6b}$=11.4 Hz, 1 H, Gal H-6$_a$), 4.31 (m, 1 H, $CH_2Ph$), 4.38 (dd, $^3J_{G5,G6b}$=5.6 Hz, $^2J_{G6a,G6b}$=11.4 Hz, 1 H, Gal H-6$_b$), 4.54 (m, 1 H, $CH_2Ph$), 4.55 (d, $^3J_{G1,G2}$=8.0 Hz, 1 H, Gal H-1), 4.66-4.71 (m, 3 H, $CH_2Ph$, Fuc H-5), 4.73, 4.77 (2 m, 2 H, $CH_2Ph$), 5.02 (d, $^3J_{F1,F2}$=2.3 Hz, 1 H, Fuc H-1), 5.05, 5.12 (2 m, 2 H, $CH_2Ph$), 5.60 (m, 1 H, Gal H-2), 5.85 (m, 1 H, Gal H-4), 7.19-7.34, 7.42-7.47, 7.53-7.59, 8.03-8.13 (4 m, 35 H, 7 $C_6H_5$); $^{13}$C-NMR ($CDCl_3$, 125.8 MHz) δ: 16.78 (Fuc C-6), 21.18, 25.44, 25.66, 25.70, 26.05, 27.84, 31.26, 32.57, 33.19, 33.38, 40.45 (12 C, $CyCH_2$, Cy, $(CH_2)_2CO_2Me$), 41.94 (C-3), 51.42 ($CO_2Me$), 62.54 (Gal C-6), 66.50 (Fuc C-5), 66.62 ($CH_2Ph$), 70.09 (Gal C-4), 71.48 (Gal C-5), 72.24 (2 C, $CH_2Ph$, Gal C-2), 73.79, 74.90 (2 $CH_2Ph$), 76.26 (Fuc C-2), 77.91 (Gal C-3), 78.34, 78.38 (Lac C-2, C-2), 79.09 (Fuc C-4), 79.53 (Fuc C-3), 80.22 (C-1), 97.70 (Fuc C-1) 99.93 (Gal C-1), 126.96, 127.06, 127.23, 127.29, 127.83, 128.04, 128.06, 128.08, 128.15, 128.38, 128.44, 128.48, 128.53, 128.57, 129.62, 129.65, 129.69, 129.74, 129.86, 129.88, 129.94, 129.99, 133.05, 133.19, 133.24, 135.39, 138.64, 138.99, 139.07 (42 C, 7 $C_6H_5$), 164.55, 166.06, 166.17, 172.45, 174.02 (5 C=O); elemental analysis calcd (%) for $C_{80}H_{88}O_{18}$ (1337.54): C 71.84, H 6.63; found: C 71.70, H 6.73.

{(1R,2R,3R)-2-[(6-deoxy-α-L-galactopyranosyl)oxy]-3-(2-methoxycarbonyl-ethyl)-cyclohex-1-yl}2-O-benzyl-3-O-[(1S)-1-carboxy-2-cyclohexyl-ethyl]-β-D-galactopyranoside (D-III: FIG. 6).

D-III (46.0 mg, 34.4 µmol) was hydrogenated with $Pd(OH)_2/C$ (25 mg, 10% Pd) in dioxane/$H_2O$ (4:1, 3.75 mL) according to general procedure D. After 42 h the mixture was filtered through celite and hydrogenated with fresh $Pd(OH)_2/C$ (27 mg) for additional 24 h. The reaction mixture was filtered through celite and evaporated to dryness. The residue was redissolved in methanol (3 mL) and sodium methoxide (51.6 µmol in 55 µl MeOH) was added. After stirring at r.t. for 16 h the reaction was quenched by addition of acetic acid (6 µL). The mixture was concentrated in vacuo and purified by preparative, reversed-phase HPLC to afford D-III (19.2 mg, 73%) as a colorless solid.

$[\alpha]_D^{21}$=−78.3 (c=0.63, MeOH); $^1$H-NMR (MeOD, 500.1 MHz) δ: 0.55-0.75 (m, 4 H, $CyCH_2$), 0.84-0.96 (m, 2 H, $CyCH_2$, H-4$_a$), 1.04 (m, 1 H, H-6$_a$), 1.14 (m, 1 H, H-5$_a$), 1.21-1.36 (m, 5 H, $CyCH_2$), 1.32 (d, $^3J$=6.6 Hz, 3 H, Fuc H-6), 1.39-1.60 (m, 6 H, $CyCH_2$, H-3, H-5$_b$, $(CH_2)_2CO_2Me$), 1.66 (m, 1 H, H-4$_b$), 1.97 (m, 1H, H-6$_b$), 2.18-2.38 (m, 3 H, $CyCH_2$, $(CH_2)_2CO_2Me$), 3.27 (t, $^3J$=8.4 Hz, 1 H, H-2), 3.57 (m, 1 H, Gal H-5), 3.63-3.68 (m, 5 H, $CH_3$, Gal H-3, H-1), 3.71-3.75 (m, 3 H, Gal H-6$_a$, Fuc H-2, Fuc H-4), 3.79 (dd, $^3J_{G5,G6b}$=6.8 Hz, $^2J_{G6a,G6b}$=11.3 Hz, 1 H, Gal H-6$_b$), 3.84 (dd, $^3J_{F3,F4}$=3.3 Hz, $^3J_{F2,F3}$=10.2 Hz, 1 H, Fuc H-3), 3.98 (m, 1 H, Gal H-4), 4.07 (dd, $^3J$=3.0, 9.9 Hz, 1 H, Lac H-2), 4.67 (d, $^3J_{G1,G2}$=8.1 Hz, 1 H, Gal H-1), 4.83 (m, 1 H, Fuc H-5), 4.92 (m, 1 H, Fuc H-1), 5.43 (dd, $^3J_{G1,G2}$=8.2 Hz, $^3J_{G2,G3}$=9.6 Hz, 1 H, Gal H-2), 7.49-7.52, 7.62-7.65, 8.08-8.09 (3 m, 5 H, $C_6H_5$); $^{13}$C-NMR (MeOD, 125.8 MHz) δ: 16.73 (Fuc C-6), 22.77 (C-5), 26.55, 26.73, 27.28, 27.34 (4 C, $CyCH_2$), 29.49 (C-4), 31.34 (C-6), 32.16 ($(CH_2)_2CO_2Me$), 33.13, 34.20, 35.07 (3 C, $CyCH_2$), 42.78 ($(CH_2)_2CO_2Me$), 43.52 (C-3), 52.03 (Me), 62.62 (Gal C-6), 67.81 (Gal C-4), 67.89 (Fuc C-5), 70.25 (Fuc C-2), 71.41 (Fuc C-3), 73.09 (Gal C-2), 73.90 (Fuc C-4), 75.92 (Gal C-5), 77.98 (Lac C-2), 80.36 (C-1), 80.96 (C-2), 83.50 (Gal C-3), 100.34 (Fuc C-1), 100.50 (Gal C-1), 129.68, 130.85, 131.62, 134.39 (6 C, $C_6H_5$), 166.77, 176.09, 178.86 (3 C=O); elemental analysis calcd (%) for $C_{38}H_{56}O_{16}$ (768.84)+1½ $H_2O$: C 57.35, H 7.47; found: C 57.57, H 7.36; HR-MS (ESI) m/z: calcd for $C_{38}H_{56}NaO_{16}$ [M+Na]$^+$: 791.3461; found: 791.3463 (0.3 ppm).

Example 7

Figure 7:
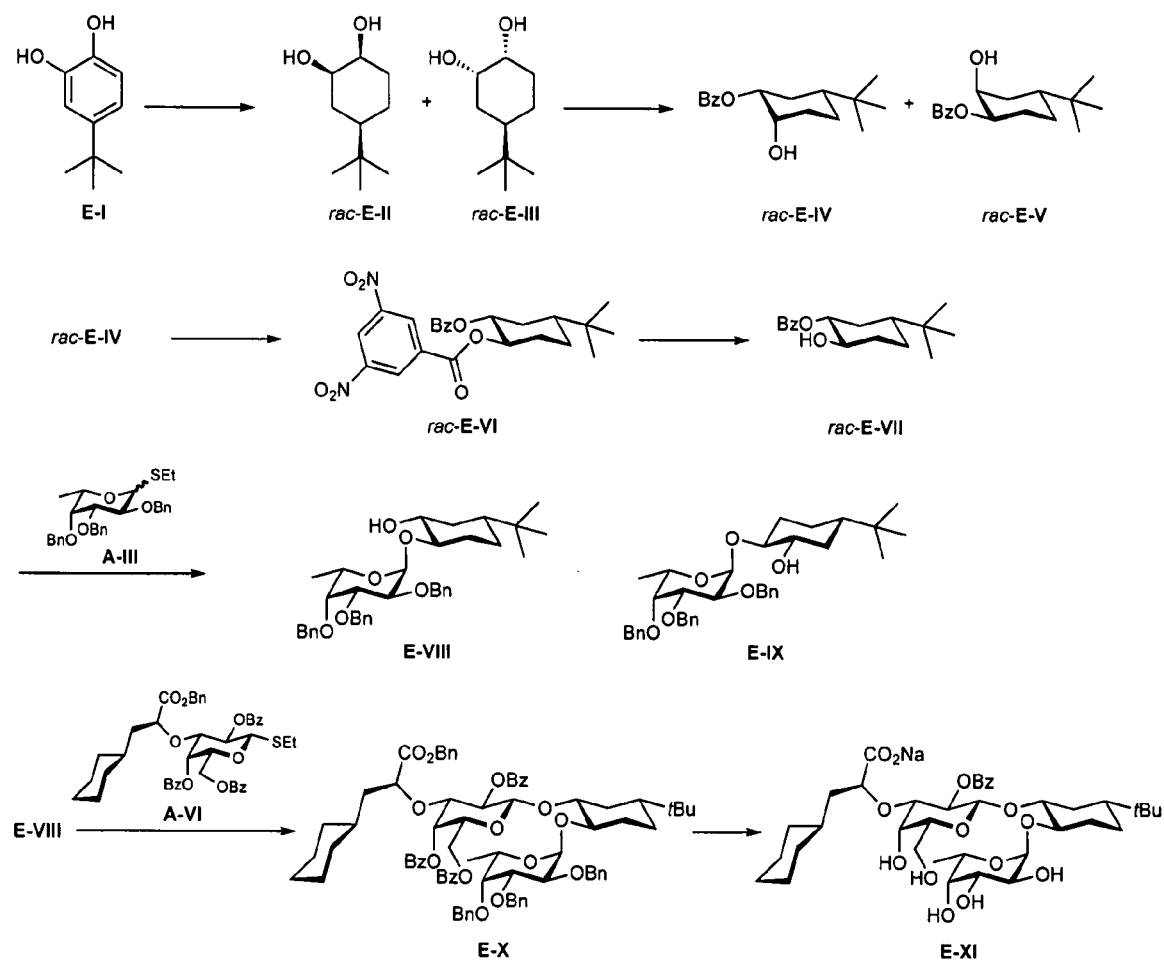
FIG. 7 is a diagram illustrating the synthesis of mimics.

{(1R,2R,5R)-5-Tert-Butyl-2-[(6-Deoxy-α-L-Galactopyranosyl)Oxy]-Cyclohex-1-yl}2-O-Benzoyl-3-O-[(1S)-1-Carboxy-2-Cyclohexyl-Ethyl]-β-D-Galactopyranoside (E-XI; FIG. 7)

rac-(1S,2R,5S)-5-tert-Butyl-2-hydroxycyclohexyl benzoate (rac-E-IV) and rac-(1S,2R,4S)-4-tert-Butyl-2-hydroxycyclohexyl benzoate (rac-E-V)

4-tert-Butylcatechol (E-1) (2.02 g, 12.2 mmol), Rh/$Al_2O_3$ (98.9 mg), cyclohexane (4 mL) and THF (0.5 mL) were hydrogenated under 5 bar at r.t. After 24 h the mixture was filtered through celite and evaporated to dryness. The residue was purified by MPLC on silica ($CH_2Cl_2$/ethyl acetate, 3:1 to 1:3) to afford a mixture of syn-diols (1.64 g, 78%, rac-E-II: rac-E-III, 1.4:1) as a white solid. The mixture (1.64 g, 9.55 mmol) and dibutyltin oxide (2.37 g, 9.52 mmol) were dissolved in $CH_2Cl_2$ (50 mL) and cooled to 0° C. $Et_3N$ (2.68 mL, 19.2 mmol) and benzoyl chloride (1.32 mL, 11.45 mmol) were slowly added via syringe. The mixture was warmed to r.t. during 3 h and then quenched with MeOH (2 mL). The solvents were evaporated in vacuo and the crude residue was purified by MPLC on silica (toluene/ethyl acetate, 10:0 to 10:1) affording rac-E-IV (1.15 g, 44%) and rac-E-V (688 mg, 26%) as white solids.

rac-E-IV: $^1$H-NMR (CDCl$_3$, 500.1 MHz) δ: 0.90 (s, 9 H, tBu), 1.23 (m, 1H, H-5), 1.42 (m, 1 H, H-4$_a$), 1.50-1.57 (m, 2 H, H-3$_a$, H-4$_b$), 1.68 (m, 1 H, H-6$_a$), 1.85 (m, 1 H, H-6$_b$), 2.04 (m, 1 H, H-3$_b$), 4.17 (m, 1 H, H-2), 5.05 (ddd, $^3$J=2.7, 4.7, 11.9 Hz, 1 H, H-1), 7.44-7.47, 7.56-7.59, 8.05-8.07 (3 m, 5 H, $C_6H_5$); $^{13}$C-NMR (CDCl$_3$, 125.8 MHz) δ: 19.59 (C-4), 26.42 (C-6), 27.51 (3 C, tBu), 30.57 (C-3), 32.49 (tBu), 46.35 (C-5), 67.10 (C-2), 76.47 (C-1), 128.39, 129.58, 130.27, 133.07 (6 C, $C_6H_5$), 165.62 (C=O); HR-MS (ESI) m/z: calcd for $C_{17}H_{24}NaO_3$ [M+Na]$^+$: 299.1618; found: 299.1621 (1.0 ppm).

rac-E-V: $^1$H-NMR (CDCl$_3$, 500.1 MHz) δ: 0.89 (s, 9 H, tBu), 1.18 (m, 1 H, H-5$_a$), 1.34 (m, 1 H, H-3$_a$), 1.56 (m, 1 H, H-4), 1.83-1.98 (m, 3 H, H-5$_b$, H-6), 2.04 (m, 1 H, H-3$_b$), 4.25 (m, 1 H, H-2), 4.98 (ddd, $^3$J=2.8, 4.9, 11.7 Hz, 1 H, H-1), 7.44-7.47, 7.56-7.59, 8.04-8.06 (3 m, 5 H, $C_6H_5$); $^{13}$C-NMR (CDCl$_3$, 125.8 MHz) δ: 25.07 (C-5), 25.27 (C-6), 27.48 (3 C, tBu), 31.91 (tBu), 31.98 (C-3), 39.43 (C-4), 68.14 (C-2), 75.87 (C-1), 128.39, 129.58, 130.28, 133.06 (6 C, $C_6H_5$), 165.72 (C=O); HR-MS (ESI) m/z: calcd for $C_{17}H_{24}NaO_3$ [M+Na]$^+$: 299.1618; found: 299.1621 (1.0 ppm).

rac-(1R,2R,4R)-2-(Benzoyloxy)-4-tert-butylcyclohexyl 3,5-dinitrobenzoate (rac-E-VI)

rac-E-IV (400 mg, 1.45 mmol), triphenylphosphine (1.14 g, 4.33 mmol) and 3,5-dinitrobenzoic acid (921 mg, 4.34 mmol) were dissolved in toluene (25 mL). Diethyl azodicarboxylate (680 μL, 4.32 mmol) was slowly added to the reaction via syringe. The mixture was warmed to 50° C. and stirred for 1 d. The solvent was evaporated in vacuo and the residue, redissolved in a small amount of $CH_2Cl_2$, was purified by MPLC on silica (petroleum ether/ethyl acetate, 10:0 to 10:1) affording rac-E-VI (428 mg, 63%) and recovered starting material rac-E-IV (103 mg, 26%) as white solids.

$^1$H-NMR (CDCl$_3$, 500.1 MHz) δ: 0.93 (s, 9 H, tBu), 1.25-1.47 (m, 3 H, H-3$_a$, H-4, H-5$_a$), 1.68 (m, 1 H, H-6$_a$), 1.94 (m, 1 H, H-5$_b$), 2.29-2.35 (m, 2 H, H-3$_b$, H-6$_b$), 5.27 (ddd, $^3$J=4.9, 9.7, 11.4 Hz, 1 H, H-1), 5.35 (ddd, $^3$J=4.7, 9.9, 10.5 Hz, 1H, H-2), 7.36-7.39, 7.48-7.52, 7.96-7.98 (3 m, 5 H, $C_6H_5$), 9.06, 9.14-9.15 (2 m, 3 H, $C_6H_3$); $^{13}$C-NMR (CDCl$_3$, 125.8 MHz) δ: 24.79 (C-5), 27.52 (3 C, tBu), 29.76 (C-6), 31.79 (C-3), 32.36 (tBu), 45.73 (C-4), 74.80 (C-2), 77.55 (C-1), 122.31, 128.39, 129.44, 129.58, 129.74, 133.17, 133.81, 148.54 (12 C, $C_6H_5$, $C_6H_3$), 162.16, 165.89 (2 C=O); HR-MS (ESI) m/z: calcd for $C_{24}H_{26}N_2NaO_8$ [M+Na]$^+$: 493.1581; found: 493.1582 (0.2 ppm).

rac-(1R,2R,5R)-5-tert-Butyl-2-hydroxycyclohexyl benzoate (rac-E-VIII)

rac-E-VI (135 mg, 0.287 mmol) was suspended in MeOH (5 mL). $Et_3N$ (1 mL) was added and the reaction stirred for 1 h. The solvents were evaporated in vacuo and the residue was purified by MPLC on silica (toluene/ethyl acetate, 6:0 to 6:1) affording rac-E-VII (63.2 mg, 80%) as a white solid.

$^1$H-NMR (CDCl$_3$, 500.1 MHz) δ: 0.88 (s, 9 H, tBu), 1.12 (m, 1 H, H-4$_a$), 1.19-1.32 (m, 2 H, H-5, H-6$_a$), 1.41 (m, 1 H, H-3$_a$), 1.80 (m, 1 H, H-4$_b$), 2.12-2.18 (m, 2 H, H-3$_b$, H-6$_b$), 3.69 (ddd, $^3$J=4.9, 9.3, 11.3 Hz, 1 H, H-2), 4.88 (ddd, $^3$J=4.7, 9.4, 10.7 Hz, 1 H, H-1), 7.43-7.46, 7.55-7.58, 8.06-8.07 (3 m, 5 H, $C_6H_5$); $^{13}$C-NMR (CDCl$_3$, 125.8 MHz) δ: 24.89 (C-4), 27.54 (3 C, tBu), 31.44 (C-6), 32.28 (tBu), 32.61 (C-3), 46.01 (C-5), 73.33 (C-2), 79.47 (C-1), 128.34, 129.64, 130.23, 133.05 (6 C, $C_6H_5$), 166.82 (C=O); HR-MS (ESI) m/z: calcd for $C_{17}H_{24}NaO_3$ [M+Na]$^+$: 299.1618; found: 299.1619 (0.3 ppm).

[(1R,2R,5R)-5-tert-Butyl-1-hydroxy-cyclohex-2-yl] 2,3,4-tris-O-benzyl-6-deoxy-α- and β-L-galactopyranoside (E-VIII) and [(1S,2S,5S)-5-tert-Butyl-1-hydroxy-cyclohex-2-yl]2,3,4-tris-O-benzyl-6-deoxy-α-L-galactopyranoside (E-IX)

A mixture of rac-E-VII (76.9 mg, 0.278 mmol), A-VI (202 mg, 0.421 mmol), $Bu_4NBr$ (274 mg, 0.850 mmol) and powdered 4 Å molecular sieves (1 g) in $CH_2Cl_2$ (4 mL) and DMF (1 mL) was stirred at r.t. under argon for 3.5 h. Then, $CuBr_2$ (188 mg, 0.844 mmol) was added and the reaction mixture was stirred at r.t. for 11 h. The reaction mixture was filtered through celite and the filtrate was diluted with $CH_2Cl_2$ (30 mL). The organic layer was successively washed with satd. aqueous $NaHCO_3$ and brine (each 30 mL) and the aqueous layers were extracted with $CH_2Cl_2$ (3×40 mL). The combined organic layers were dried with $Na_2SO_4$, filtered and co-evaporated with toluene to dryness. The residue was purified by MPLC on silica (petroleum ether/$CH_2Cl_2$/diethyl ether, 2:1:0 to 2:1:1) to afford the fucosylated diastereomers. To a stirred solution of these diastereomers in methanol/water (5:1, 6 mL), lithium hydroxide (200 mg) was added and the mixture warmed to 50° C. After stirring for 4 h the reaction mixture was diluted with $CH_2Cl_2$ (30 mL) and the organic layer was washed with brine (50 mL). The aqueous layer was extracted with $CH_2Cl_2$ (3×30 mL), and the combined organic layers were dried with $Na_2SO_4$, filtered and concentrated in vacuo. The residue was purified by MPLC on silica (petroleum ether/ethyl acetate, 4:0 to 4:1) to yield E-VIII (72.1 mg, 44%, α:β=1:0.12, yield over two steps) as an anomeric mixture and E-IX (63.0 mg, 38%, yield over two steps) as pure α-anomer.

α-E-VIII: $[α]_D^{21}$=−41.3 (c=0.31, CHCl$_3$); $^1$H-NMR (CDCl$_3$, 500.1 MHz) δ: 0.86 (s, 9 H, tBu), 0.97-1.38 (m, 7 H, Fuc H-6, H-3$_a$, H-4$_a$, H-5, H-6$_a$), 1.74 (m, 1 H, H-4$_b$), 1.99-2.06 (m, 2 H, H-3$_b$, H-6$_b$), 3.22 (m, 1 H, H-2), 3.47 (m, 1 H, H-1), 3.70 (m, 1 H, Fuc H-4), 3.94 (dd, $^3J_{F3,F4}$=2.4 Hz, $^3J_{F2,F3}$=10.1 Hz, 1 H, Fuc H-3), 4.05-4.09 (m, 2 H, Fuc H-2, Fuc H-5), 4.65, 4.66, 4.75, 4.82, 4.87 (5 m, 5 H, CH$_2$Ph), 4.97-5.00 (m, 2 H, Fuc H-1, CH$_2$Ph), 7.26-7.41 (m, 15 H, 3 C$_6$H$_5$); $^{13}$C-NMR (CDCl$_3$, 125.8 MHz) δ: 16.65 (Fuc C-6), 25.17 (C-4), 27.55 (3 C, tBu), 29.54 (C-3), 32.19 (tBu), 33.63 (C-6), 45.82 (C-5), 66.97 (Fuc C-5), 73.15, 73.33 (2 CH$_2$Ph), 73.52 (C-1), 74.86 (CH$_2$Ph), 76.16 (Fuc C-2), 77.41 (Fuc C-4), 79.21 (Fuc C-3), 84.09 (C-2), 96.33 (Fuc C-1), 127.40, 127.48, 127.64, 127.69, 127.90, 128.21, 128.35, 128.44, 138.41, 138.50, 138.81 (18 C, 3 C$_6$H$_5$); HR-MS (ESI) m/z: calcd for C$_{37}$H$_{48}$NaO$_6$ [M+Na]$^+$: 611.3343; found: 611.3346 (0.5 ppm).

E-IX: $[α]_D^{21}$=−40.7 (c=0.38, CHCl$_3$); $^1$H-NMR (CDCl$_3$, 500.1 MHz) δ: 0.85 (s, 9 H, tBu), 1.01-1.17 (m, 6 H, Fuc H-6, H-4$_a$, H-5, H-6$_a$), 1.29 (m, 1 H, H-3$_a$), 1.70 (m, 1 H, H-4$_b$), 1.97-2.04 (m, 2 H, H-3$_b$, H-6$_b$), 3.17 (m, 1 H, H-2), 3.45 (m, 1 H, H-1), 3.69 (m, 1 H, Fuc H-4), 3.96-4.05 (m, 3 H, Fuc H-2, Fuc H-3, Fuc H-5), 4.66, 4.73, 4.76, 4.81, 4.87, 4.97 (6 m, 6 H, CH$_2$Ph), 4.98 (m, 1 H, Fuc H-1), 7.26-7.41 (m, 15 H, 3 C$_6$H$_5$); $^{13}$C-NMR (CDCl$_3$, 125.8 MHz) δ: 16.69 (Fuc C-6), 25.32 (C-4), 27.58 (3 C, tBu), 31.26 (C-3), 32.25 (tBu), 32.88 (C-6), 45.78 (C-5), 66.57 (Fuc C-5), 72.63, 74.19 (2 CH$_2$Ph), 74.66 (C-1), 74.80 (CH$_2$Ph), 76.33 (Fuc C-2), 77.40 (Fuc C-4), 80.01 (Fuc C-3), 87.22 (C-2), 101.01 (Fuc C-1), 127.34, 127.52, 127.58, 127.84, 128.18, 128.22, 128.34, 128.39, 128.47, 137.95, 138.53, 138.65 (18 C, 3 C$_6$H$_5$).

{(1R,2R,5R)-2-[(2,3,4-tris-O-benzyl-6-deoxy-α-L-galactopyranosyl)oxy]-5-tert-butyl-cyclohex-1-yl}2,4,6-tri-O-benzyl-3-O-[(1S)-1-benzyloxycarbonyl-2-cyclohexyl-ethyl]β-D-galactopyranoside (E-X)

According to general procedure C, thioglycoside A-VI (125 mg, 0.161 mmol) and glycosyl acceptor E-VIII (71.4 mg, 0.121 mmol) in dry CH$_2$Cl$_2$ (4 mL) were added via syringe to activated 4 Å molecular sieves (1 g). A suspension of DMTST (120 mg, 0.465 mmol) and activated 4 Å molecular sieves (500 mg) in CH$_2$Cl$_2$ (2 mL) was prepared in a second flask. Both suspensions were stirred at r.t. for 2 h, before adding the DMTST suspension via syringe to the other suspension with some additional CH$_2$Cl$_2$ (1 mL). The reaction was stopped after 45 h and worked-up according to general procedure C. The crude product was purified by MPLC on silica (toluene/ethyl acetate, 11.5:0 to 11.5:1) to yield E-X (107 mg, 68%) as a colorless foam.

$[α]_D^{21=}$−57.9 (c=0.50, CHCl$_3$); $^1$H-NMR (CDCl$_3$, 500.1 MHz) δ: 0.46-1.43 (3 m, 17 H, CyCH$_2$, Cy), 0.58 (s, 9 H, tBu), 1.36 (d, $^3$J=6.0 Hz, 3 H, Fuc H-6), 1.60 (m, 1 H, H-4$_b$), 1.81 (m, 1 H, H-6$_b$), 1.99 (m, 1 H, H-3$_b$), 3.45 (m, 1 H, H-2), 3.55 (m, 1 H, H-1), 3.58 (s, 1 H, Fuc H-4), 3.87-3.90 (m, 2 H, Gal H-3, Gal H-5), 3.97-4.04 (m, 2 H, Fuc H-2, Fuc H-3), 4.16 (m, 1 H, Lac H-2), 4.29 (m, 2 H, Gal H-6), 4.39 (m, 1 H, CH$_2$Ph), 4.55-4.57 (m, 2 H, Gal H-1, CH$_2$Ph), 4.63 (m, 1 H, CH$_2$Ph), 4.69-4.74 (m, 2 H, CH$_2$Ph), 4.79-4.83 (m, 2 H, Fuc H-5, CH$_2$Ph), 4.88 (d, $^3J_{F1,F2}$=2.1 Hz, 1 H, Fuc H-1), 5.04, 5.13 (2 m, 2 H, CH$_2$Ph), 5.56 (m, 1 H, Gal H-2), 5.91 (m, 1 H, Gal H-4), 7.17-7.35, 7.39-7.48, 7.54-7.55, 8.04-8.11 (m, 35 H, 7 C$_6$H$_5$); $^{13}$C-NMR (CDCl$_3$, 125.8 MHz) δ: 16.62 (Fuc C-6), 24.43 (C-4), 25.40, 25.71, 26.06 (3 C, CyCH$_2$), 27.19 (3 C, tBu), 28.97 (C-3), 31.95 (tBu), 32.23 (C-6), 32.49, 33.17, 33.44 (3 C, CyCH$_2$), 40.44 (CyCH$_2$), 45.50 (C-5), 62.21 (Gal C-6), 65.98 (Fuc C-5), 66.58 (CH$_2$Ph), 69.86 (Gal C-4), 71.19 (Gal C-5), 72.53, 72.56 (Gal C-2, CH$_2$Ph), 73.02 (CH$_2$Ph), 74.90 (CH$_2$Ph), 75.25 (C-2), 76.44 (Fuc C-2), 77.51 (Gal C-3), 78.08 (Lac C-2), 79.24 (Fuc C-4), 79.64 (Fuc C-3), 81.37 (C-1), 94.16 (Fuc C-1), 100.24 (Gal C-1), 126.87, 126.95, 127.22, 127.38, 127.93, 127.95, 128.03, 128.15, 128.34, 128.42, 128.47, 128.50, 129.64, 129.74, 129.83, 129.88, 129.91, 133.04, 133.16, 133.21, 135.43, 138.86, 139.08, 139.14 (42 C, 7 C$_6$H$_5$), 164.56, 165.65, 166.11, 172.47 (4 C=O); elemental analysis calcd (%) for C$_{80}$H$_{90}$O$_{16}$ (1307.56): C 73.48, H 6.94; found: C 73.50, H 6.95.

{(1R,2R,5R)-5-tert-Butyl-2-[(6-deoxy-α-L-galactopyranosyl)oxy]-cyclohex-1-yl}2-O-benzyl-3-O-[(1S)-1-carboxy-2-cyclohexyl-ethyl]-β-D-galactopyranoside (E-XI: FIG. 7)

A mixture of E-X (102 mg, 77.9 μmol), Pd(OH)$_2$/C (49.4 mg), dioxane (3 mL) and water (0.75 mL) was hydrogenated under 4 bar at r.t. After 37 h TLC control indicated completion of the reaction and the mixture was filtered through celite and evaporated to dryness. The residue was redissolved in methanol (5 mL) and sodium methoxide (0.195 mmol in 255 μL MeOH) was added. After stirring at r.t. for 14 h the reaction was quenched by addition of acetic acid (23 μL). The mixture was concentrated in vacuo and purified by preparative, reversed-phase HPLC to afford compound E-XI (50.9 mg, 88%) as a white solid.

$[α]_D^{21}$=−93.2 (c=0.91, MeOH); $^1$H-NMR (MeOD, 500.1 MHz) δ: 0.60-0.77 (m, 5 H, H-6$_a$, CyCH$_2$), 0.65 (s, 9 H, tBu), 0.84 (m, 1 H, H-4$_a$), 0.93 (m, 1 H, CyCH$_2$), 1.01 (m, 1 H, H-5), 1.15 (m, 1 H, H-3$_a$), 1.26 (d, $^3J_{F5,F6}$=6.6 Hz, 3 H, Fuc H-6), 1.29-1.39 (m, 5 H, CyCH$_2$), 1.43 (m, 1 H, CyCH$_2$), 1.53 (m, 1 H, CyCH$_2$), 1.60-1.66 (m, 2 H, H-4$_b$, CyCH$_2$), 1.95 (m, 1 H, H-6$_b$), 2.05 (m, 1 H, H-3$_b$), 3.33 (m, 1H, H-2), 3.56-3.61 (m, 2 H, H-1, Gal H-5), 3.69-3.74 (m, 4 H, Fuc H-2, Fuc H-4, Gal H-3, Gal H-6$_a$), 3.79 (m, $^3J_{G6b,G5}$=6.9 Hz, $^2J_{G6a,G6b}$=11.3 Hz, 1 H, Gal H-6$_b$), 3.91 (dd, $^3J_{F3,F4}$=3.4 Hz, $^3J_{F2,F3}$=10.1 Hz, 1 H, Fuc H-3), 4.00 (m, 1 H, Gal H-4), 4.10 (dd, $^3$J=2.9, 10.0 Hz, 1 H, Lac H-2), 4.67 (d, $^3J_{G1,G2}$=8.0 Hz, 1 H, Gal H-1), 4.77 (m, 1 H, Fuc H-5), 4.82 (d, $^3J_{F1,F2}$=3.8 Hz, 1 H, Fuc H-1), 5.36 (dd, $^3J_{G1,G2}$=8.0 Hz, $^3J_{G2,G3}$=9.8 Hz, 1 H, Gal H-2), 7.49-7.52 (m, 2 H, C$_6$H$_5$), 7.61-7.64 (m, 1 H, C$_6$H$_5$), 8.10-8.12 (m, 2 H, C$_6$H$_5$); $^{13}$C-NMR (MeOD, 125.8 MHz) δ: 16.53 (Fuc C-6), 25.74 (C-4), 26.60, 26.82, 27.30 (3 C, CyCH$_2$), 27.78 (3 C, tBu), 29.73 (C-3), 32.83 (tBu), 33.11 (CyCH$_2$), 33.74 (C-6), 34.26 (Lac C-4), 35.12 (CyCH$_2$), 42.76 (Lac C-3), 47.02 (C-5), 62.69 (Gal C-6), 67.38 (Fuc C-5), 67.99 (Gal C-4), 70.03 (Fuc C-2), 71.57 (Fuc C-3), 73.63 (Gal C-2), 73.96 (Fuc C-4), 76.02 (Gal C-5), 76.90 (C-2), 78.03 (Lac C-2), 81.57 (C-1), 83.17 (Gal C-3), 96.51 (Fuc C-1), 101.13 (Gal C-1), 129.74, 130.90, 131.70, 134.40 (6 C, C$_6$H$_5$), 166.83 (C=O), 178.78 (COOH); HR-MS (ESI) m/z: calcd for C$_{38}$H$_{58}$NaO$_{14}$ [M+H]$^+$: 761.3719; found: 761.3723 (0.5 ppm).

Example 8

Figure 8:
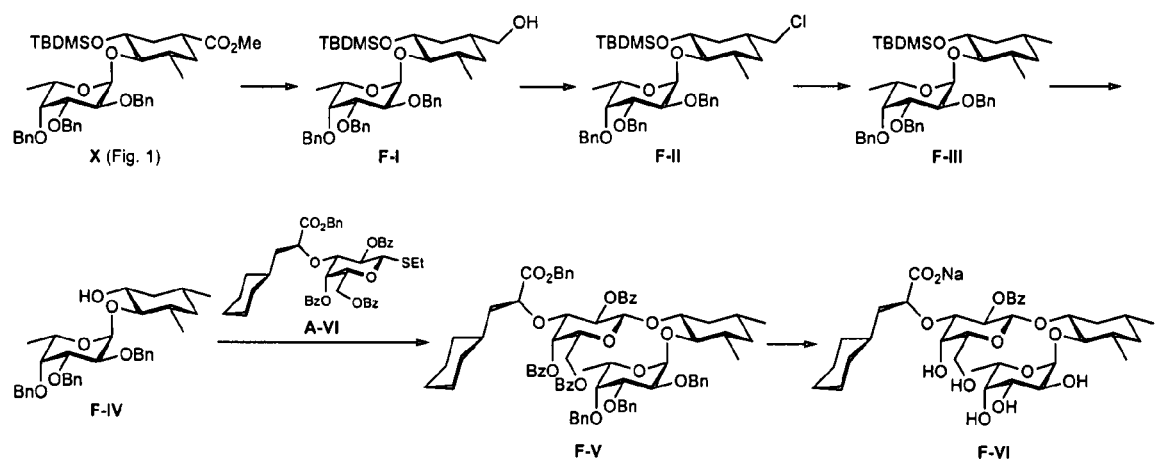
FIG. 8 is a diagram illustrating the synthesis of mimics.
Figure 9:
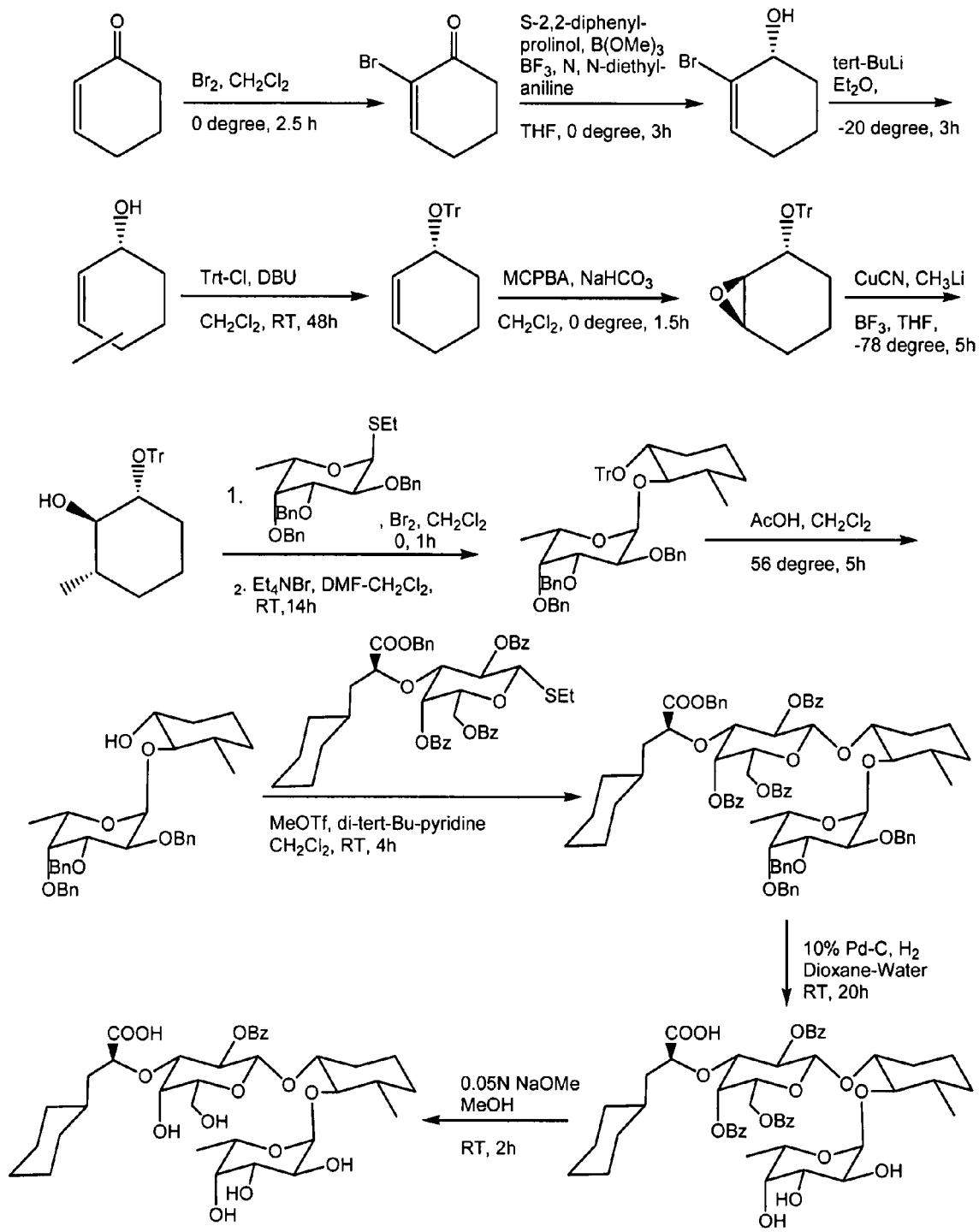
FIG. 9 is a diagram illustrating the synthesis of mimics.

{(1R,2R,3S,5R)-2-[(Deoxy-α-L-Galactopyranosyl)Oxy]-3,5-Dimethyl-Cyclohex-1-yl}2-O-Benzoyl-3-O-[(1S)-1-Carboxy-2-Cyclohexyl-Ethyl]-β-D-Galactopyranoside Sodium Salt (F-VI; FIG. 8)

[(1R,2R,3S,5R)-1-tert-Butyldimethylsilyloxy-5-hydroxymethyl-3-methyl-cyclohex-2-yl]2,3,4-tris-O-benzyl-6-deoxy-α-L-galactopyranoside (F-I)

To a solution of X (137 mg, 0.191 mmol) in dry THF (2 mL) was added a solution of 1 M LiAlH$_4$ (667 µL, 0.667 mmol) in THF at 0° C. under argon over a period of 10 min. After 1 h the reaction was quenched with satd. aqueous (NH$_4$)$_2$SO$_4$ (0.5 mL) and stirred at r.t. for 1 h. Then the mixture was dried with Na$_2$SO$_4$, filtered and the solvent evaporated in vacuo. Column chromatography (petroleum ether/ethyl acetate, 6:1) of the residue gave F-I (110 mg, 84%).

$[\alpha]_D^{20}$=−51.3 (c=0.335, CHCl$_3$); ESI-MS m/z: calcd for C$_{41}$H$_{58}$NaO$_7$Si [M+Na]$^+$: 713.38; found: 713.35.

[(1R,2R,3S,5R)-1-tert-Butyldimethylsilyloxy-5-chloromethyl-3-methyl-cyclohex-2-yl]2,3,4-tris-O-benzyl-6-deoxy-α-L-galactopyranoside (F-II)

To a solution of F-I (105 mg, 0.152 mmol) in dry DCE (1.5 mL) under argon 1-chloro-N,N,2-trimethylpropenylamine (43 µL, 0.304 mmol) was added dropwise. After stirring for 45 min at r.t. the reaction was quenched with MeOH/25% aqueous NH$_3$ (1:1, 0.5 mL) and evaporated to dryness. Column chromatography (petroleum ether/ethyl acetate, 19:1) of the residue yielded F-II (91 mg, 85%).

$[\alpha]_D^{20}$=−46.3 (c=2.20, CHCl$_3$); ESI-MS m/z: calcd. for C$_{41}$H$_{57}$ClNaO$_6$Si [M+Na]$^+$: 731.34; found 731.42.

[(1R,2R,3S,5R)-1-tert-Butyldimethylsilyloxy-3,5-dimethyl-cyclohex-2-yl]2,3,4-tris-O-benzyl-6-deoxy-α-L-galactopyranoside (F-III)

To a solution of F-II (89 mg, 0.125 mmol) and AIBN (21 mg, 0.127 mmol) in dry THF (1.5 mL) was added freshly distilled Bu$_3$SnH (366 µL, 1.38 mmol) via a syringe under argon. After stirring for 90 min at 90° C. the mixture was cooled to r.t. and diluted in MeCN (5 mL). The solution was washed with hexane (5 mL) and the layers were separated. The hexane layer was washed with MeCN (2×5 mL). The combined MeCN layers were evaporated in vacuo and the residue purified by column chromatography (petroleum ether +4% ethyl acetate) to yield F-III (60 mg, 71%).

$[\alpha]_D^{20}$=−43.6 (c=1.28, CHCl$_3$); ESI-MS m/z: calcd. for C$_{41}$H$_{58}$NaO$_6$Si [M+Na]$^+$: 697.97; found 697.47.

[(1R,2R,3S,5R)-1-Hydroxy-3,5-dimethyl-cyclohex-2-yl]2,3,4-tris-O-benzyl-6-deoxy-α-L-galactopyranoside (F-IV)

A mixture of F-III (70 mg, 0.104 mmol), THF (1.5 mL), AcOH (1.8 mL) and H$_2$O (1.5 mL) was stirred for 4 h at 80° C. The mixture was cooled to r.t., neutralized with satd. aqueous NaHCO$_3$ (approx. 14 mL), diluted with DCM (15 mL) and washed with water (15 mL). The aqueous layer was then extracted with DCM (2×10 mL). The combined organic layers were dried with Na$_2$SO$_4$, filtered and evaporated to dryness. Column chromatography (petroleum ether/ethyl acetate, 8:1) of the crude product gave F-IV (40 mg, 68%).

$[\alpha]_D^{20}$=−40.8 (c=2.00, CHCl$_3$); ESI-MS m/z: calcd. for C$_{35}$H$_{44}$NaO$_6$ [M+Na]$^+$: 583.30; found 583.18.

{(1R,2R,3S,5R)-2-[(2,3,4-tris-O-benzyl-6-deoxy-α-L-galactopyranosyl)oxy]-3,5-dimethyl-cyclohex-1-yl}2,4,6-tri-O-benzyl-3-O-[(1S)-1-benzyloxycarbonyl-2-cyclohexyl-ethyl]-β-D-galactopyranoside (F-V)

A mixture of F-IV (45 mg, 80.3 µmol), A-VI (85 mg, 108 µmol) and activated powdered molecular sieves 4 Å (1 g) in DCM (2 mL) was stirred at r.t. under argon for 4 h. Then a pre-stirred mixture (4 h, r.t.) of DMTST (83 mg, 0.321 mmol) and activated powered molecular sieves 4 Å (200 mg) in dry DCM (2 mL) was added. After 24 h the reaction mixture was filtered over Celite and the filtrate was diluted with DCM (10 mL). The organic layer was washed with satd. aqueous NaHCO$_3$ and brine (each 5 mL) and the aqueous layers were extracted with DCM (2×5 ml). The combined organic layers were dried with Na$_2$SO$_4$, filtered and evaporated to dryness. The residue was purified by column chromatography on silica gel (petroleum ether/ethyl acetate, 6:1) to yield F-V (63 mg, 62%).

$[\alpha]_D^{20}$=−47.0 (c=2.17, CHCl$_3$); ESI-MS m/z: calcd. for C$_{78}$H$_{86}$NaOl$_6$ [M+Na]$^+$: 1301.58; found 1301.64.

{(1R,2R,3S,5R)-2-[(deoxy-α-L-galactopyranosyl)oxy]-3,5-dimethyl-cyclohex-1-yl}2-O-benzoyl-3-O-[(1S)-1-carboxy-2-cyclohexyl-ethyl]-β-D-galactopyranoside sodium salt (F-VI; FIG. 8)

A mixture of F-V (50 mg, 39.1 µmol), Pd(OH)$_2$/C (27 mg, 10% Pd), dioxane (1.5 mL) and water (400 µL) was hydrogenated in a Parr-shaker at 5 bar. After 4 h the mixture was filtered over Celite and evaporated to dryness. The residue was re-dissolved in MeOH (3 mL) and NaOMe (97.8 µmol in 160 µL MeOH) was added. After stirring at r.t. for 16 h the reaction was quenched with AcOH (10 µL), concentrated in vacuo and purified by preparative, reversed-phase HPLC. The freeze-dried product was re-dissolved in water and one equivalent of NaOH was added. The solution was lyophilized from water to afford F-VI (23.3 mg, 80%) as a white solid.

$[\alpha]_D^{20}$=−89.0 (c=1.16, H$_2$O); ESI-MS m/z: calcd. for C$_{36}$H$_{54}$NaO$_{14}$ [M+H]$^+$: 733.34; found 733.41.

Example 9

Figure 12:
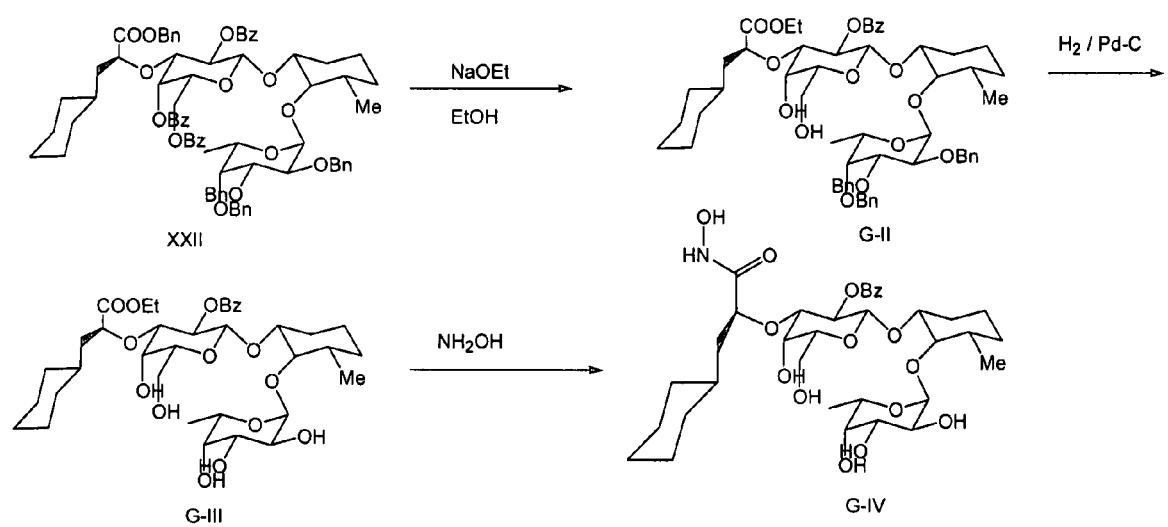
FIG. 12 is a diagram illustrating the synthesis of mimics.

Synthesis of Compound G-IV (FIG. 12)

Synthesis of Intermediate G-II: Compound XXII (100 mg; Example 2) was treated with 0.01N NaOEt in EtOH (2 ml) 2 h at room temperature, neutralized with AcOH and the solution was evaporated to dryness. The residue was purified by column chromatography to give G-II (47 mg).

Synthesis of Intermediate G-III: Compound G-II (250 mg) was dissolved in dioxane-water (10:1, 6.6 ml) and treated with 10% Pd/C under atmosphere of hydrogen for overnight. Solid was filtered off and filtrate was evaporated to dryness. The residue was purified by column chromatography (silica gel) to give compound G-III (100 mg).

Synthesis of compound G-IV: NH$_2$OH. HCl (64 mg) was dissolved in H$_2$O (0.5 ml). To this solution was added a solution of NaOH (70 mg) in H$_2$O (0.5 ml). Compound G-III (25 mg) in MeOH (0.5 ml) was added to the above solution with stirring at room temperature. The mixture was stirred at room temperature for 15 min and then neutralized to pH 7.0 by adding 1N HCl solution. Solvent was evaporated off and the residue was purified by column chromatography (silica gel) to give compound G-IV.

Example 10

Figure 13:
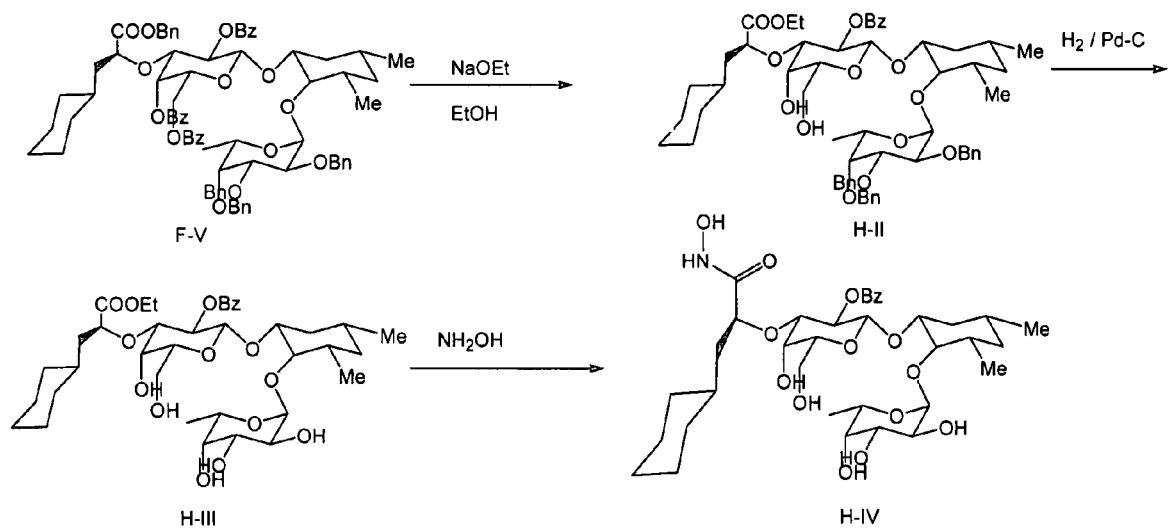
FIG. 13 is a diagram illustrating the synthesis of mimics.

Synthesis of Compound H-IV (FIG. 13)

Synthesis of Intermediate H-II: Compound F-V (100 mg; Example 8) was treated with 0.01N NaOEt in EtOH (2 ml) 2 h at room temperature, neutralized with AcOH and the solution was evaporated to dryness. The residue was purified by column chromatography to give H-II (55 mg).

Synthesis of Intermediate H-III: Compound H-II (125 mg) was dissolved in dioxane-water (10:1, 6.6 ml) and treated with 10% Pd/C under atmosphere of hydrogen for overnight. Solid was filtered off and filtrate was evaporated to dryness. The residue was purified by column chromatography (silica gel) to give compound H-III (75 mg).

Synthesis of compound H-IV: Compound H-III is treated in the same way as described for the synthesis of G-IV to give H-IV.

Example 11

Synthesis of Pegylated Mimic (FIG. 10)

Synthesis of Second Compound of FIG. 10

First compound (100 mg) of FIG. 10 was mixed with ethylenediamine under the argon. The resulting mixture was heated at 70° C. for 7 hr. After evaporation, the residue was purified on C-18 column to afford 55 mg second compound. Yield 68%

PEGylation of Second Compound of FIG. 10

Second compound (5 mg) was mixed with mPEG-nitrophenylcarbonate (5K) 75 mg, triethylamine 5 ul in DMF (2 mL). The resulting mixture was stirred at rt for 3 h. The solvent was removed at reduced pressure. The residue was purified on C-18 to afford 40 mg product.

Example 12

Figure 11:
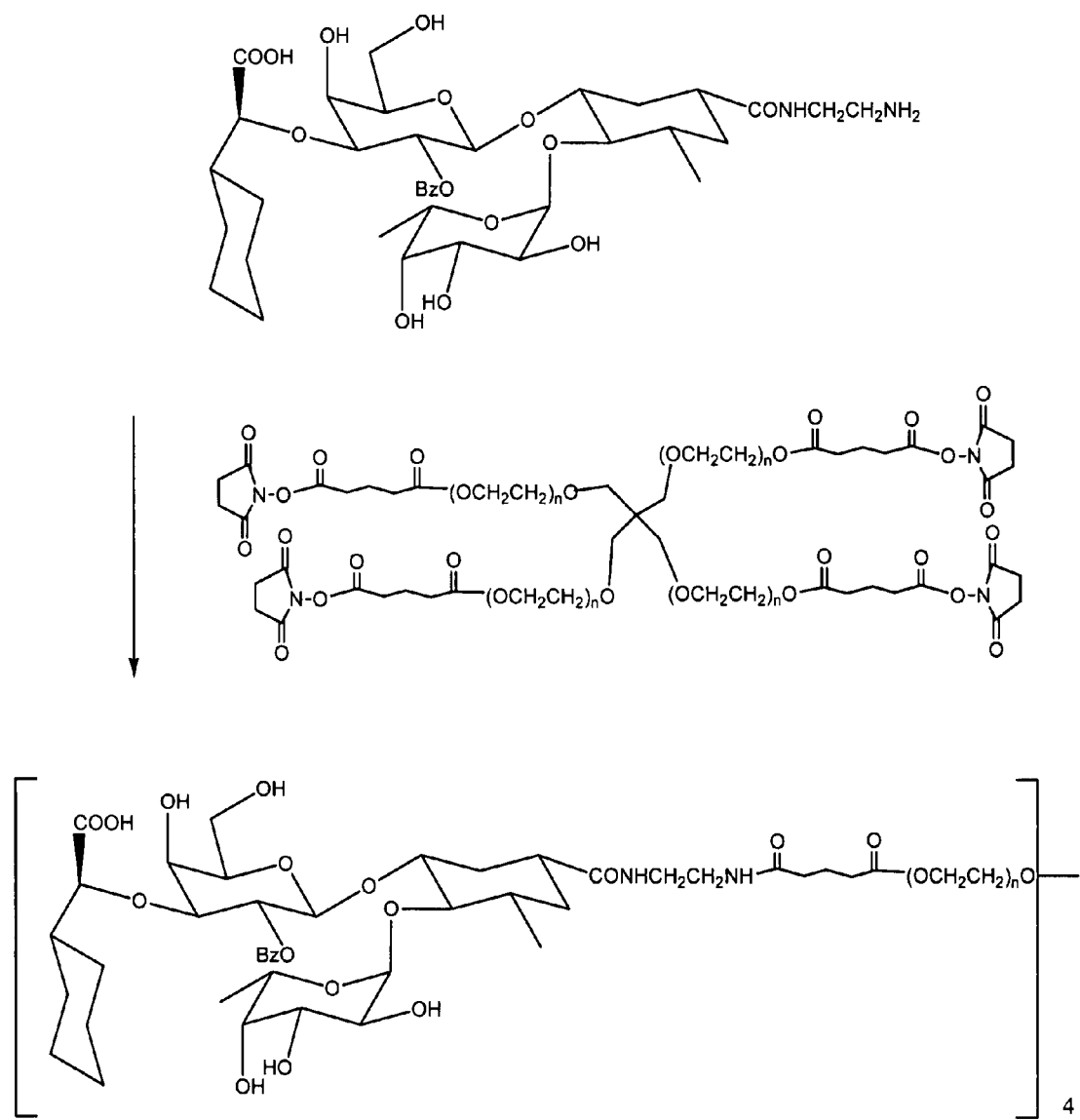
FIG. 11 is a diagram illustrating the synthesis of a pegylated tetramer of a mimic.

Synthesis of Tetramer Pegylated Mimic (FIG. 11)

Second compound (20 mg) from Example 11 was mixed with 200 mg 4-arm PEG glutamidylsuccinate, triethylamine 5 ul and DMF 2 mL. The resulting mixture was stirred at rt for 2 hr. After removing the solvent, the residue was purified on HPLC to afford the product.

Example 13

E-Selectin Assay

E-selectin Protocol: The inhibition assay to screen glycomimetic antagonists of E-selectin is a competitive binding assay, which allows the determination of $IC_{50}$ values. Briefly, E-selectin/1 g chimera is immobilized by incubation at 37° C. in 96 well microtiter plates for 2 hours. To reduce nonspecific binding, bovine serum albumin is added to each well and incubated at room temperature for 2 hours. The plate is washed and serial dilutions of the test compounds are added to the wells in the presence of conjugates of biotinylated, $sLe^a$ polyacrylamide with streptavidin/horseradishperoxidase and incubated for 2 hours at room temperature. To determine the amount of $sLe^a$ bound to immobilized E-selectin after washing, the peroxidase substrate, $3,3^1,5,5^1$ tetramethylbenzidin (TMB) is added. After 3 minutes, the enzyme reaction is stopped by the addition of $H_3PO_4$ and the absorbance of light at a wavelength of 450 nm is determined. The concentration of test compound required to inhibit binding by 50% is determined and reported as the $IC_{50}$ value for each glycomimetic E-selectin antagonist. In addition to reporting the absolute $IC_{50}$ value as measured above, relative $IC_{50}$ values are determined by a ratio of the $IC_{50}$ measured for the test compound to that of a glycomimetic internal control (reference) for each assay. The results from the testing in this assay of several of the compounds disclosed herein are shown below.

| Compounds | $IC_{50}$ (µM) | $rIC_{50}$ |
|---|---|---|
| #1 | 15.5 | 0.076 |
| #2 | 10.1 | 0.049 |
| #3 | 3.75 | 0.027 |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

The invention claimed is:
1. A compound comprising:

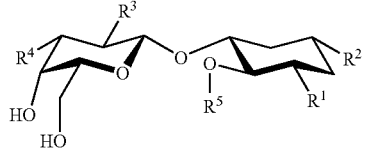

$R^1$=H, $C_1$-$C_8$ alkanyl, $C_1$-$C_8$ alkenyl, $C_1$-$C_8$ alkynyl, halogenated $C_1$-$C_8$ alkanyl, or aryl which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be. substituted with one or more of Me, OMe, halide, or OH; C(=O)OX, alkanyl substituted with C(=O)OX, C(=O)NHX, alkanyl substituted with C(=O)NHX, where X=$C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; OX, NHX, where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH;

$R^2$=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl or heteroaryl either of which may be substituted with one or more of Me, OMe, halide, or OH; —C(=O)OX where X is $C_1$-$C_8$ alkanyl, $C_1$-$C_8$ alkenyl, $C_1$-$C_8$ alkynyl, aryl or heteroaryl either of which may be substituted with one or more of Me, OMe, halide, or OH; —C(=O)

$NH(CH_2)_nNH_2$ where n=0-30, $C(=O)NHX$ or $CX_2OH$, where $X=C_1-C_8$ alkanyl, $C_1-C_8$ alkenyl, $C_1-C_8$ alkynyl, halogenated $C_1-C_8$ alkanyl, aryl or heteroaryl either of which may be substituted with one or more of Me, OMe, halide, or OH; OX, NHX, NH(=O)X, where X=H, $C_1-C_8$ alkanyl, $C_1-C_8$ alkenyl, $C_1-C_8$ alkynyl, halogenated $C_1-C_8$ alkanyl, aryl or heteroaryl either of which may be substituted with one or more of Me, OMe, halide, or OH; with the proviso that $R^1$ and $R^2$ are not both H;

$R^3 = —OH$,

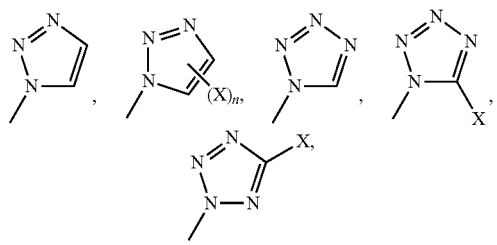

—O—C(=O)—X, —$NH_2$, —NH—C(=O)—NHX, or —NH—C(=O)—X where n=0-2 and X is independently selected from $C_1-C_8$ alkanyl, $C_1-C_8$ alkenyl, $C_1-C_8$ alkynyl,

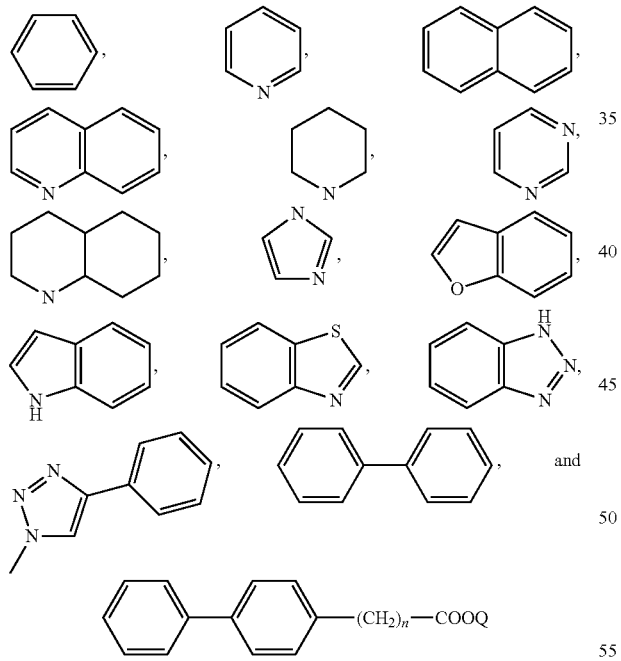

where Q is H or a physiologically acceptable cation, $C_1-C_8$ alkanyl, $C_1-C_8$ alkenyl, $C_1-C_8$ alkynyl, aryl, heteroaryl, $(CH_2)_m$-aryl or $(CH_2)_m$-heteroaryl where m is 1-10, and where n=0-10, and any of the above ring compounds may be substituted with one to three independently selected of Cl, F, $CF_3$, $C_1-C_8$ alkoxy, $NO_2$, $C_1-C_8$ alkanyl, $C_1-C_8$ alkenyl, $C_1-C_8$ alkynyl, $C_1-C_{14}$ aryl, or OY, C(=O)OY, $NY_2$ or C(=O)NHY where Y is H, $C_1-C_8$ alkanyl, $C_1-C_8$ alkenyl, $C_1-C_8$ alkynyl, or $C_1-C_{14}$ aryl;

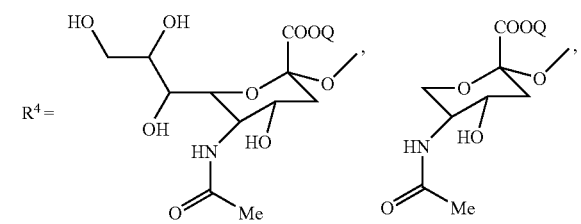

where Q is H or a physiologically acceptable cation; and $R^5$ and $R^9$ is aryl, heteroaryl, cyclohexane, t-butane, adamantane, or triazole, and any of $R^9$ may be substituted with one to three independently selected of Cl, F, $CF_3$, $C_1-C_8$ alkoxy, $NO_2$, $C_1-C_8$ alkanyl, $C_1-C_8$ alkenyl, $C_i-C_8$ alkynyl or OY, C(=O)OY, $NY_2$, or C(=O)NHY where Y is H, $C_1-C_8$ alkanyl, $C_i-C_8$ alkenyl, $C_i-C_8$ alkynyl or $C_i-C_{i4}$ aryl.

2. A compound consisting of the compound of claim 1.

3. The compound according to claim 2 having the formula:

where Q is H or a physiologically acceptable cation, and Me is methyl.

4. The compound according to claim 2 having the formula:

where Q is H or a physiologically acceptable cation, Me is methyl and Bz is benzoyl.

5. The compound according to claim 2 having the formula:

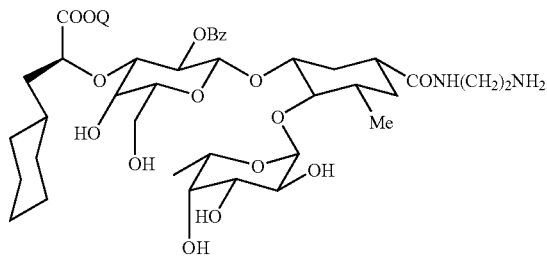

where Q is H or a physiologically acceptable cation, Me is methyl and Bz is benzoyl.

6. The compound according to claim 2 having the formula:

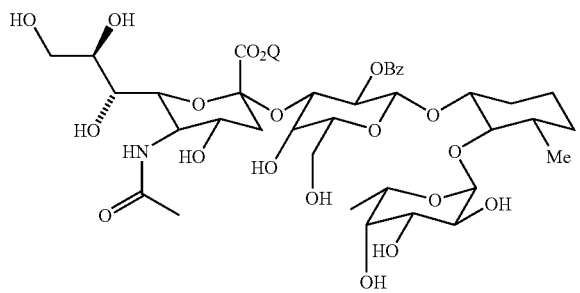

where Q is H or a physiologically acceptable cation, Me is methyl and Bz is benzoyl.

7. The compound according to claim 2 having the formula:

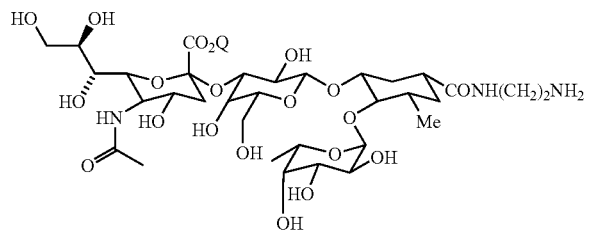

where Q is H or a physiologically acceptable cation, and Me is methyl.

8. The compound according to claim 2 having the formula:

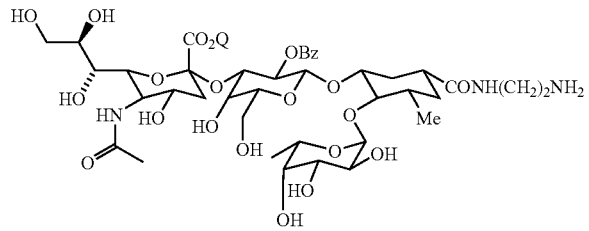

where Q is H or a physiologically acceptable cation, Me is methyl and Bz is benzoyl.

9. The compound according to claim 2 having the formula:

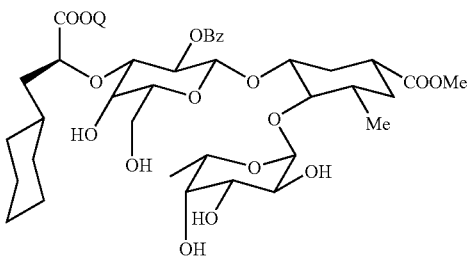

where Q is H or a physiologically acceptable cation, Me is methyl and Bz is benzoyl.

10. The compound according to claim 2 having the formula:

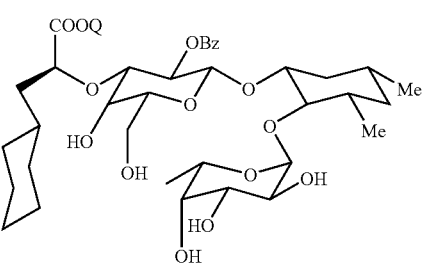

where Q is H or a physiologically acceptable cation, Me is methyl and Bz is benzoyl.

11. The compound according to claim 2 having the formula:

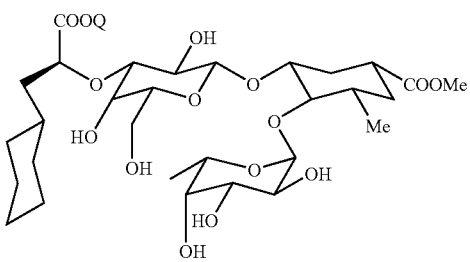

where Q is H or a physiologically acceptable cation, and Me is methyl.

12. The compound according to claim 2 having the formula:
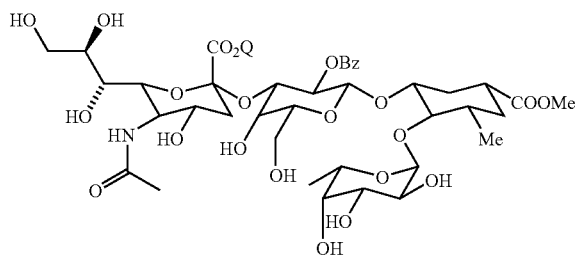
where Q is H or a physiologically acceptable cation, Me is methyl and Bz is benzoyl.
13. The compound according to claim 2 having the formula:
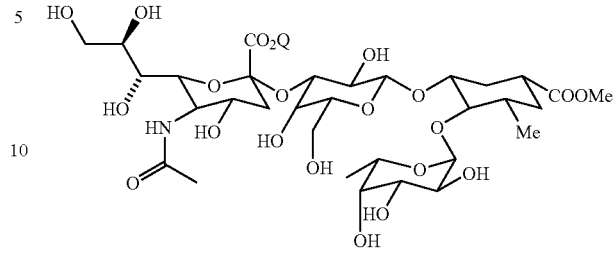
where Q is H or a physiologically acceptable cation, and Me is methyl.
* * * * *

UNITED STATES PATENT AND TRADEMARK OFFICE
CERTIFICATE OF CORRECTION

PATENT NO. : 7,964,569 B2
APPLICATION NO. : 11/973891
DATED : June 21, 2011
INVENTOR(S) : Ernst et al.

It is certified that error appears in the above-identified patent and that said Letters Patent is hereby corrected as shown below:

On title page
Item 56:
"Larsen et al., PASDGEM-Dependent Adhesion of Platelets to Monocytes and Neutrophils is Mediated by a Lineage-Specific Carbohydrate, LNF-III (CD15), *Cell* 63:467-474,1990." should read, --Larsen et al., PADGEM-Dependent Adhesion of Platelets to Monocytes and Neutrophils is Mediated by a Lineage-Specific Carbohydrate, LNF-III (CD15), *Cell* 63:467-474,1990.--.

Column 62, Lines 22-30:
"where Q is H or a physiologically acceptable cation; and $R^5$ and $R^9$ is aryl, heteroaryl, cyclohexane, t-butane, adamantane, or triazole, and any of $R^9$ may be substituted with one to three independently selected of Cl, F, $CF_3$, $C_1$-$C_8$ alkoxy, $NO_2$, $C_1$-$C_8$ alkanyl, $C_1$-$C_8$ alkenyl, $C_i$-$C_8$ alkynyl or OY, C(=O)OY, $NY_2$, or C(=O)NHY where Y is H, $C_1$-$C_8$ alkanyl, $C_i$-$C_8$ alkenyl, $C_i$-$C_8$ alkynyl or $C_i$-$C_{i4}$ aryl." should read, --where Q is H or a physiologically acceptable cation; and $R^5$ = L-fucose and $R^9$ is aryl, heteroaryl, cyclohexane, t-butane, adamantane, or triazole, and any of $R^9$ may be substituted with one to three independently selected of Cl, F, $CF_3$, $C_1$-$C_8$ alkoxy, $NO_2$, $C_1$-$C_8$ alkanyl, $C_1$-$C_8$ alkenyl, $C_1$-$C_8$ alkynyl or OY, C(=O)OY, $NY_2$, or C(=O)NHY where Y is H, $C_1$-$C_8$ alkanyl, $C_1$-$C_8$ alkenyl, $C_1$-$C_8$ alkynyl or $C_1$-$C_{14}$ aryl.--.

Signed and Sealed this
Thirteenth Day of September, 2011

David J. Kappos
*Director of the United States Patent and Trademark Office*